(12) United States Patent
Tada et al.

(10) Patent No.: US 11,673,863 B2
(45) Date of Patent: Jun. 13, 2023

(54) ORGANIC COMPOUND, LIGHT-EMITTING DEVICE, LIGHT-RECEIVING DEVICE, LIGHT-EMITTING APPARATUS, LIGHT-EMITTING MODULE, ELECTRONIC DEVICE, AND LIGHTING DEVICE

(71) Applicant: Semiconductor Energy Laboratory Co., Ltd., Kanagawa-ken (JP)

(72) Inventors: Anna Tada, Kanagawa (JP); Sachiko Kawakami, Kanagawa (JP); Takumu Okuyama, Kanagawa (JP); Tsunenori Suzuki, Kanagawa (JP); Satoshi Seo, Kanagawa (JP)

(73) Assignee: Semiconductor Energy Laboratory Co., Ltd.

( * ) Notice: Subject to any disclaimer, the term of this patent is extended or adjusted under 35 U.S.C. 154(b) by 328 days.

(21) Appl. No.: 16/924,717

(22) Filed: Jul. 9, 2020

(65) Prior Publication Data

US 2021/0009518 A1    Jan. 14, 2021

(30) Foreign Application Priority Data

Jul. 12, 2019    (JP) .............................. JP2019-129980

(51) Int. Cl.
    *H01L 51/00*       (2006.01)
    *C07D 209/82*     (2006.01)
    *H01L 51/50*       (2006.01)

(52) U.S. Cl.
    CPC ........ *C07D 209/82* (2013.01); *H01L 51/0052* (2013.01); *H01L 51/0059* (2013.01); *H01L 51/0072* (2013.01); *H01L 51/5088* (2013.01)

(58) Field of Classification Search
    CPC . C07D 209/82; C07D 209/86; H01L 51/0052; H01L 51/0059; H01L 51/0072; H01L 51/5088; H01L 51/0056; H01L 51/42; H01L 51/5012; H01L 51/5056; H01L 51/0061; Y02E 10/549; C09K 11/06; C09K 2211/1011; C09K 2211/1014; C09K 2211/1029
    USPC ......................................................... 428/690
    See application file for complete search history.

(56) References Cited

U.S. PATENT DOCUMENTS

| | | | |
|---|---|---|---|
| 7,651,787 B2 | 1/2010 | Seo et al. | |
| 2007/0215889 A1 | 9/2007 | Kawakami et al. | |

(Continued)

FOREIGN PATENT DOCUMENTS

| | | | | |
|---|---|---|---|---|
| CN | 108336246 A | | 7/2018 | |
| CN | 108976162 A | * | 12/2018 | ........... C07D 209/86 |

(Continued)

OTHER PUBLICATIONS

Ho, M. et al., "P-131: Novel Deep Blue Dopants for Organic Light Emitting Devices," SID Digest '05: SID International Symposium Digest of Technical Papers, May 24, 2005, vol. 36, pp. 802-805.

*Primary Examiner* — Douglas J McGinty
(74) *Attorney, Agent, or Firm* — Husch Blackwell LLP

(57) ABSTRACT

An organic compound with high heat resistance is provided. A light-emitting device with high emission efficiency and high reliability is provided. An organic compound represented by General Formula (G0) is provided. In General Formula (G0), any one of $R^1$ to $R^5$ represents General Formula (A), and each of the others of $R^1$ to $R^5$, $R^6$ to $R^{13}$, $R^{21}$ to $R^{29}$, $R^{31}$ to $R^{39}$, and $R^{41}$ to $R^{48}$ independently represents hydrogen, an alkyl group having 1 to 6 carbon atoms, a cycloalkyl group having 3 to 6 carbon atoms, or a substituted or unsubstituted aryl group having 6 to 13 carbon atoms. $R^{21}$ and $R^{22}$ may be bonded to each other to form a spiro ring.

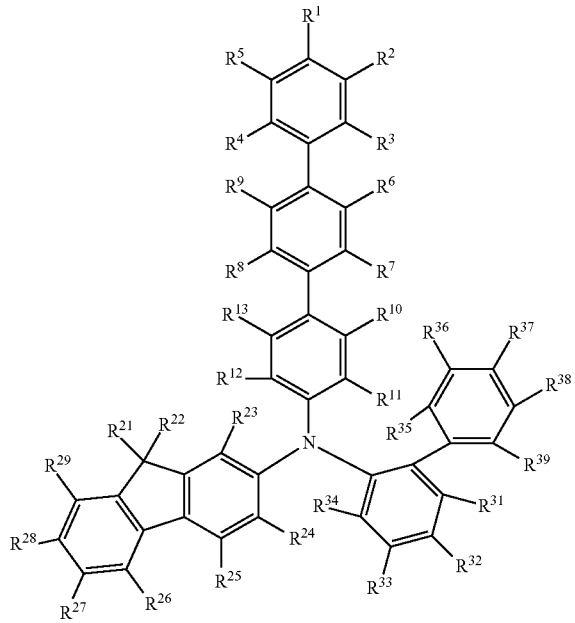

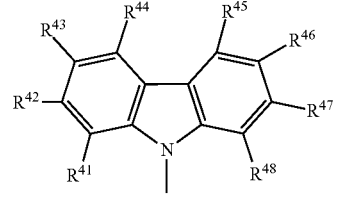

12 Claims, 23 Drawing Sheets

(56) References Cited

U.S. PATENT DOCUMENTS

| | | | |
|---|---|---|---|
| 2013/0076237 A1 | 3/2013 | Nomura et al. | |
| 2016/0028019 A1* | 1/2016 | Jeong | H01L 51/0067 257/40 |
| 2017/0040535 A1 | 2/2017 | Ogita et al. | |
| 2017/0222156 A1 | 8/2017 | Kawakami et al. | |
| 2019/0229271 A1 | 7/2019 | Lee et al. | |
| 2020/0058882 A1* | 2/2020 | Lee | H01L 51/0067 |

FOREIGN PATENT DOCUMENTS

| | | |
|---|---|---|
| JP | 2003-031371 A | 1/2003 |
| JP | 2003-317946 A | 11/2003 |
| JP | 2009-076817 A | 4/2009 |
| JP | 2009-298779 A | 12/2009 |
| KR | 2015-0004099 A | 1/2015 |
| KR | 2018-0042943 A | 4/2018 |
| KR | 2018-0096458 A | 8/2018 |
| KR | 2018-0131115 A | 12/2018 |
| WO | WO 2017/204556 A1 | 11/2017 |

\* cited by examiner

ORGANIC COMPOUND, LIGHT-EMITTING DEVICE, LIGHT-RECEIVING DEVICE, LIGHT-EMITTING APPARATUS, LIGHT-EMITTING MODULE, ELECTRONIC DEVICE, AND LIGHTING DEVICE

BACKGROUND OF THE INVENTION

1. Field of the Invention

One embodiment of the present invention relates to an organic compound, a light-emitting device, a light-emitting apparatus, a light-emitting module, an electronic device, and a lighting device.

Note that one embodiment of the present invention is not limited to the above technical field. Examples of the technical field of one embodiment of the present invention include a semiconductor device, a display device, a light-emitting apparatus, a power storage device, a memory device, an electronic device, a lighting device, an input device (e.g., a touch sensor), an input/output device (e.g., a touch panel), a driving method thereof, and a manufacturing method thereof.

2. Description of the Related Art

Research and development have been actively conducted on light-emitting devices using organic electroluminescence (EL) phenomenon (also referred to as organic EL devices or organic EL elements). In a basic structure of an organic EL device, a layer containing a light-emitting organic compound (hereinafter also referred to as a light-emitting layer) is sandwiched between a pair of electrodes. By voltage application to the organic EL device, light emission from the light-emitting organic compound can be obtained.

An organic EL device is suitable for a display device because it has features such as ease of thinning and lightening, high-speed response to an input signal, and driving with a direct-current low voltage source.

Furthermore, an organic EL device can be formed in a film form, and thus can provide planar light emission. Accordingly, a large-area light-emitting device can be easily formed. This feature is difficult to obtain with a point light source typified by a light-emitting diode (LED) or a linear light source typified by a fluorescent lamp. Thus, an organic EL device also has great potential as a planar light source applicable to a lighting device and the like.

Patent Document 1 discloses an aromatic amine compound having a high hole-transport property as a material that can be used for a light-emitting device.

REFERENCE

Patent Document

[Patent Document 1] Japanese Published Patent Application No. 2009-298779

SUMMARY OF THE INVENTION

An object of one embodiment of the present invention is to provide a novel organic compound. Another object of one embodiment of the present invention is to provide an organic compound with high heat resistance. Another object of one embodiment of the present invention is to provide an organic compound with high sublimability. Another object of one embodiment of the present invention is to provide a novel organic compound that can be used for a light-emitting device. Another object of one embodiment of the present invention is to provide a novel organic compound that can be used as a hole-transport material in a light-emitting device. Another object of one embodiment of the present invention is to provide a novel organic compound that can be used as a host material, in which a light-emitting substance is dispersed, in a light-emitting device.

Another object of one embodiment of the present invention is to provide a light-emitting device having high emission efficiency. Another object of one embodiment of the present invention is to provide a light-emitting device with a low driving voltage. Another object of one embodiment of the present invention is to provide a light-emitting device with a long lifetime. Another object of one embodiment of the present invention is to provide a light-emitting device with high heat resistance.

Note that the description of these objects does not disturb the existence of other objects. One embodiment of the present invention does not necessarily achieve all the objects. Other objects can be derived from the description of the specification, the drawings, and the claims.

One embodiment of the present invention is an organic compound represented by General Formula (G0).

[Chemical Formula 1]

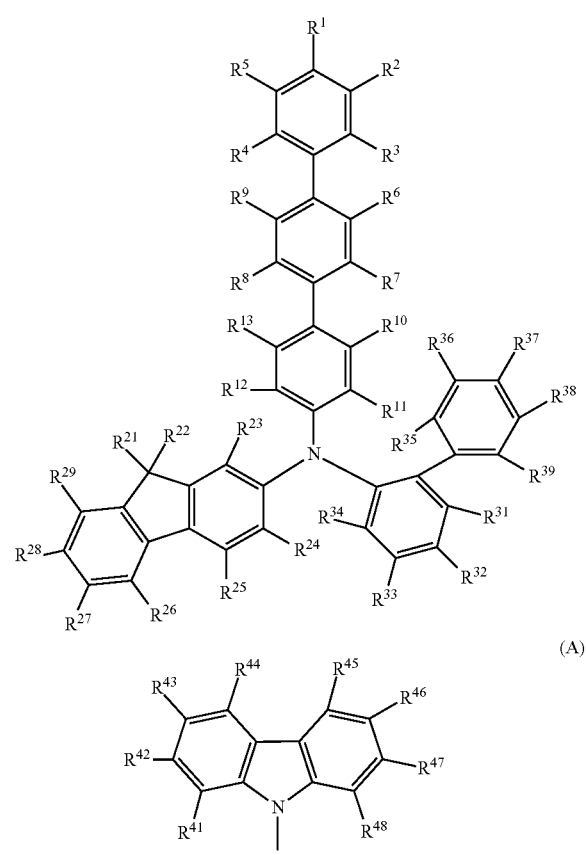

In General Formula (G0), any one of $R^1$ to $R^5$ represents General Formula (A); each of the others independently represents hydrogen, an alkyl group having 1 to 6 carbon atoms, a cycloalkyl group having 3 to 6 carbon atoms, or a substituted or unsubstituted aryl group having 6 to 13 carbon atoms; and each of $R^6$ to $R^{13}$, $R^{21}$ to $R^{29}$, $R^{31}$ to $R^{39}$, and $R^{41}$ to $R^{48}$ independently represents hydrogen, an alkyl group having 1 to 6 carbon atoms, a cycloalkyl group having 3 to 6 carbon atoms, or a substituted or unsubstituted aryl group having 6 to 13 carbon atoms. Furthermore, $R^{21}$ and $R^{22}$ may be bonded to each other to form a spiro ring One embodiment of the present invention is an organic compound represented by General Formula (G1).

[Chemical Formula 2]

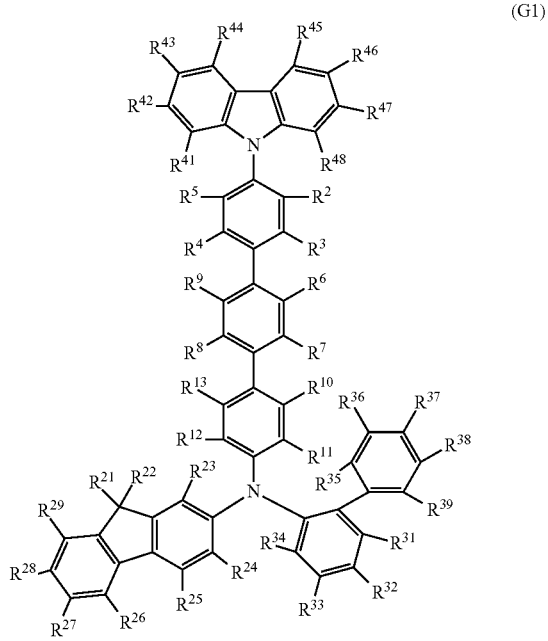

(G1)

In General Formula (G1), each of $R^2$ to $R^{13}$, $R^{21}$ to $R^{29}$, $R^{31}$ to $R^{39}$, and $R^{41}$ to $R^{48}$ independently represents hydrogen, an alkyl group having 1 to 6 carbon atoms, a cycloalkyl group having 3 to 6 carbon atoms, or a substituted or unsubstituted aryl group having 6 to 13 carbon atoms. Furthermore, $R^{21}$ and $R^{22}$ may be bonded to each other to form a spiro ring.

In General Formulae (G0) and (G1), one of $R^{35}$ to $R^{39}$ preferably represents a substituted or unsubstituted phenyl group or a substituted or unsubstituted naphthyl group.

In General Formulae (G0) and (G1), it is preferable that $R^{21}$ and $R^{22}$ be the same and represent an alkyl group having 1 to 6 carbon atoms or a substituted or unsubstituted phenyl group.

In General Formulae (G0) and (G1), each of $R^{21}$ and $R^{22}$ preferably represents a methyl group. Alternatively, each of $R^{21}$ and $R^{22}$ preferably represents an unsubstituted phenyl group. Alternatively, $R^{21}$ and $R^{22}$ are preferably bonded to each other to form a spiro ring. For example, it is preferable that each of $R^{21}$ and $R^{22}$ represent a substituted or unsubstituted phenyl group and the phenyl groups be bonded to each other to form a spirobifluorene ring.

In General Formulae (G0) and (G1), it is preferable that each of $R^{41}$ to $R^{48}$ independently represent hydrogen, a methyl group, a tert-butyl group, or a substituted or unsubstituted phenyl group.

One embodiment of the present invention is a light-emitting device, a light-receiving device, or a light-emitting and light-receiving device which includes any of the above-described organic compounds.

One embodiment of the present invention is a light-emitting device, a light-receiving device, or a light-emitting and light-receiving device which includes a layer containing an organic compound between a pair of electrodes. The layer containing an organic compound includes any of the above-described organic compounds.

One embodiment of the present invention is a light-emitting device which includes a layer containing an organic compound between a pair of electrodes. The layer containing an organic compound includes a light-emitting layer and a hole-transport layer, and at least one of the light-emitting layer and the hole-transport layer includes any of the above-described organic compounds.

One embodiment of the present invention is a light-emitting apparatus including any of the above-described light-emitting devices and one or both of a transistor and a substrate.

One embodiment of the present invention is a light-emitting module including the light-emitting apparatus. The light-emitting module is provided with a flexible printed circuit (hereinafter referred to as an FPC) or a connector such as a tape carrier package (TCP), or mounted with an integrated circuit (IC) by a chip on glass (COG) method, a chip on film (COF) method, or the like. Note that the light-emitting module of one embodiment of the present invention may include only one of a connector and an IC or both of them.

One embodiment of the present invention is an electronic device including the aforementioned light-emitting module and at least one of an antenna, a battery, a housing, a camera, a speaker, a microphone, and an operation button.

One embodiment of the present invention is a lighting device including any of the above-described light-emitting devices and at least one of a housing, a cover, and a support base.

One embodiment of the present invention can provide a novel organic compound. One embodiment of the present invention can provide an organic compound with high heat resistance. One embodiment of the present invention can provide an organic compound with high sublimability. One embodiment of the present invention can provide a novel organic compound that can be used for a light-emitting device. One embodiment of the present invention can provide a novel organic compound that can be used as a hole-transport material in a light-emitting device. One embodiment of the present invention can provide a novel organic compound that can be used as a host material, in which a light-emitting substance is dispersed, in a light-emitting device.

One embodiment of the present invention can provide a light-emitting device with high emission efficiency. One embodiment of the present invention can provide a light-emitting device with low driving voltage. One embodiment of the present invention can provide a light-emitting device with a long lifetime. One embodiment of the present invention can provide a light-emitting device with high heat resistance.

Note that the description of these effects does not preclude the existence of other effects. One embodiment of the present invention does not necessarily have all of these effects. Other effects can be derived from the description of the specification, the drawings, and the claims.

DETAILED DESCRIPTION OF THE INVENTION

Figure 1A:
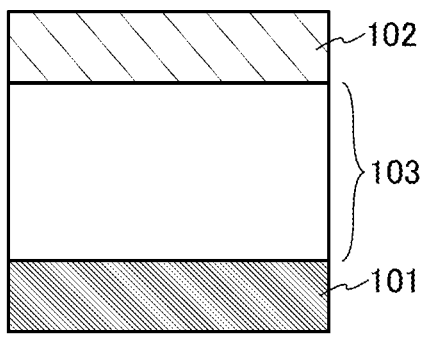
FIGS. 1A to 1D are cross-sectional views illustrating examples of light-emitting devices.

Embodiments will be described in detail with reference to the drawings. Note that the present invention is not limited to the following description, and it will be readily understood by those skilled in the art that modes and details of the present invention can be modified in various ways without departing from the spirit and scope of the present invention. Therefore, the present invention should not be construed as being limited to the description in the following embodiments.

Note that in the structures of the invention described below, the same portions or portions having similar functions are denoted by the same reference numerals in different drawings, and description of such portions is not repeated. The same hatching pattern is used for portions having similar functions, and the portions are not denoted by specific reference numerals in some cases.

In addition, the position, size, range, or the like of each structure illustrated in drawings does not represent the actual position, size, range, or the like in some cases for easy understanding. Therefore, the disclosed invention is not necessarily limited to the position, size, range, or the like disclosed in the drawings.

Note that the terms "film" and "layer" can be used interchangeably depending on the case or the circumstances. For example, the term "conductive layer" can be changed into the term "conductive film". As another example, the term "insulating film" can be changed into the term "insulating layer".

Embodiment 1

In this embodiment, an organic compound of one embodiment of the present invention will be described.

[Structure of Organic Compound of One Embodiment of the Present Invention]

An organic compound of one embodiment of the present invention is a tertiary amine. To nitrogen of the amine, the ortho position of a biphenyl skeleton, a fluorene skeleton, and a terphenylene skeleton are bonded. A carbazole skeleton is bonded to a phenylene group that is the farthest from nitrogen of amine of the terphenylene skeleton.

A light-emitting device used in a high-temperature environment, for example, in a car, is required to have high heat resistance. Also in the case where high temperature is applied during a product manufacturing process, for example, in a sealing step using glass frit, the light-emitting device is required to have high heat resistance. For these reasons, a material used for the light-emitting device needs to have a glass transition temperature (Tg) of 100° C. or higher, furthermore, 120° C. or higher in some cases. In one embodiment of the present invention, the Tg of the organic compound can be 100° C. or higher, furthermore, 120° C. or higher; accordingly, a material suitable for a light-emitting device that is required to have high heat resistance can be provided. In many cases, light-emitting devices are manufactured by vacuum evaporation. In that case, materials used for the light-emitting devices need to have high heat resistance and high sublimability. The sublimation temperature is preferably 500° C. or lower, more preferably 400° C. or lower. In one embodiment of the present invention, a material having not only high heat resistance but also high sublimability can be provided; that is, a material with high productivity in terms of device manufacturing can be provided.

The organic compound of one embodiment of the present invention has a high hole-transport property and a high electron-blocking property. The organic compound of one embodiment of the present invention can be used as a hole-transport material in the light-emitting device. The organic compound of one embodiment of the present invention can be used as a host material, in which a light-emitting substance is dispersed, in the light-emitting device. The light-emitting device can have high emission efficiency and high reliability by including the organic compound of one embodiment of the present invention.

The organic compound of one embodiment of the present invention can be used as a carrier-transport material (hole-transport material), in a light-receiving device, such as an organic photodiode, or a light-receiving and light-emitting device, which has both a light-receiving function and a light-emitting function.

Specifically, one embodiment of the present invention is an organic compound represented by General Formula (G0). Note that not only organic compounds with the structures represented by the following general formulae, but also materials for light-emitting devices with the structures and materials for light-receiving devices with the structures are each one embodiment of the present invention.

[Chemical Formula 3]

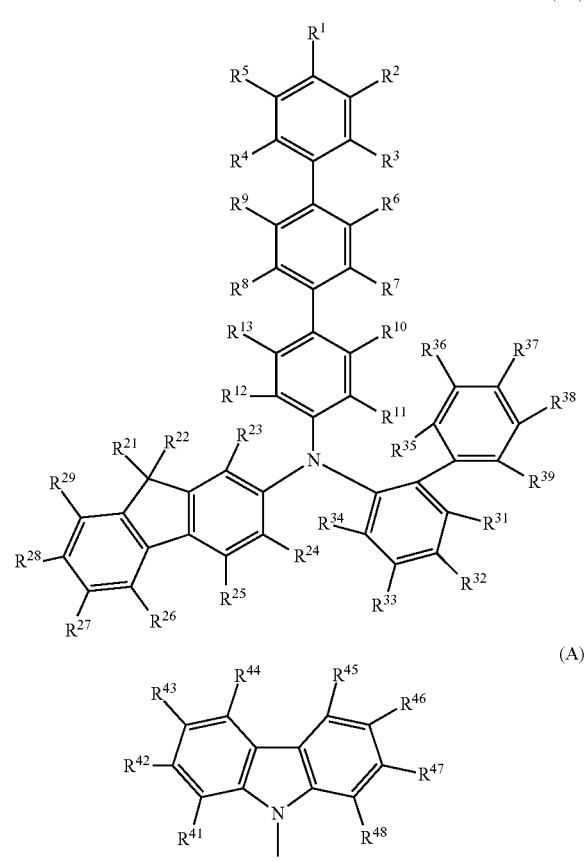

(G0)

(A)

In General Formula (G0), any one of $R^1$ to $R^5$ represents General Formula (A); each of the others independently represents hydrogen, an alkyl group having 1 to 6 carbon atoms, a cycloalkyl group having 3 to 6 carbon atoms, or a substituted or unsubstituted aryl group having 6 to 13 carbon atoms; each of $R^6$ to $R^{13}$, $R^{21}$ to $R^{29}$, $R^{31}$ to $R^{39}$, and $R^{41}$ to $R^{48}$ independently represents hydrogen, an alkyl group having 1 to 6 carbon atoms, a cycloalkyl group having 3 to 6 carbon atoms, or a substituted or unsubstituted aryl group having 6 to 13 carbon atoms; and $R^{21}$ and $R^{22}$ may be bonded to each other to form a spiro ring.

Among organic compounds represented by General Formula (G0), organic compounds represented by General Formula (G1) are more preferable. A molecular structure in which a carbazolyl group is bonded to the para position of a terphenylene skeleton can increase the heat resistance of an organic compound as compared with a molecular structure in which a carbazolyl group is bonded to the ortho position or the meta position of a terphenylene skeleton.

[Chemical Formula 4]

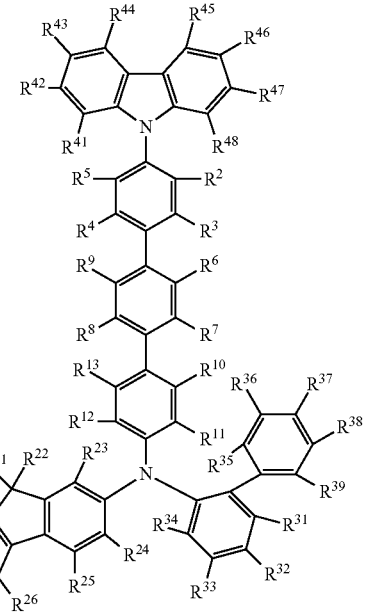

(G1)

In General Formula (G1), each of $R^2$ to $R^{13}$, $R^{21}$ to $R^{29}$, $R^{31}$ to $R^{39}$, and $R^{41}$ to $R^{48}$ independently represents hydrogen, an alkyl group having 1 to 6 carbon atoms, a cycloalkyl group having 3 to 6 carbon atoms, or a substituted or unsubstituted aryl group having 6 to 13 carbon atoms; and $R^{21}$ and $R^{22}$ may be bonded to each other to form a spiro ring.

It is preferable that any one of $R^{35}$ to $R^{39}$ represent a substituted or unsubstituted phenyl group or a substituted or unsubstituted naphthyl group. This can increase heat resistance of the organic compound.

In the case where the ninth position of a fluorenyl group is hydrogen, the acidity of the hydrogen is increased, which might reduce the reliability of a light-emitting device; therefore, $R^{21}$ and $R^{22}$ each of which is at the ninth position of a fluorenyl group preferably represent a substituent not hydrogen. In consideration of the heat resistance and the sublimability of the organic compound represented by General Formula (G1), it is preferable that each of $R^{21}$ and $R^{22}$ independently represent an alkyl group having 1 to 6 carbon atoms or a substituted or unsubstituted phenyl group. Alternatively, it is preferable that $R^{21}$ and $R^{22}$ be the same and represent an alkyl group having 1 to 6 carbon atoms or a substituted or unsubstituted phenyl group.

In terms of the synthesis cost, $R^{21}$ and $R^{22}$ are preferably the same.

Each of $R^{21}$ and $R^{22}$ preferably represents a methyl group. This can increase sublimability of the organic compound. Alternatively, each of $R^{21}$ and $R^{22}$ preferably represents an unsubstituted phenyl group. This can increase heat resistance of the organic compound.

Alternatively, $R^{21}$ and $R^{22}$ are preferably bonded to each other to form a spiro ring in order to achieve high heat resistance and high reliability. For example, it is preferable that each of $R^{21}$ and $R^{22}$ represent a substituted or unsubstituted phenyl group and the phenyl groups be bonded to each other to form a spirobifluorene ring.

It is preferable that each of $R^{41}$ to $R^{48}$ independently represent hydrogen, a methyl group, a tert-butyl group, or a substituted or unsubstituted phenyl group in order to achieve high sublimability or high reliability.

Examples of the alkyl group having 1 to 6 carbon atoms in General Formulae (G0) and (G1) include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a 3-methylpentyl group, a 2-methylpentyl group, a 2-ethylbutyl group, a 1,2-dimethylbutyl group, a 2,3-dimethylbutyl group, and an n-heptyl group.

Examples of the cycloalkyl group having 3 to 6 carbon atoms in General Formulae (G0) and (G1) include a cyclopropyl group, a cyclobutyl group, a cyclopentyl group, and a cyclohexyl group.

Examples of the substituted or unsubstituted aryl group having 6 to 13 carbon atoms in General Formulae (G0) and (G1) include a phenyl group, an o-tolyl group, an m-tolyl group, a p-tolyl group, a mesityl group, an o-biphenyl group, an m-biphenyl group, a p-biphenyl group, a 1-naphthyl group, a 2-naphthyl group, a 9H-fluorenyl group, a 9,9-dimethyl-9H-fluorenyl group, and a 9,9'-spirobi[9H-fluoren]-yl group.

As to a "substituted or unsubstituted X" (X refers to a ring, a skeleton, a group, or the like) in General Formulae (G0) and (G1), when the X has a substituent, examples of the substituent include an alkyl group having 1 to 6 carbon atoms, such as a methyl group, an ethyl group, a propyl group, an isopropyl group, a butyl group, an isobutyl group, a sec-butyl group, a tert-butyl group, a pentyl group, or a hexyl group; a cycloalkyl group having 3 to 6 carbon atoms, such as a cyclopropyl group, a cyclobutyl group, a cyclopentyl group, or a cyclohexyl group; and an aryl group having 6 to 13 carbon atoms, such as a phenyl group, a naphthyl group, or a biphenyl group.

Specific examples of the compound of one embodiment of the present invention include organic compounds represented by Structural Formulae (100) to (246). Note that the present invention is not limited to these examples.

[Chemical Formula 5]

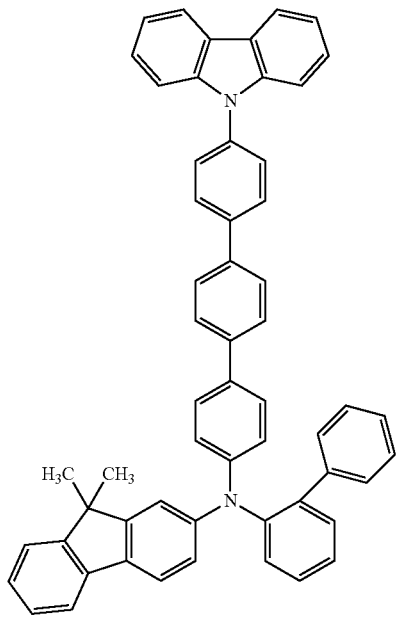

(100)

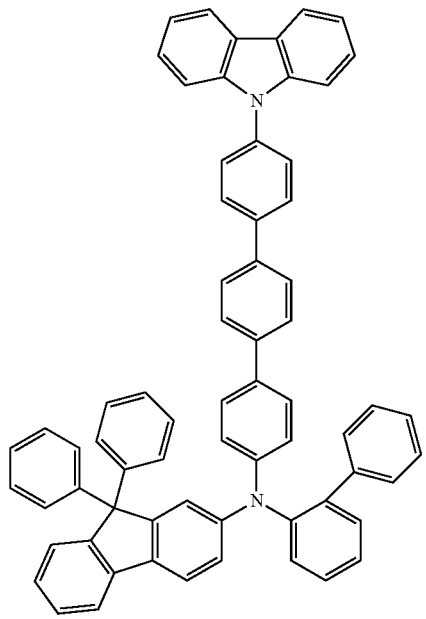

(101)

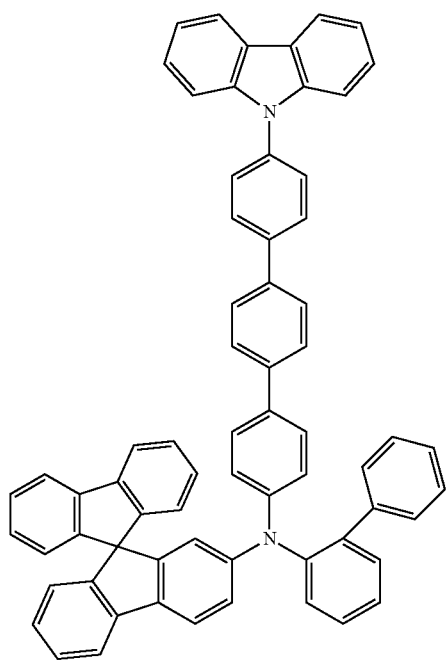 (102)
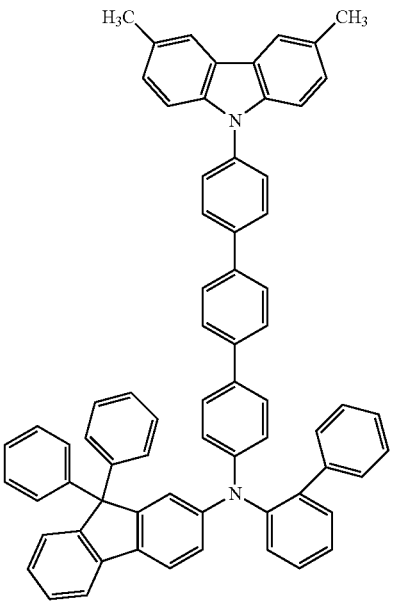 (104)
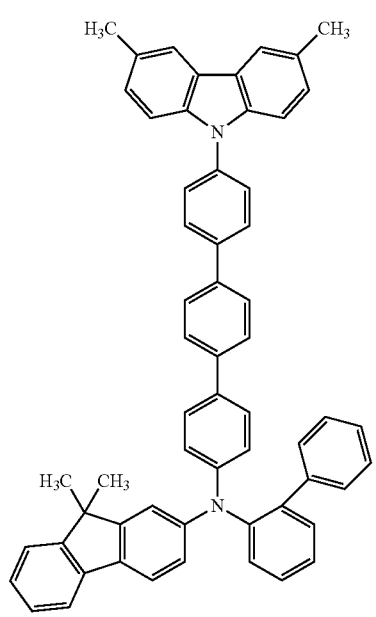 (103)
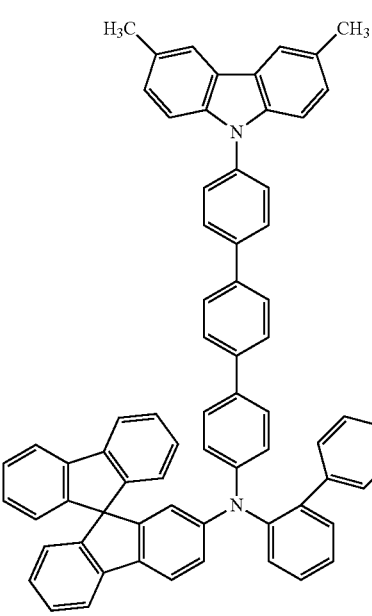 (105)

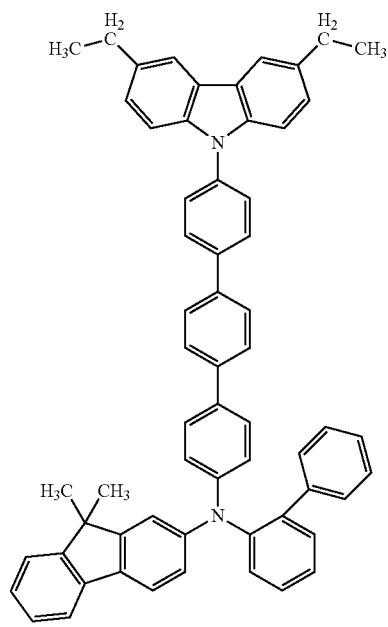
(106)
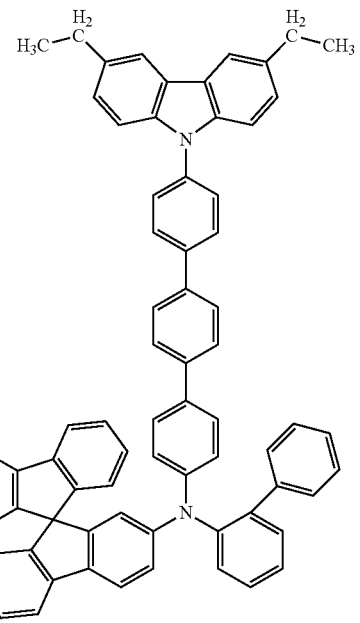
(108)
[Chemical Formula 6]
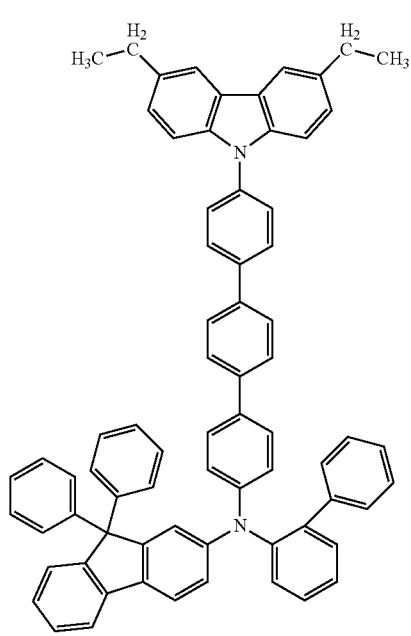
(107)
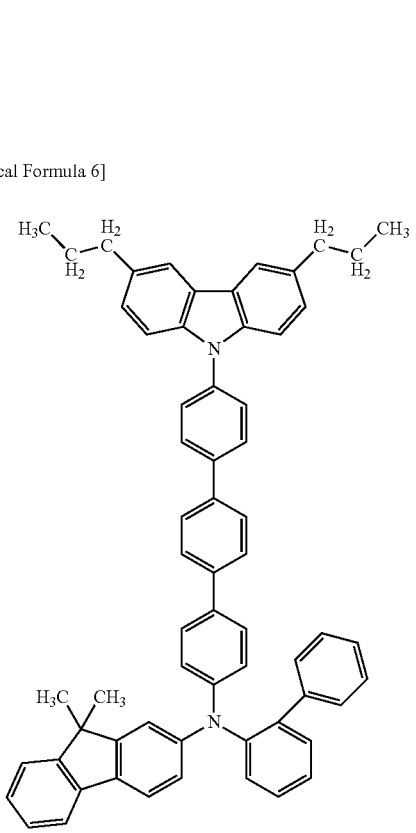
(109)

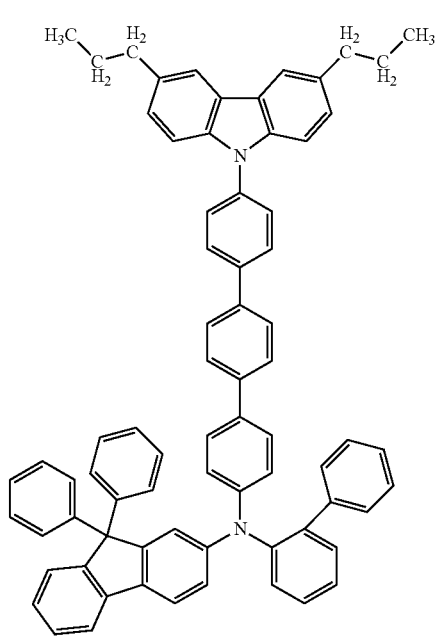
(110)
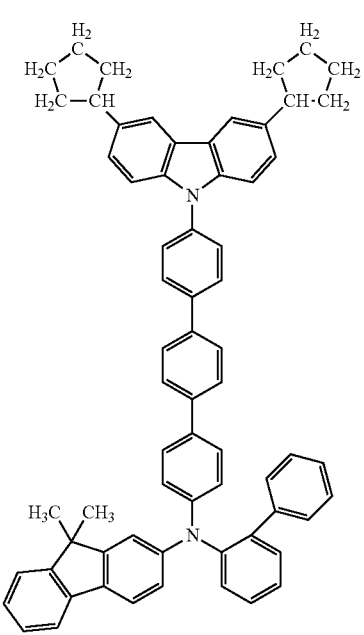
(112)
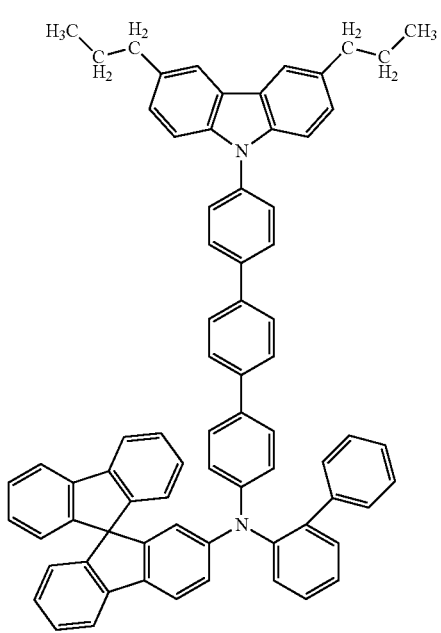
(111)
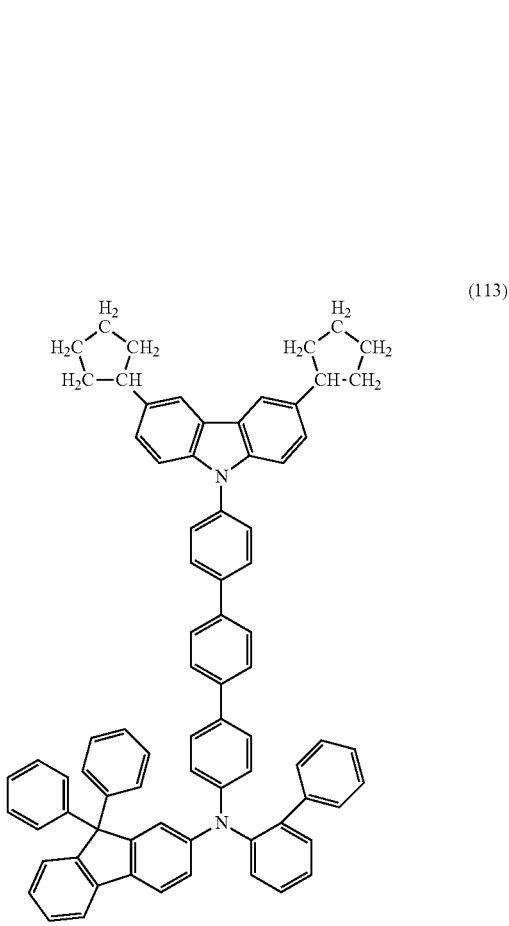
(113)

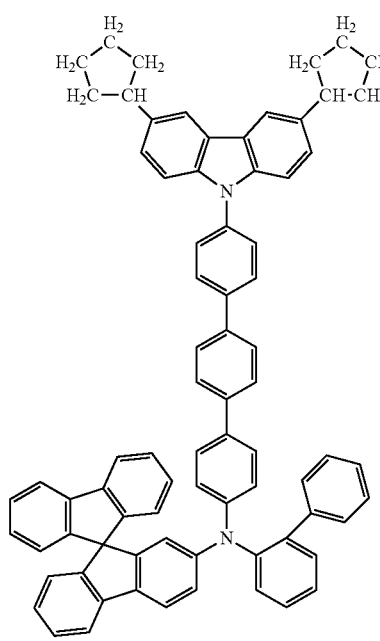
(114)
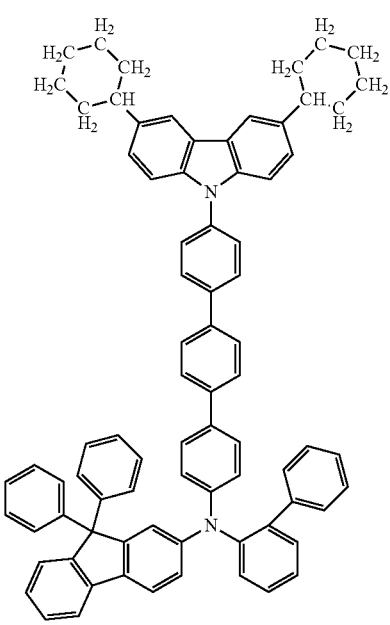
(116)
[Chemical Formula 7]
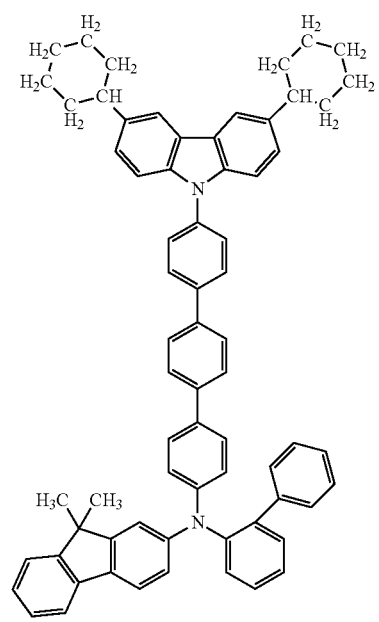
(115)
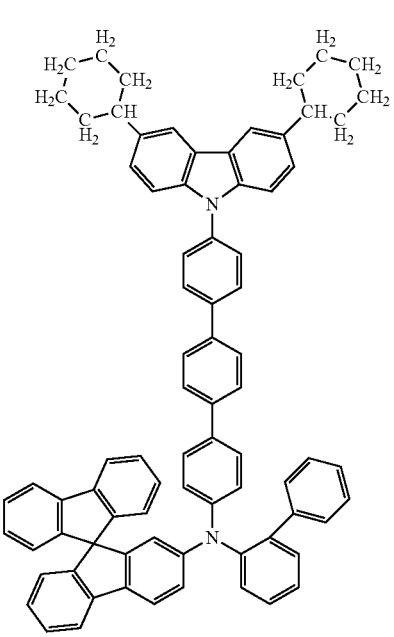
(117)

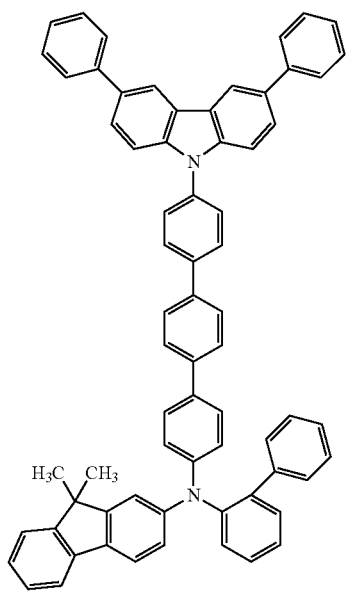
(118)
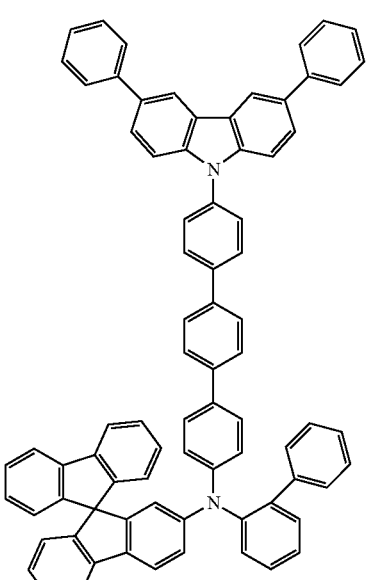
(120)
[Chemical Formula 8]
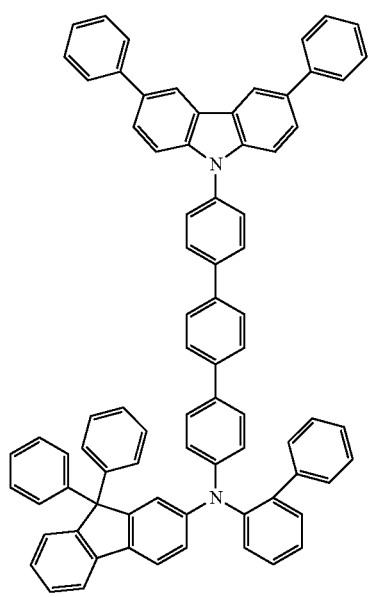
(119)
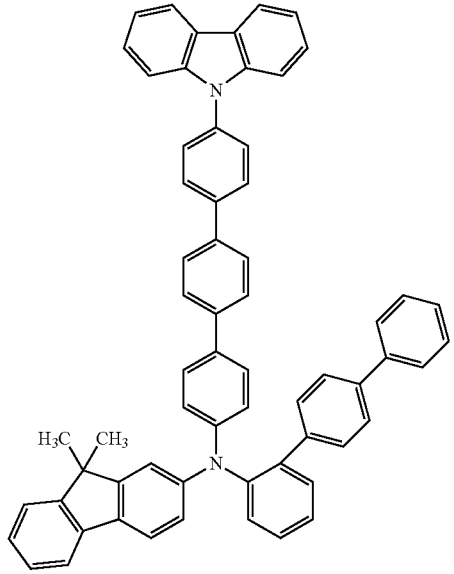
(121)

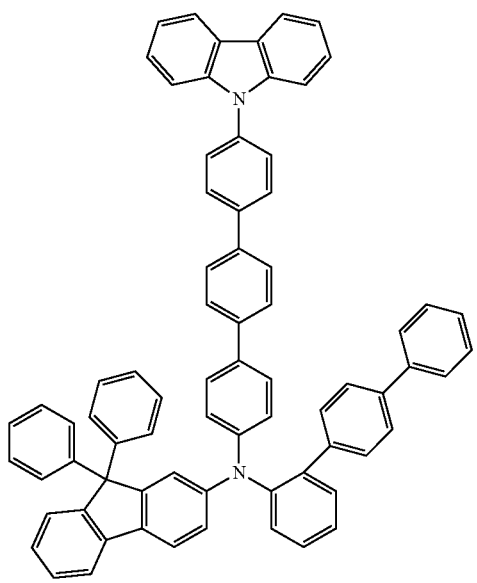
(122)
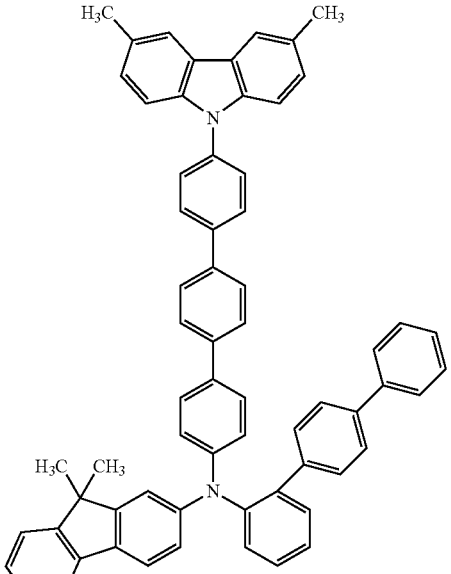
(124)
(123)
(125)

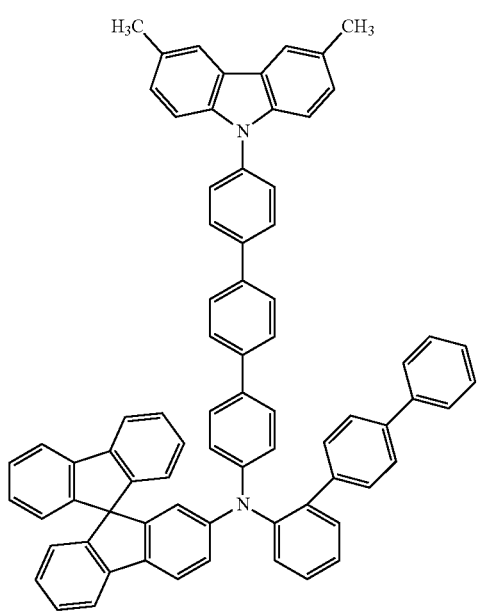
(126)
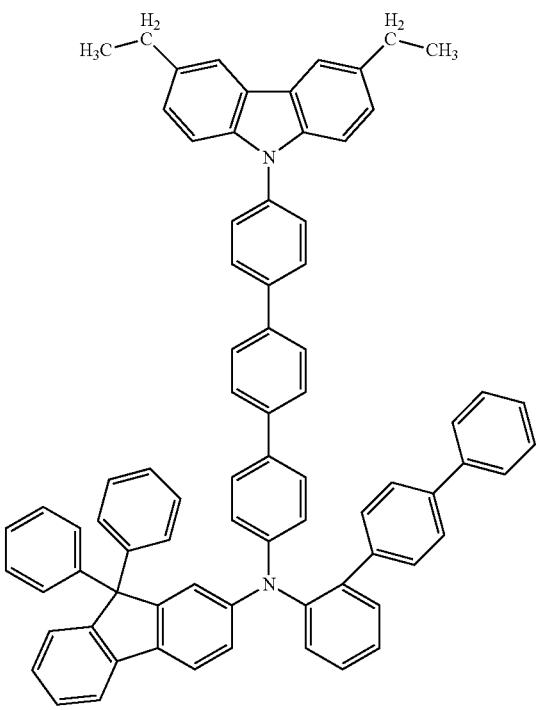
(128)
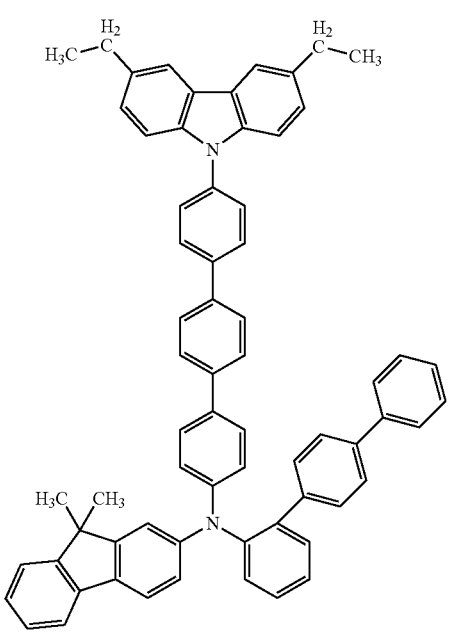
(127)
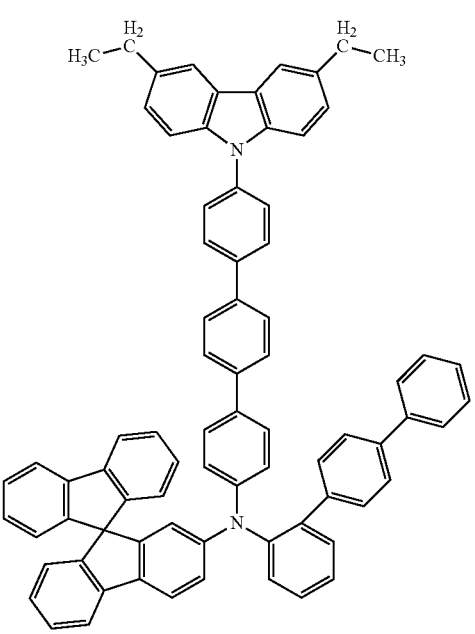
(129)

[Chemical Formula 9]
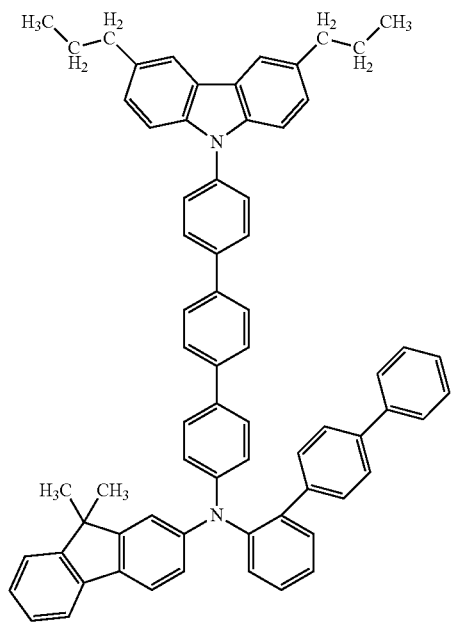
(130)
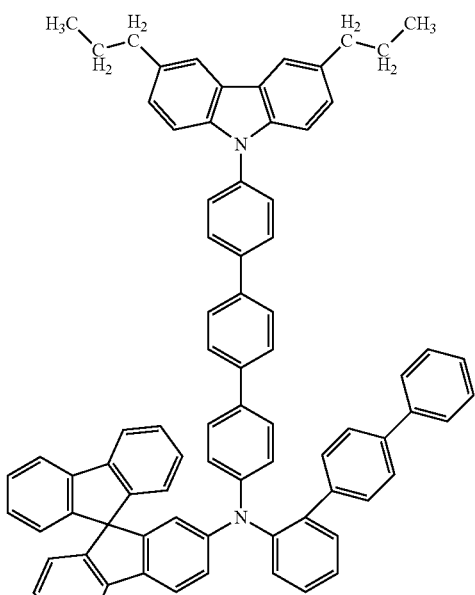
(132)
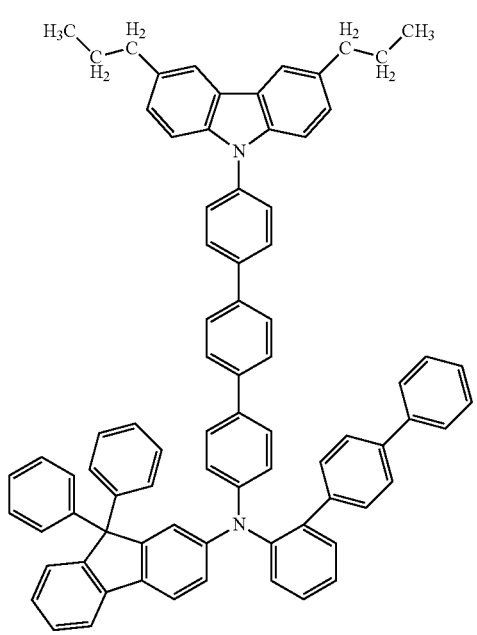
(131)
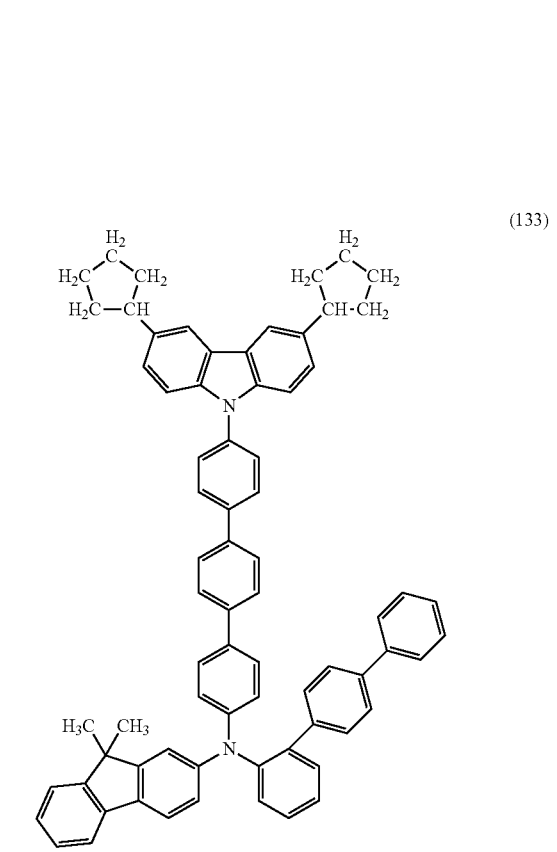
(133)

(134)
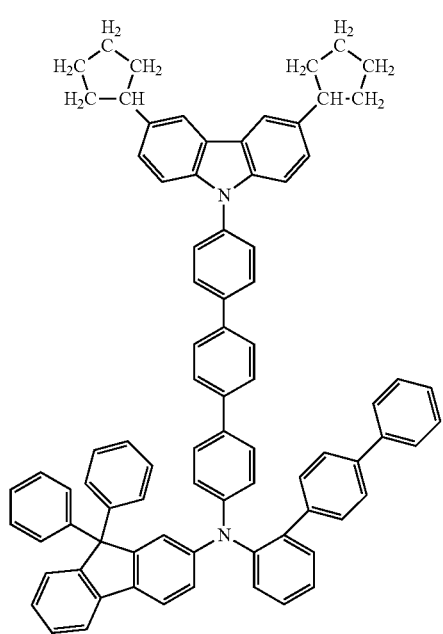
(135)
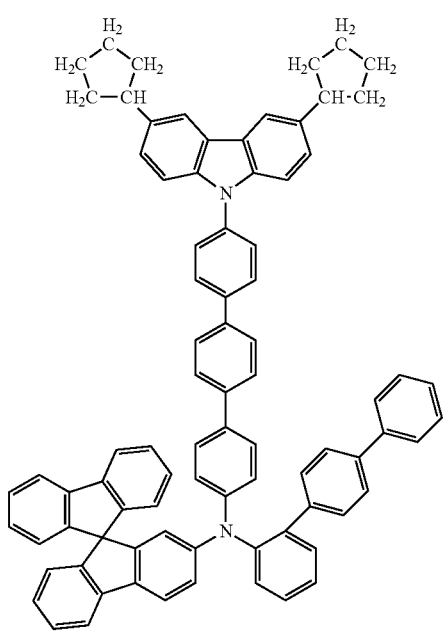
[Chemical Formula 10]
(136)
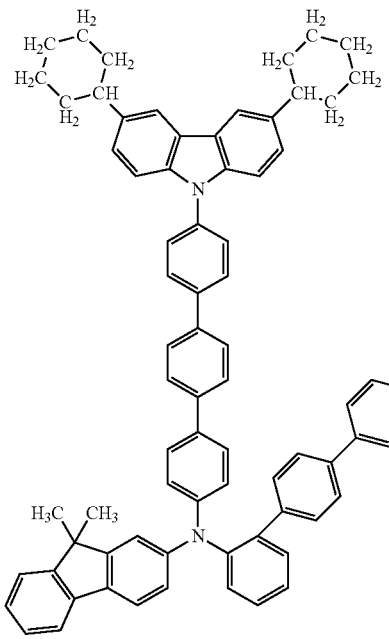
(137)
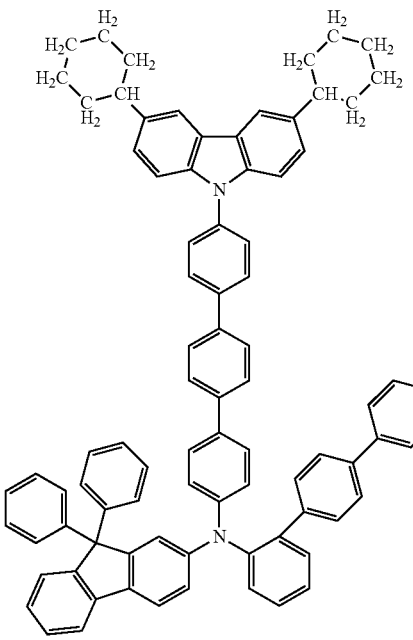

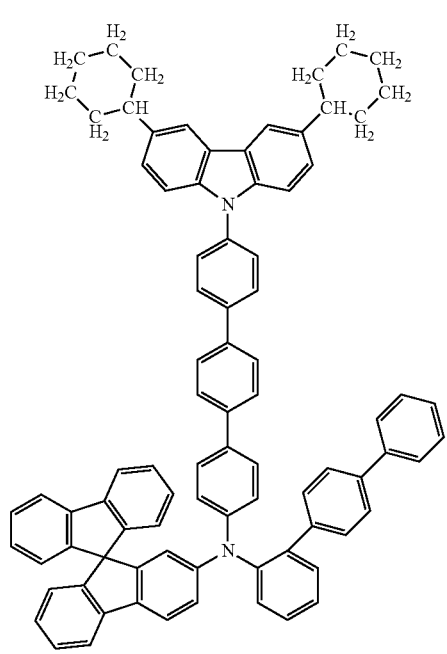
(138)
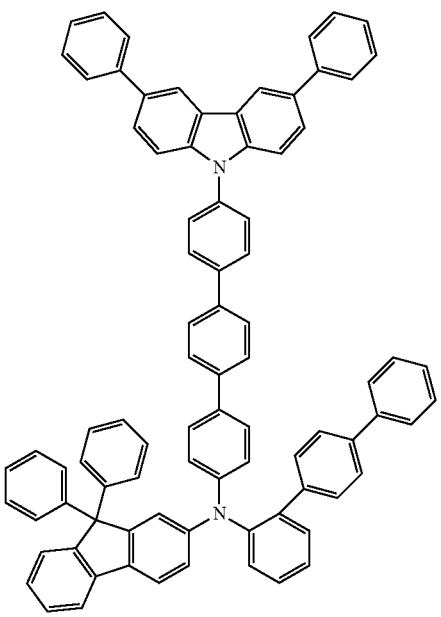
(140)
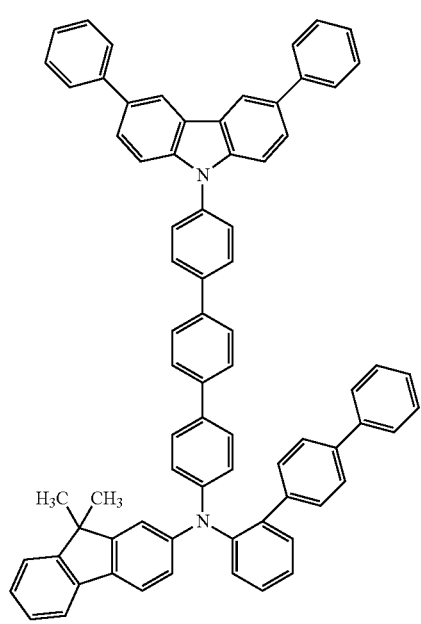
(139)
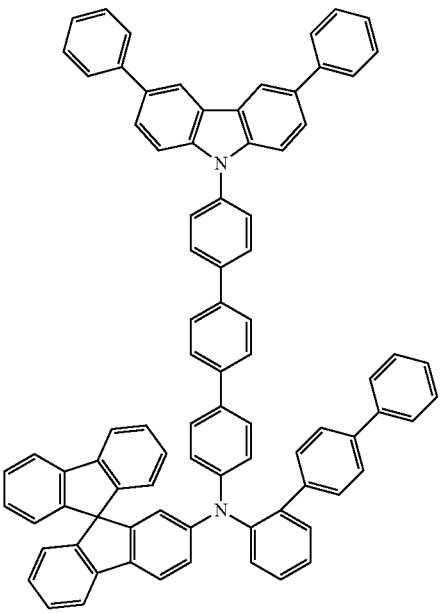
(141)

[Chemical Formula 11]
(142)
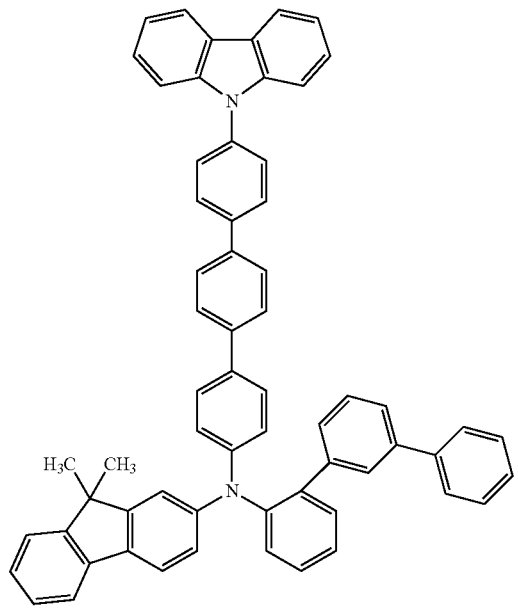
(143)
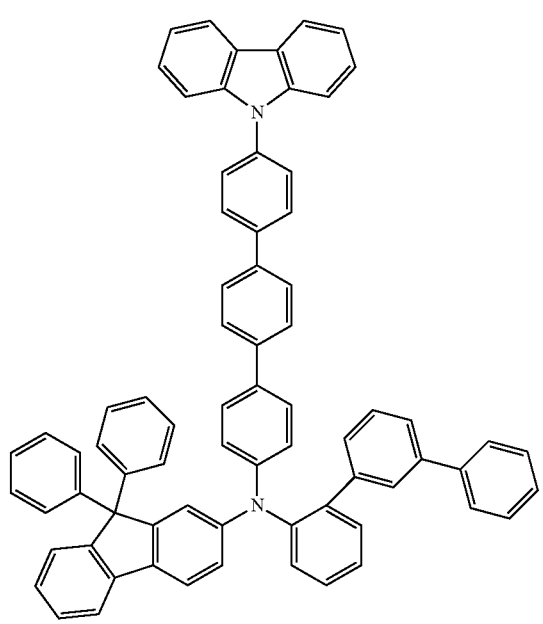
(144)
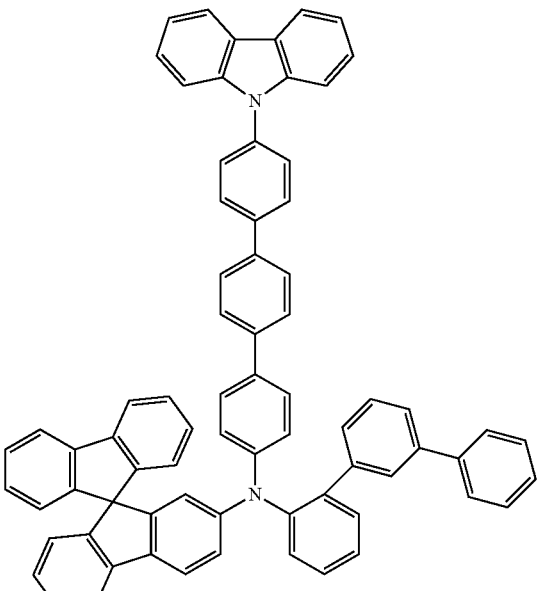
(145)
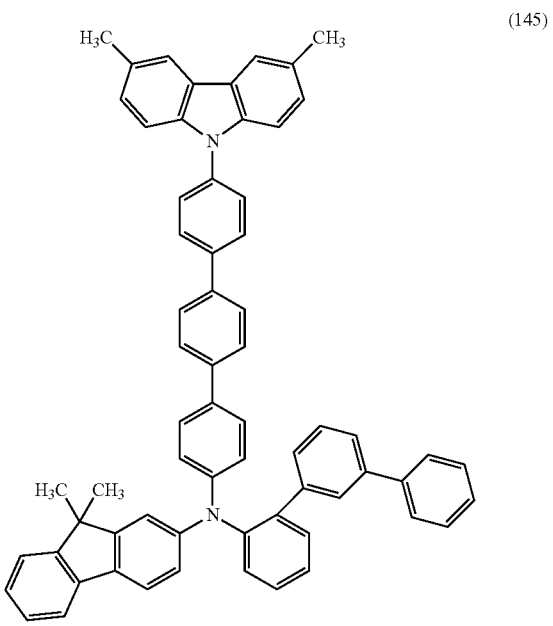

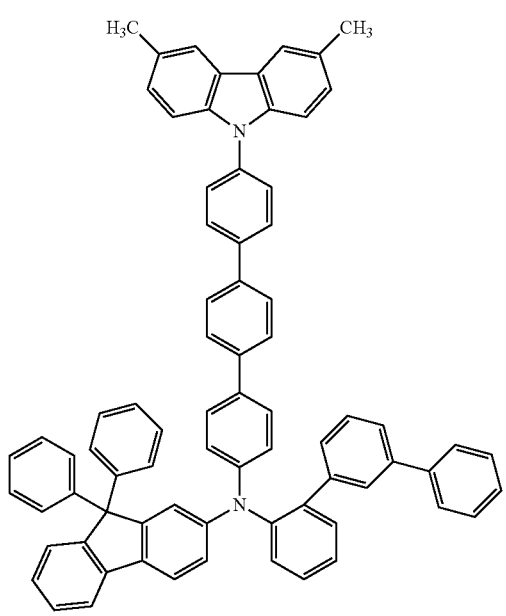
(146)
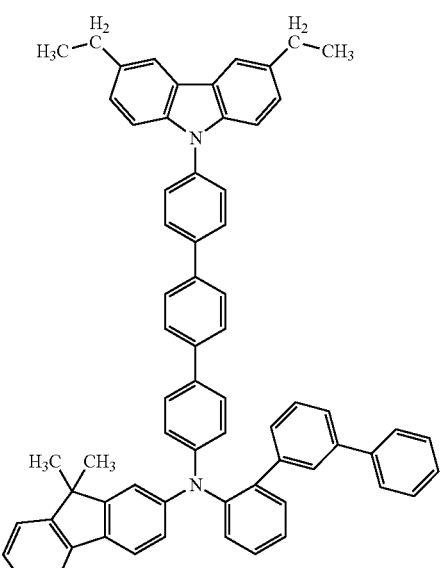
(148)
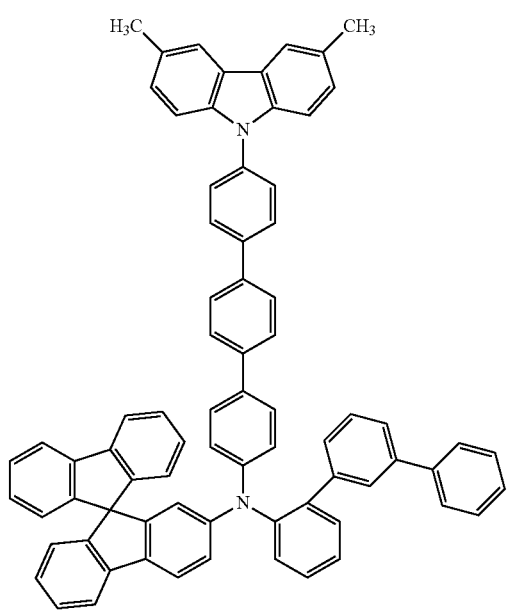
(147)
[Chemical Formula 12]
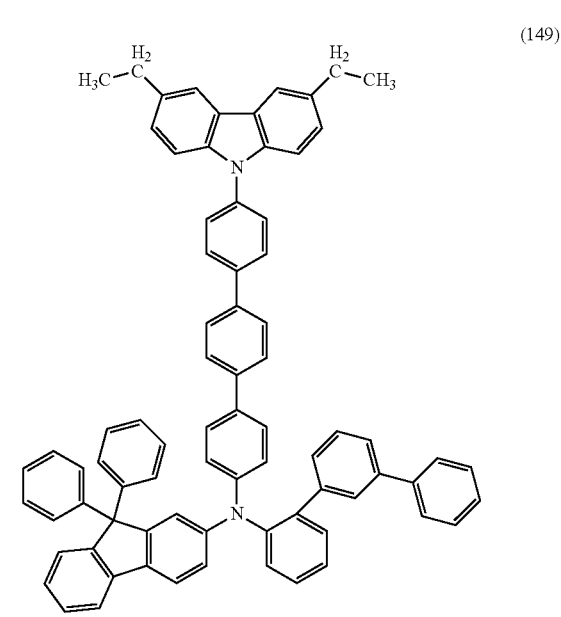
(149)

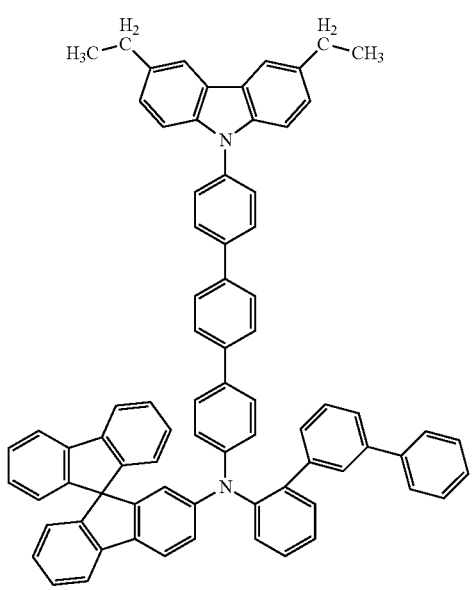
(150)
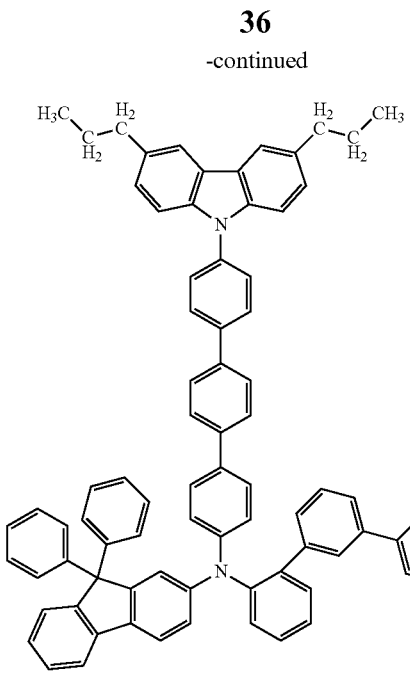
(152)
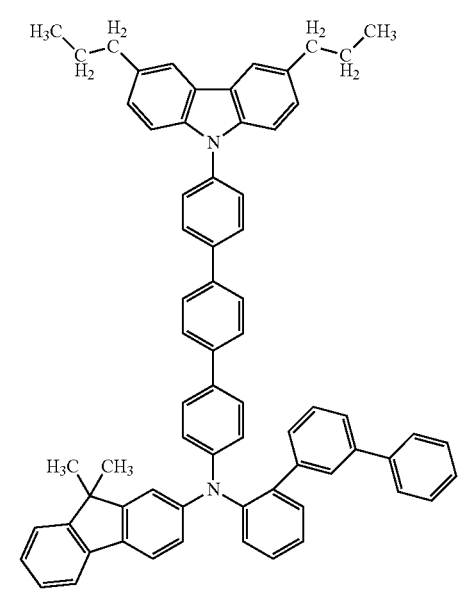
(151)
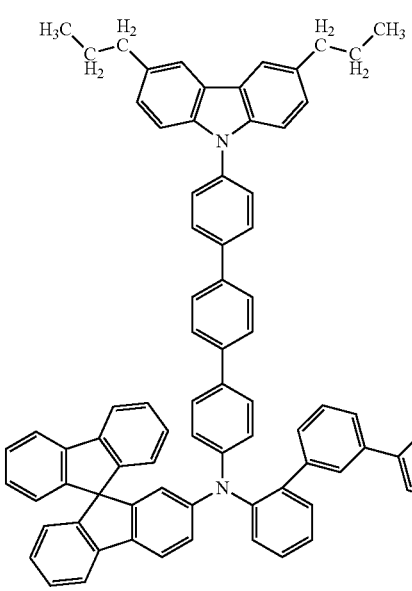
(153)

(154)
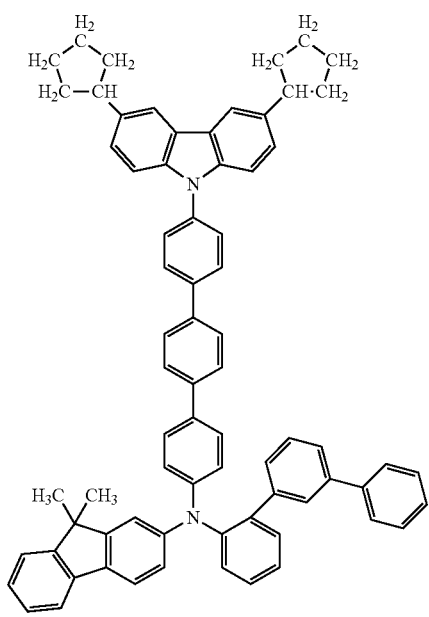
[Chemical Formula 13]
(155)
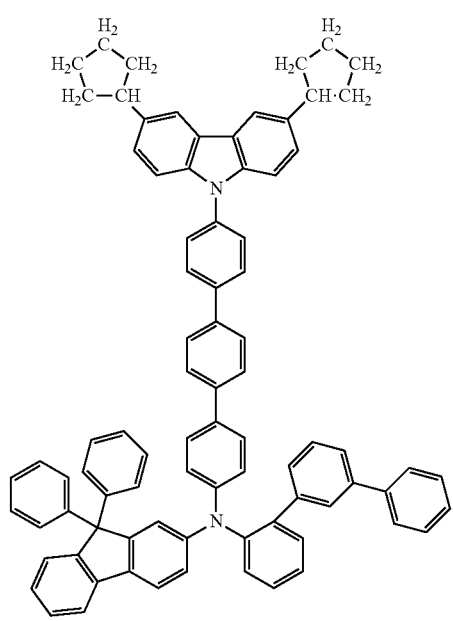
(156)
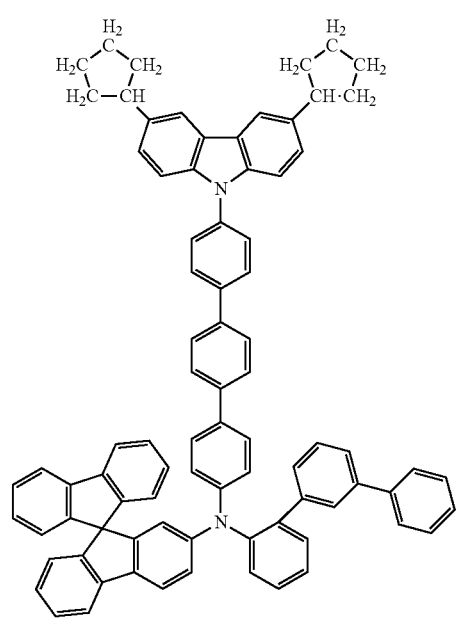
(157)
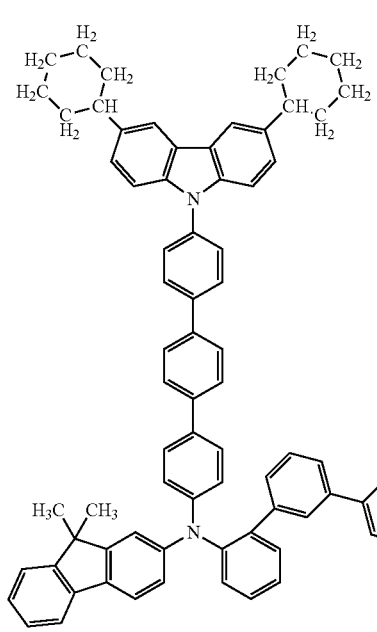

(158)
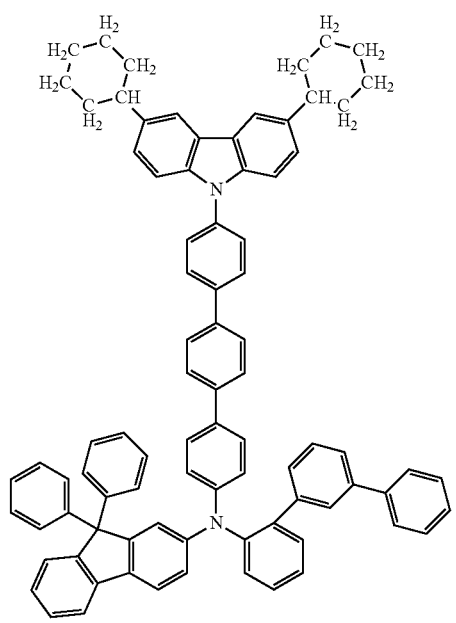
[Chemical Formula 14]
(160)
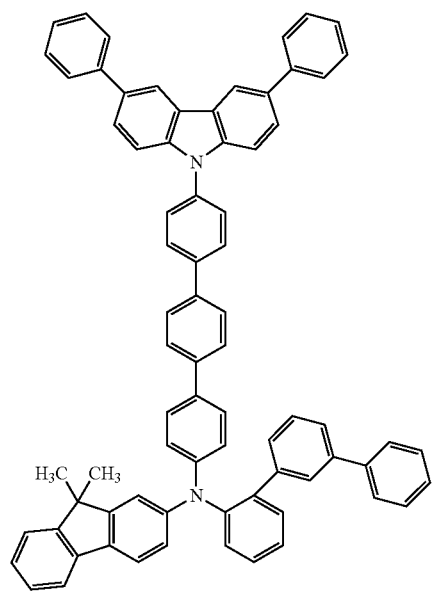
(159)
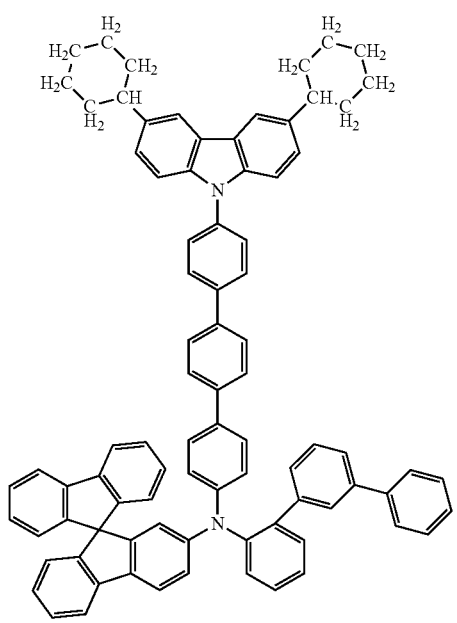
(161)
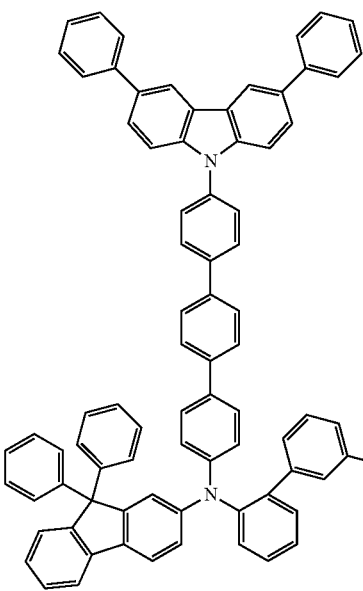

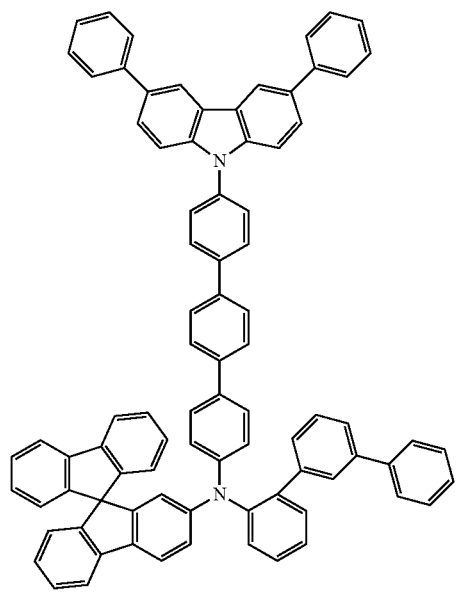
(162)
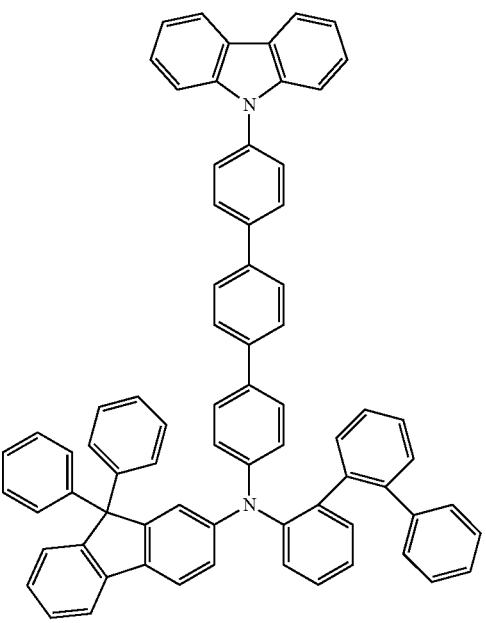
(164)
[Chemical Formula 15]
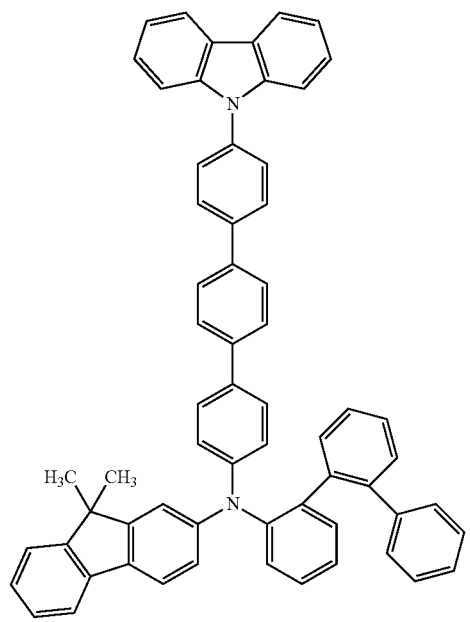
(163)
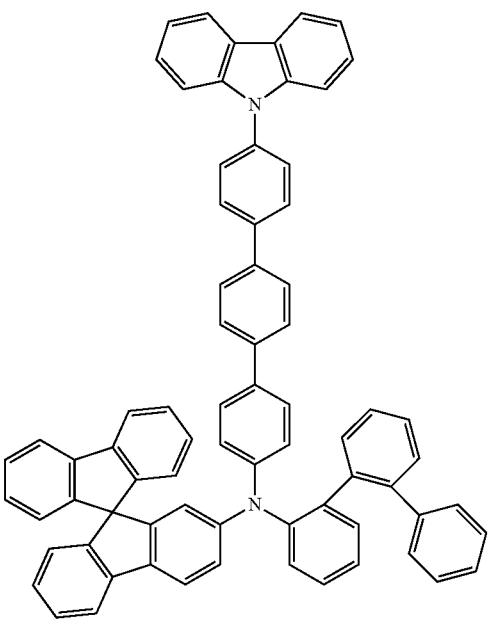
(165)

-continued
(166)
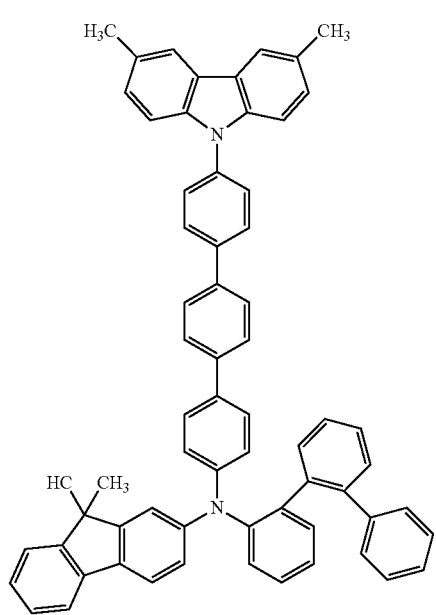
(168)
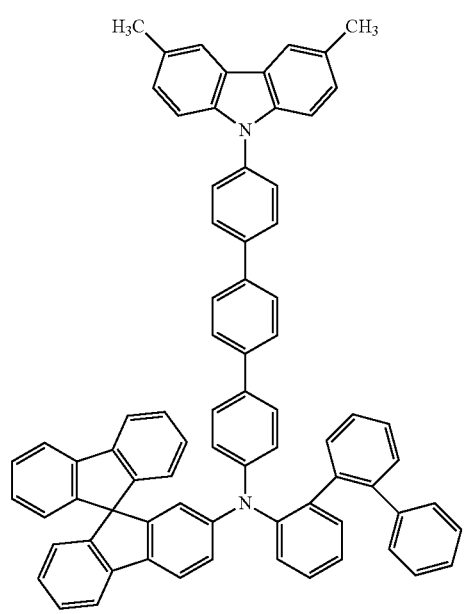
(167)
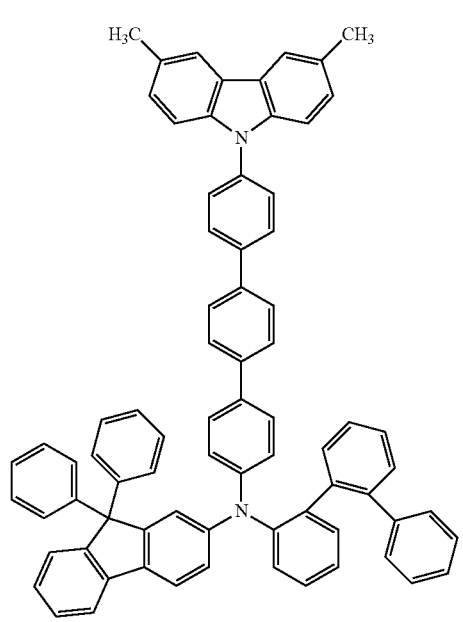
(169)
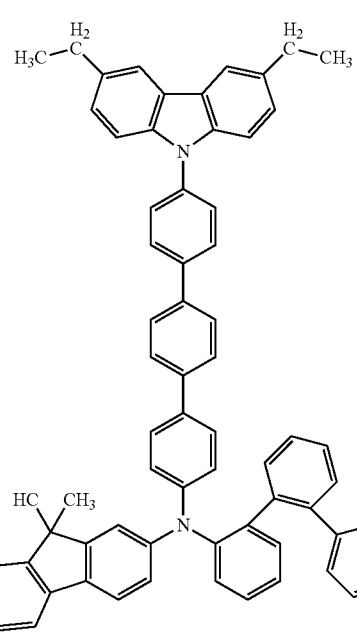

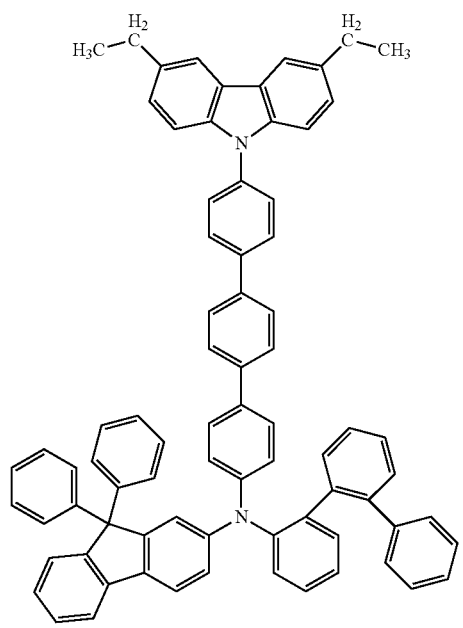
(170)
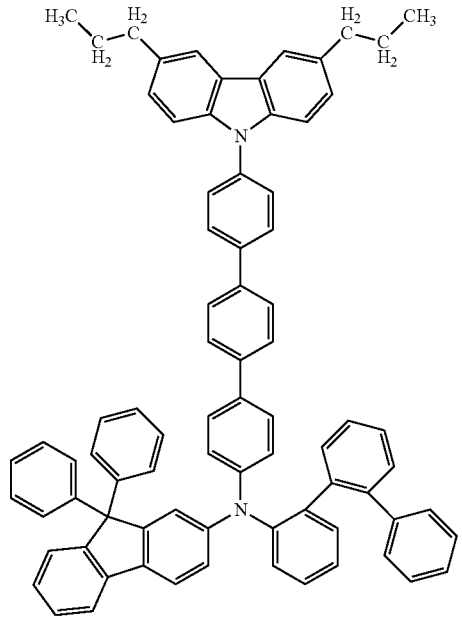
(172)
[Chemical Formula 16]
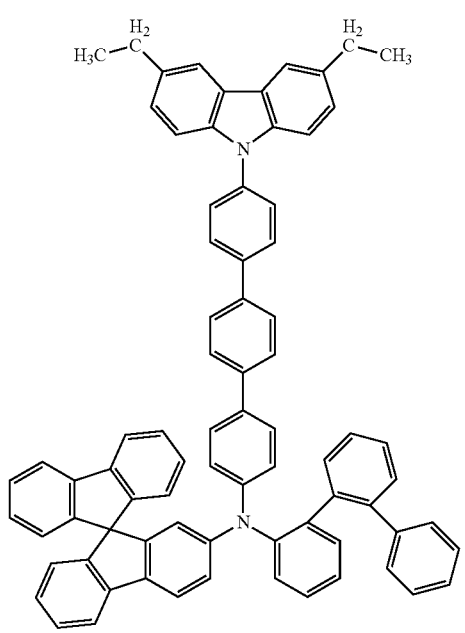
(171)
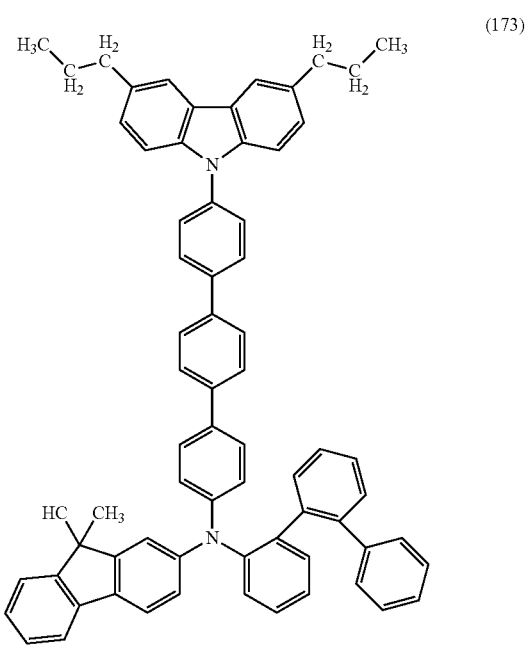
(173)

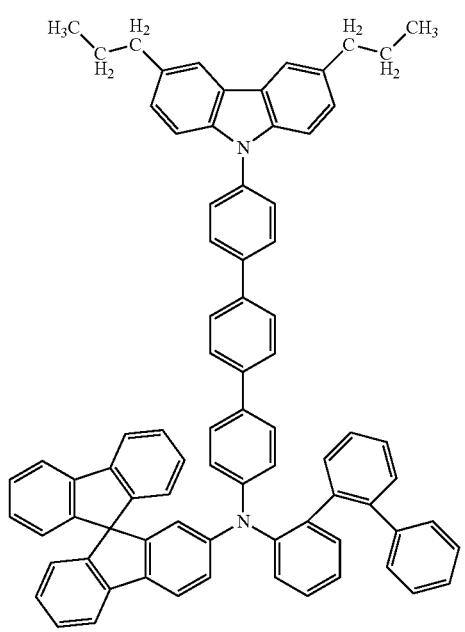
(174)
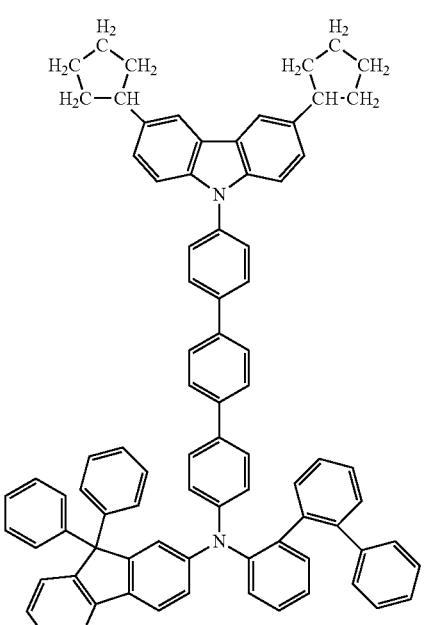
(176)
[Chemical Formula 17]
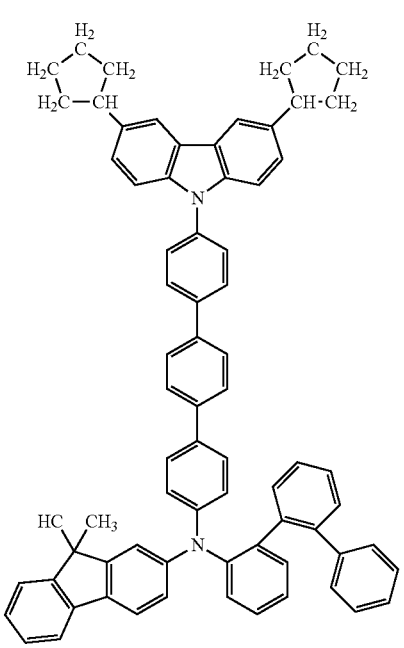
(175)
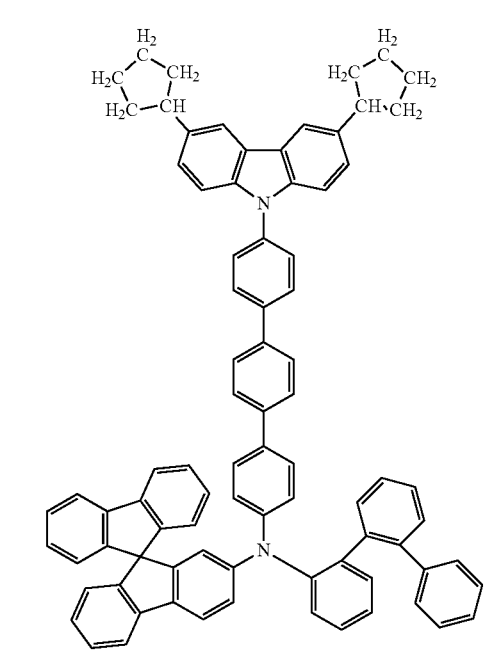
(177)

49
(178)
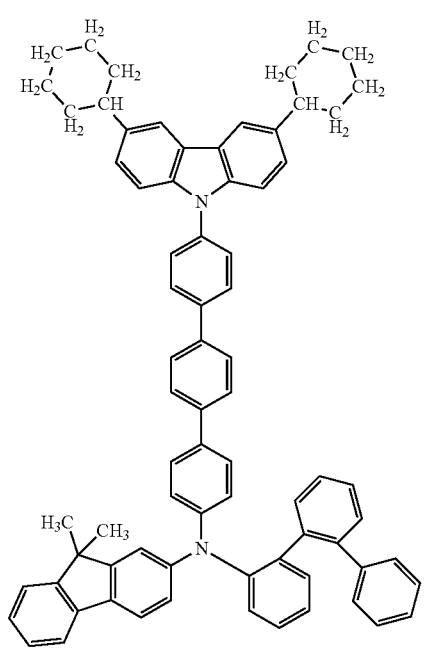
(179)
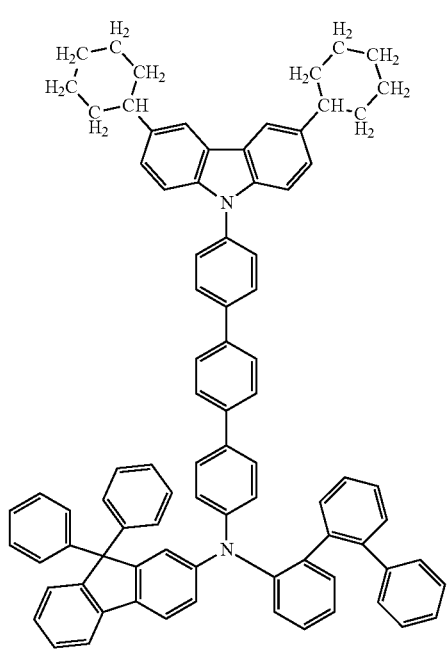
50
(180)
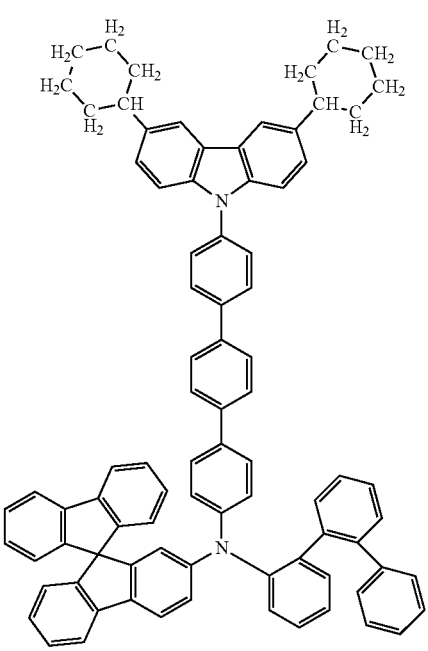
(181)
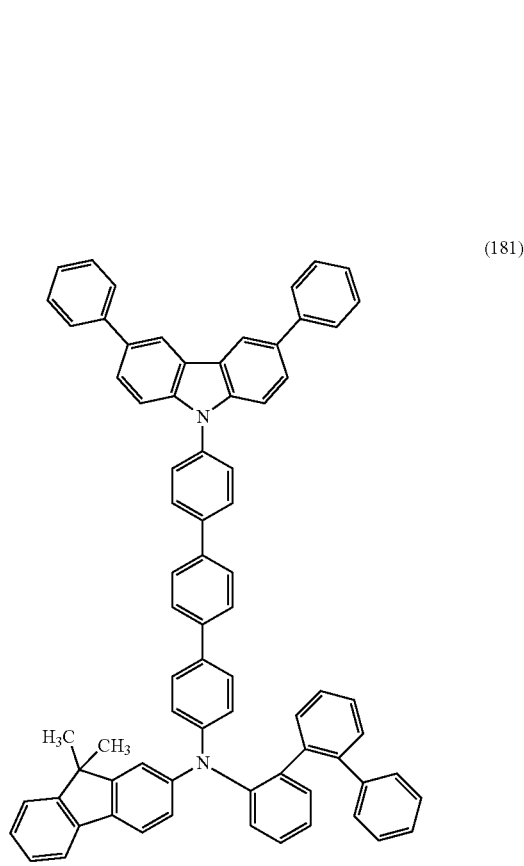

[Chemical Formula 18]
(182)
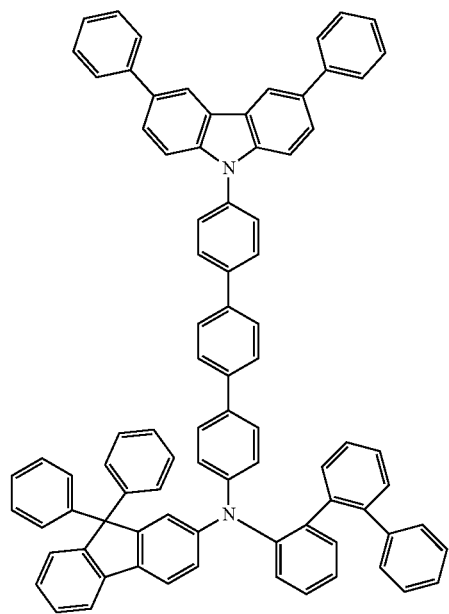
(183)
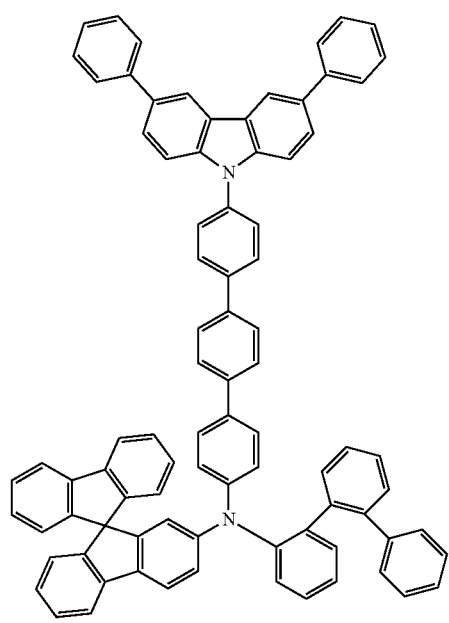
(184)
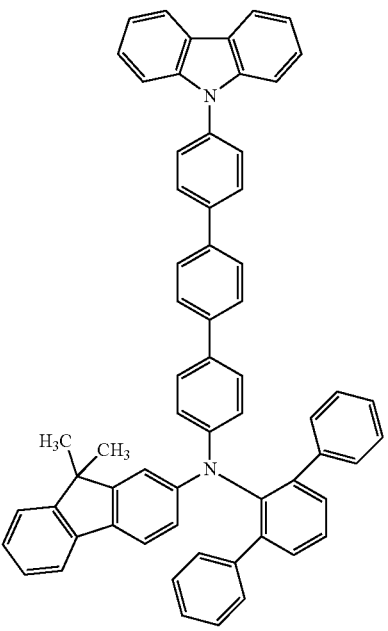
(185)
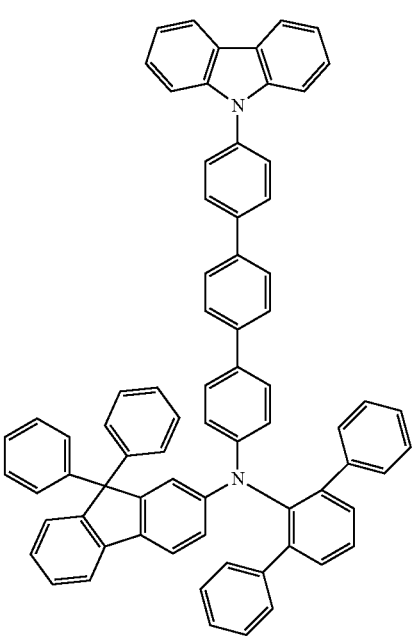

(186)
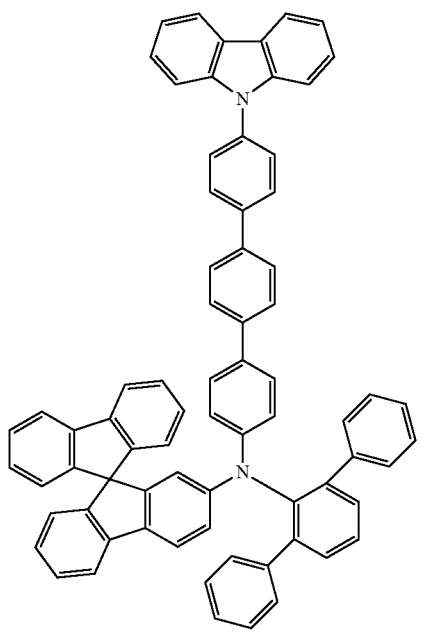
(188)
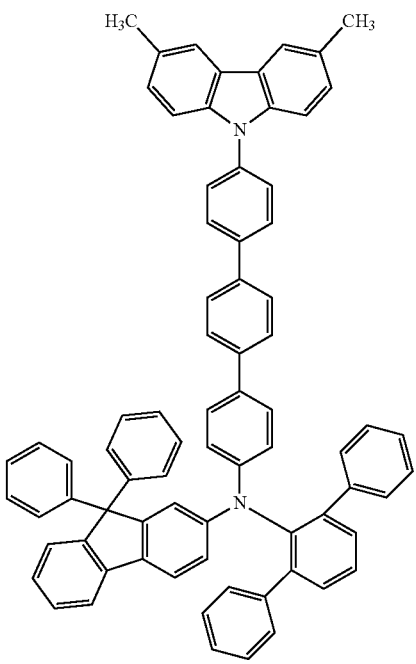
(187)
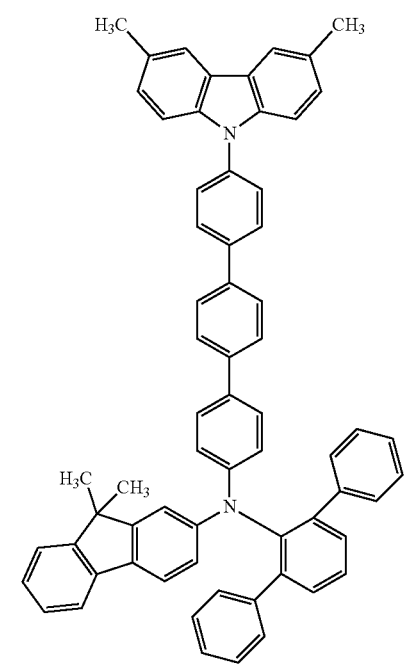
(189)
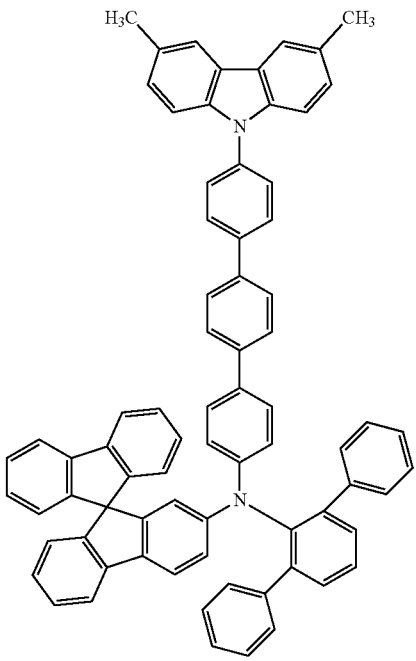

[Chemical Formula 19]
(190)
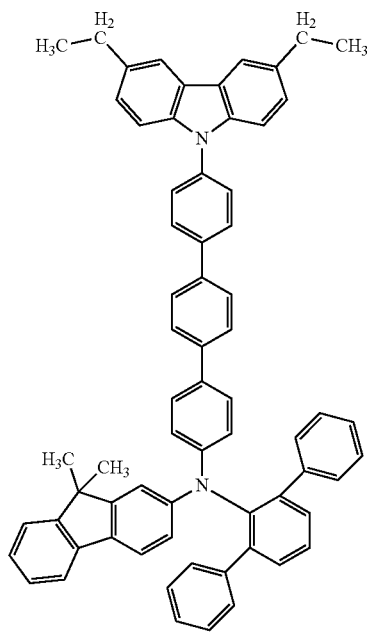
(191)
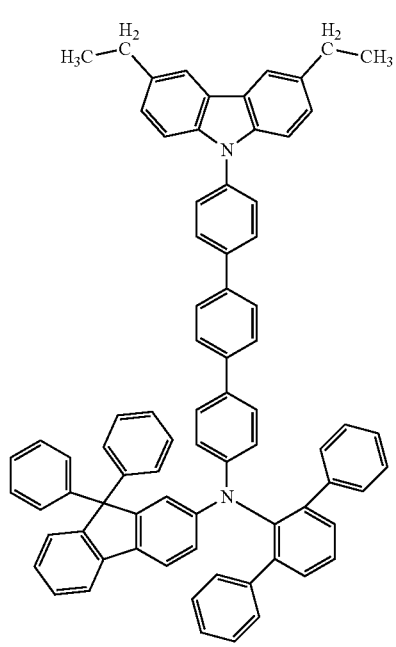
(192)
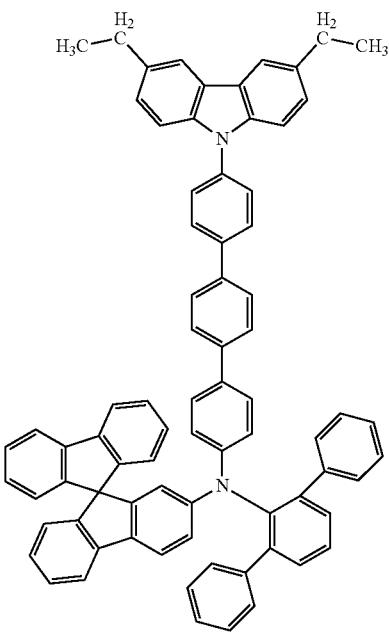
(193)
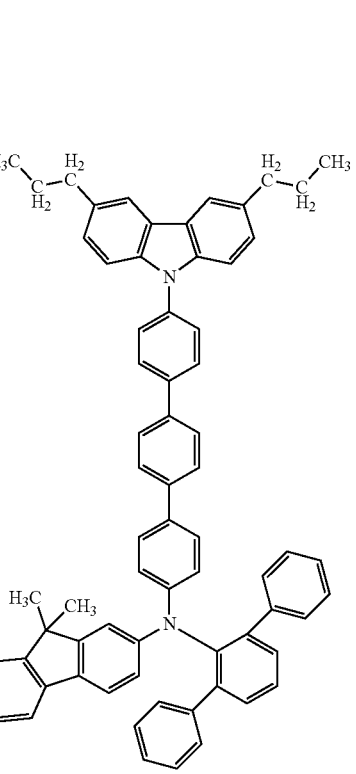

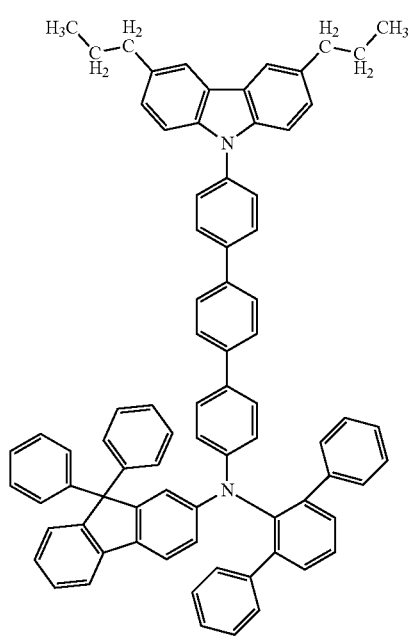
(194)
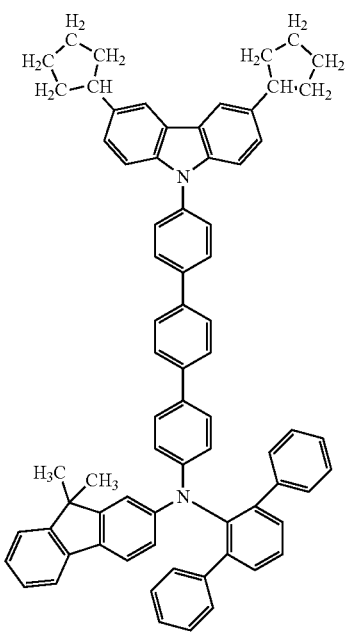
(196)
[Chemical Formula 20]
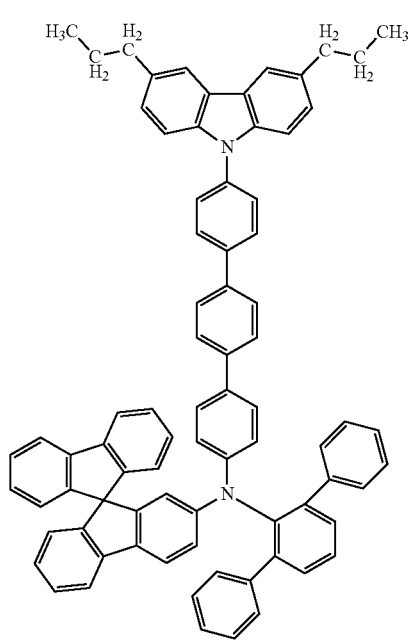
(195)
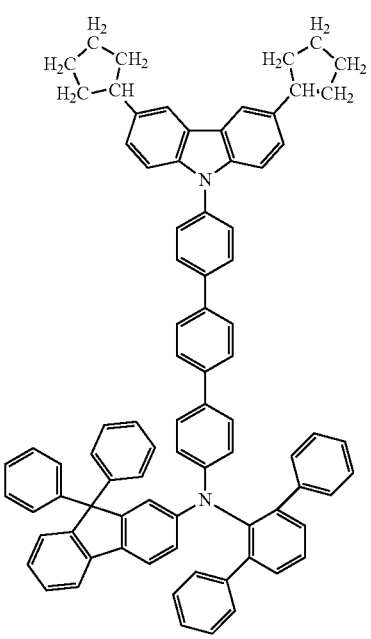
(197)

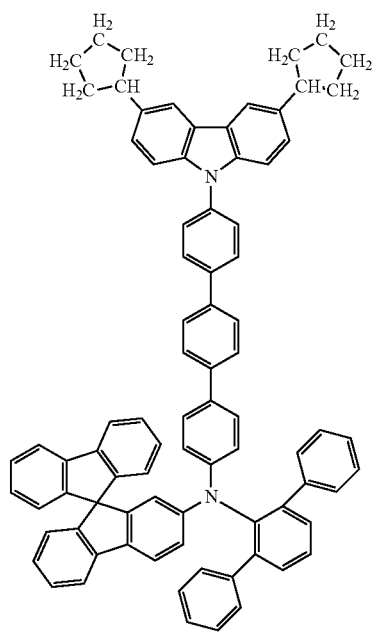 (198)
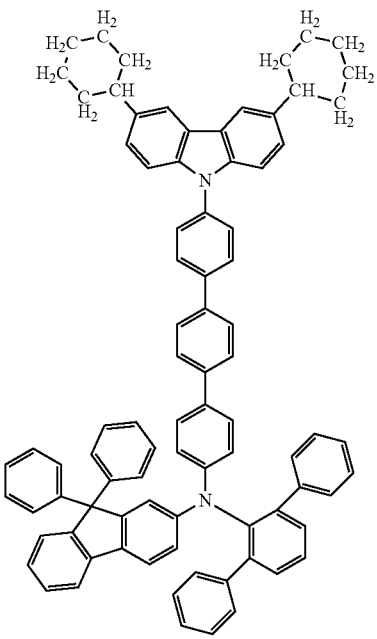 (200)
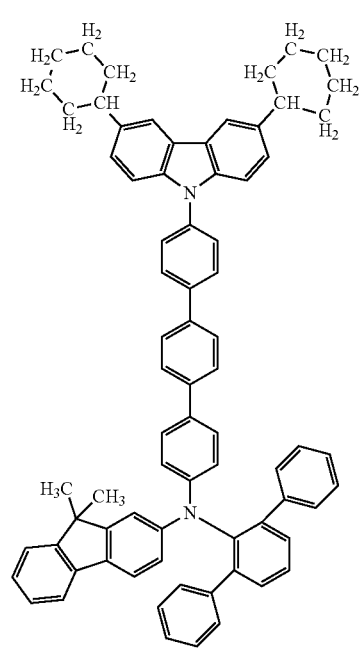 (199)
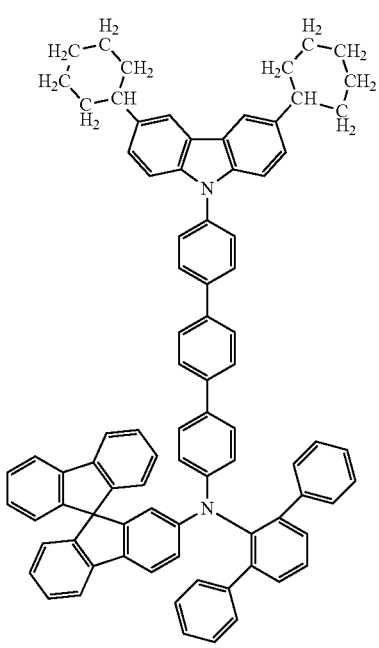 (201)

[Chemical Formula 21]
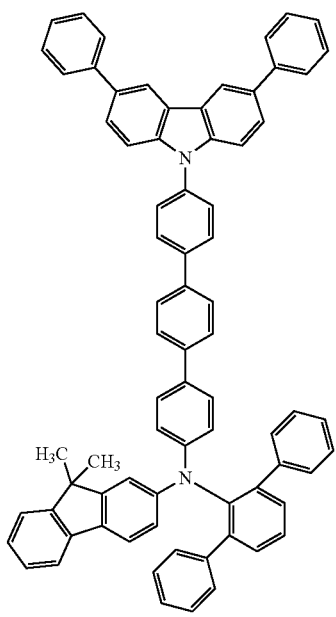
(202)
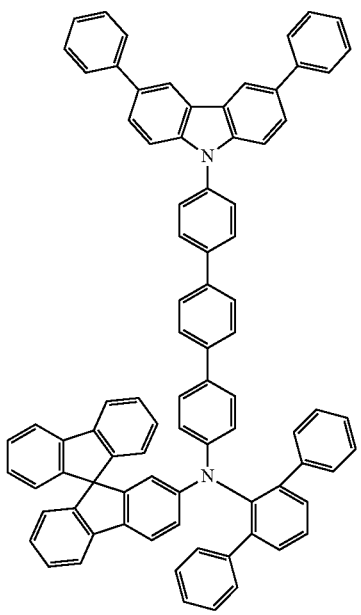
(204)
[Chemical Formula 22]
(203)
(205)

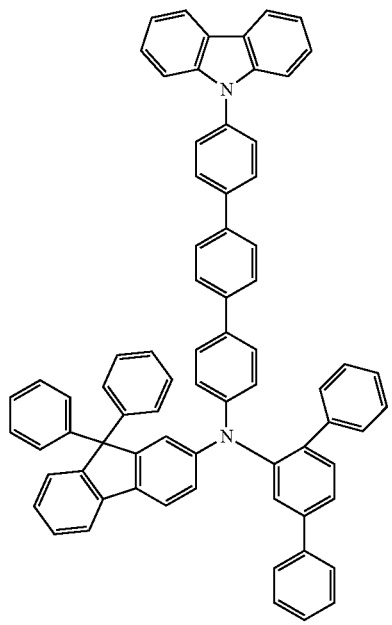
(206)
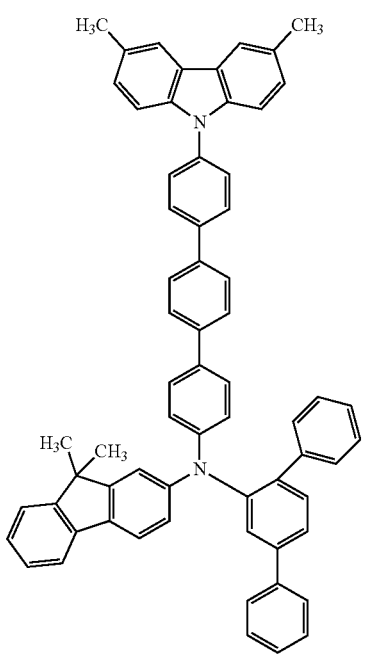
(208)
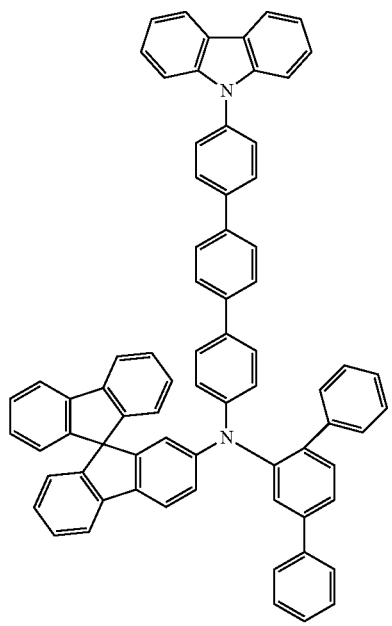
(207)
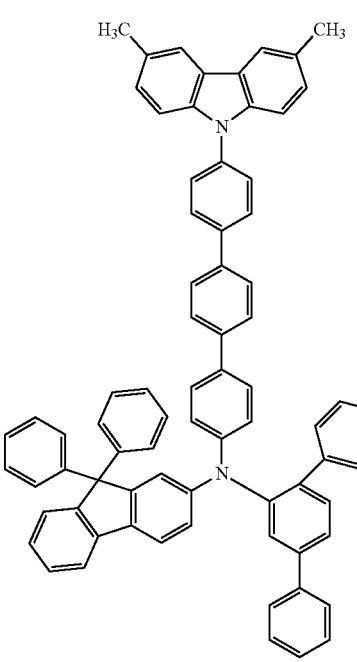
(209)

-continued
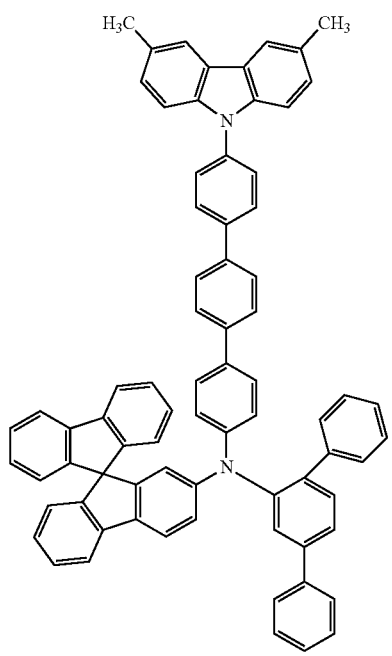
(210)
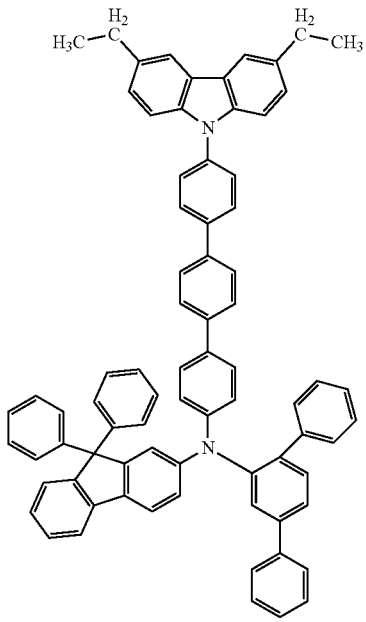
(212)
[Chemical Formula 23]
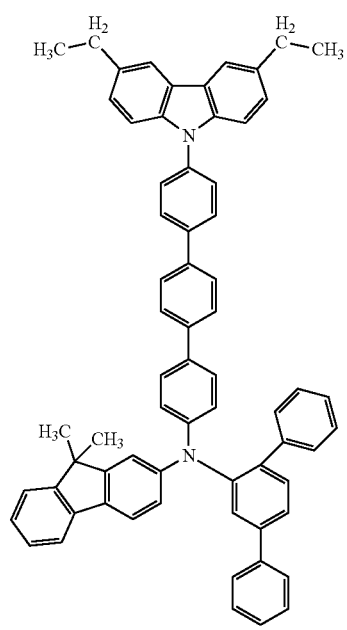
(211)
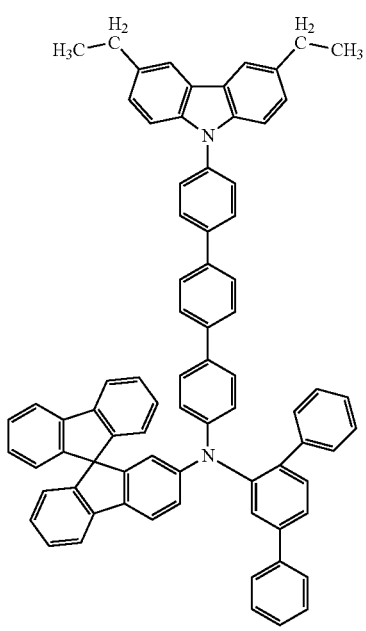
(213)

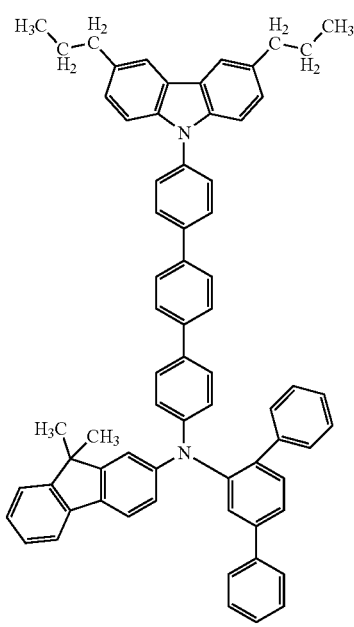
(214)
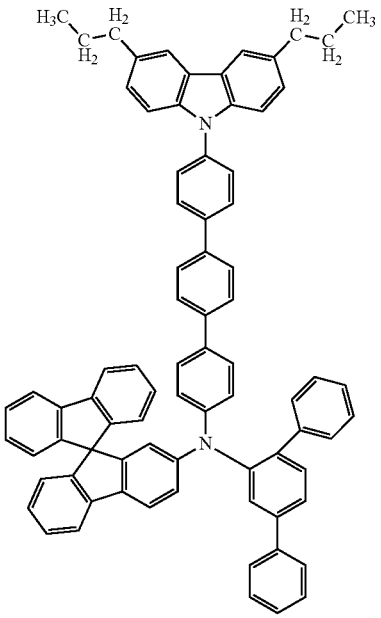
(216)
[Chemical Formula 24]
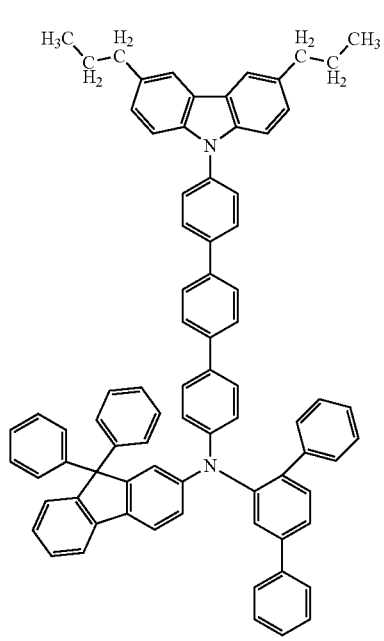
(215)
(217)

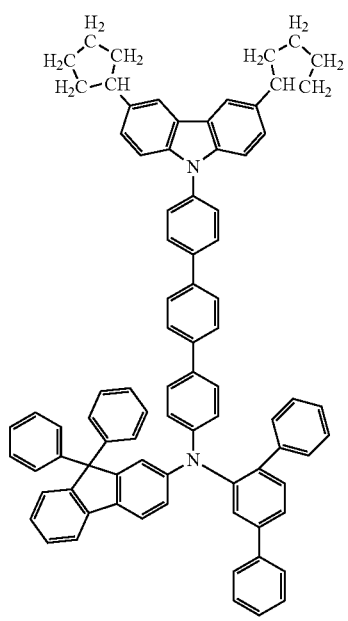# (218)
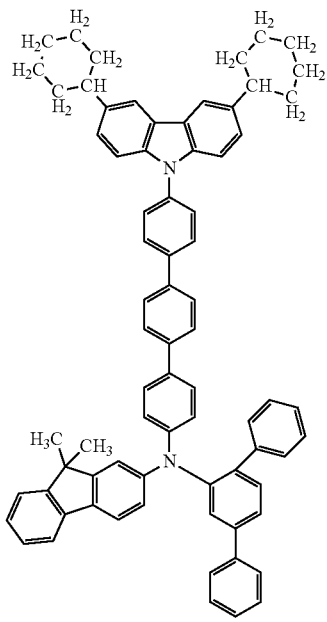# (220)
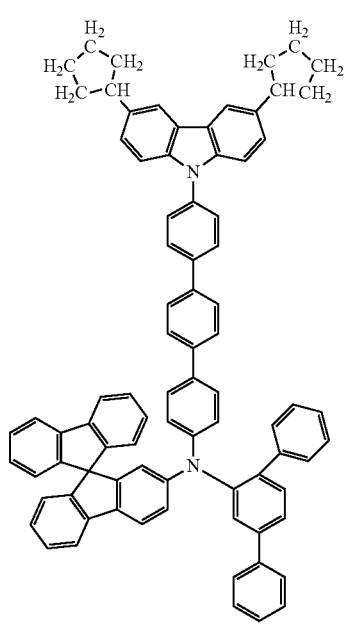# (219)
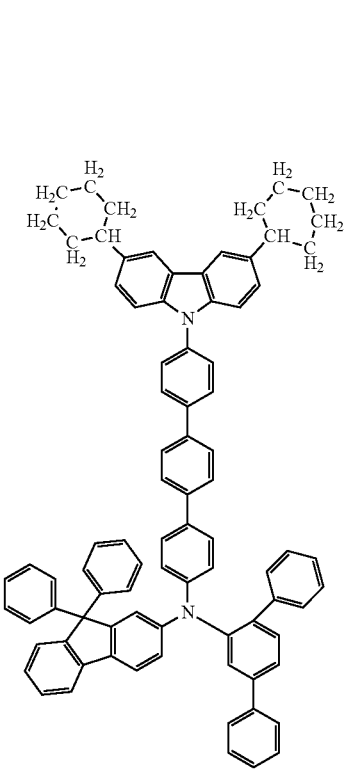# (221)

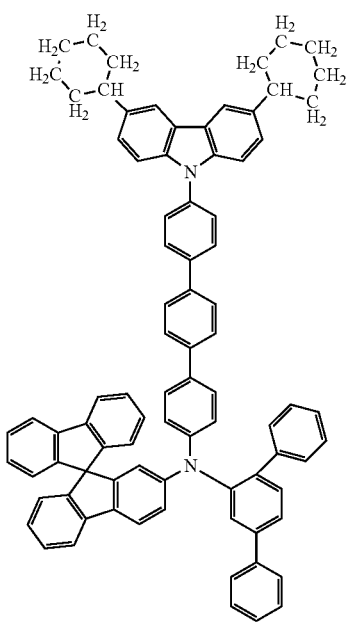
(222)
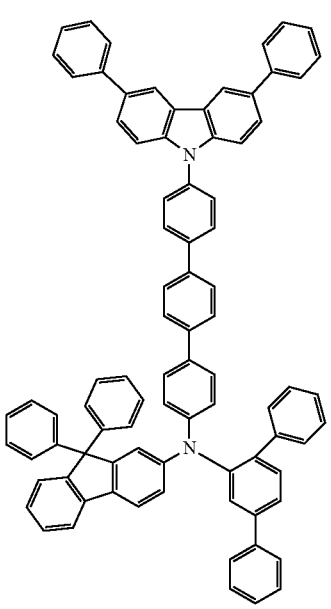
(224)
[Chemical Formula 25]
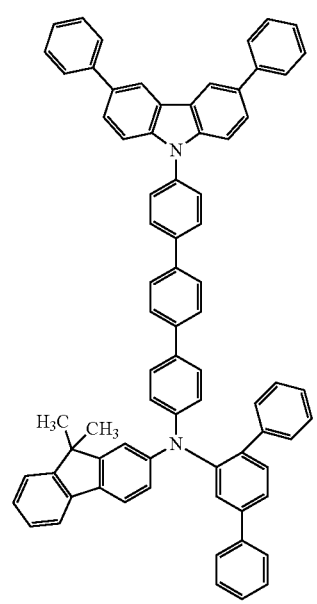
(223)
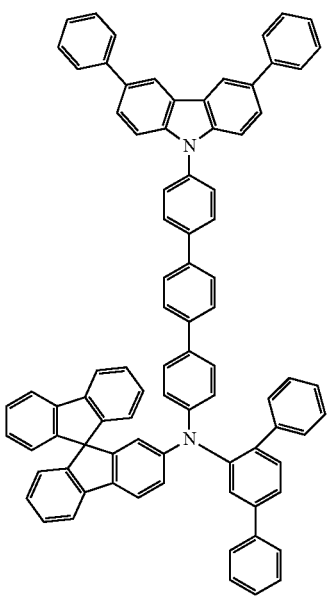
(225)

[Chemical Formula 26]
(226)
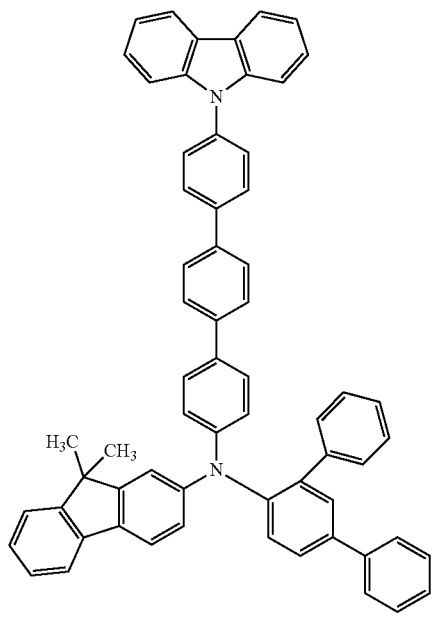
(227)
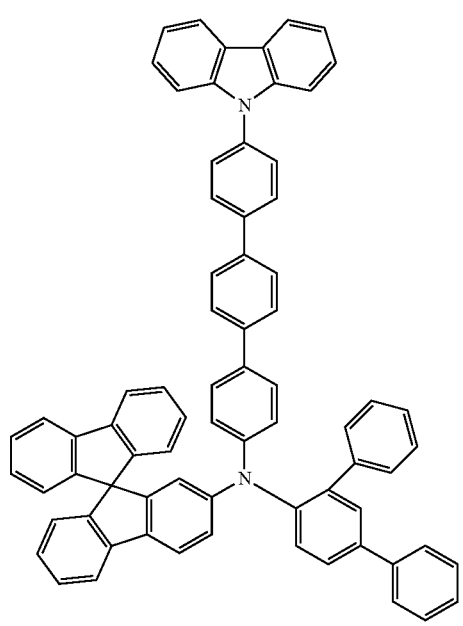
(228)
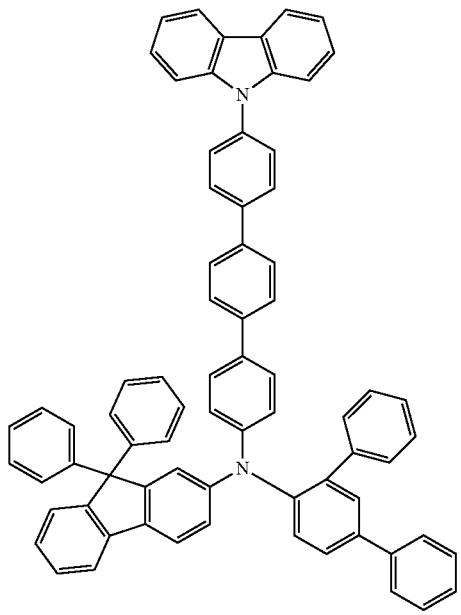
(229)
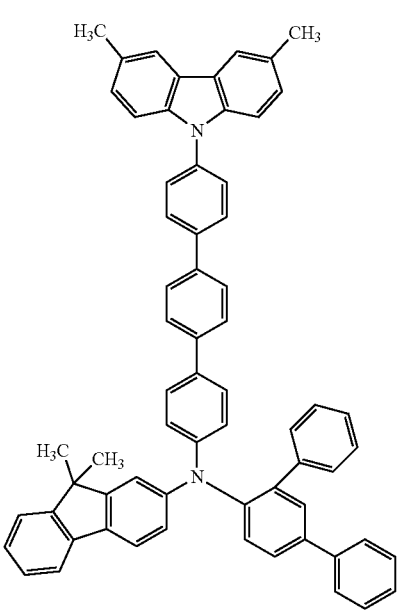

[Chemical Formula 27]
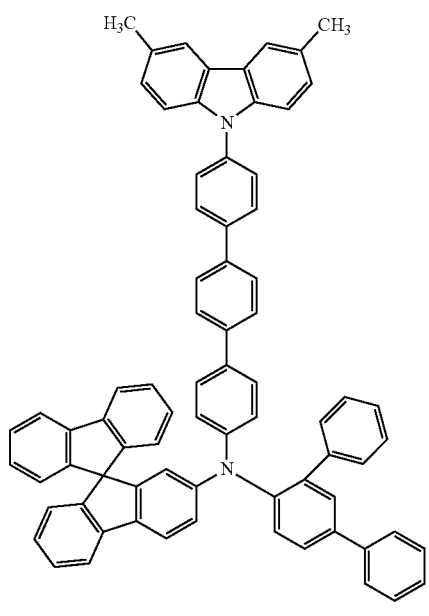
(230)
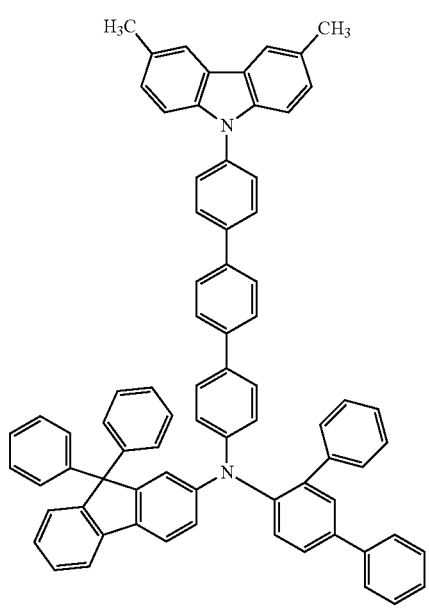
(231)
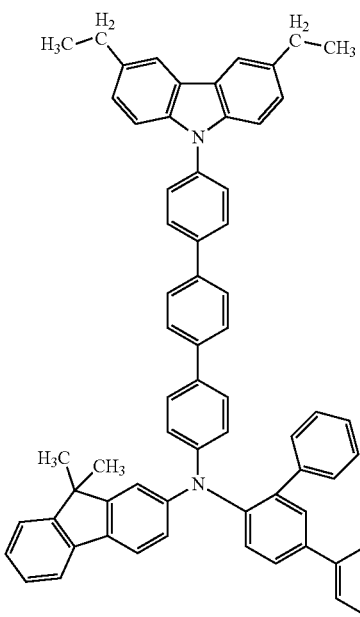
(232)
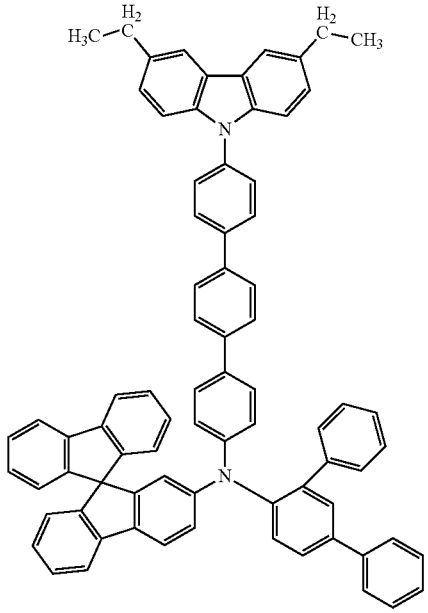
(233)

77
-continued
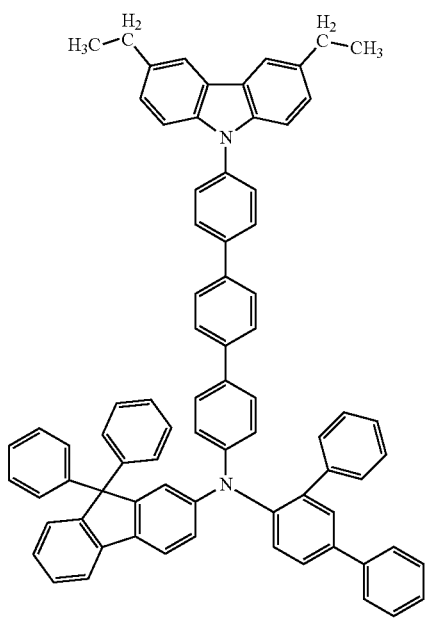
(234)
78
-continued
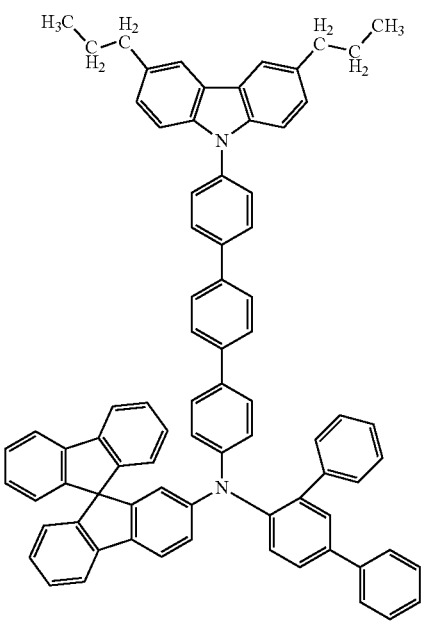
(236)
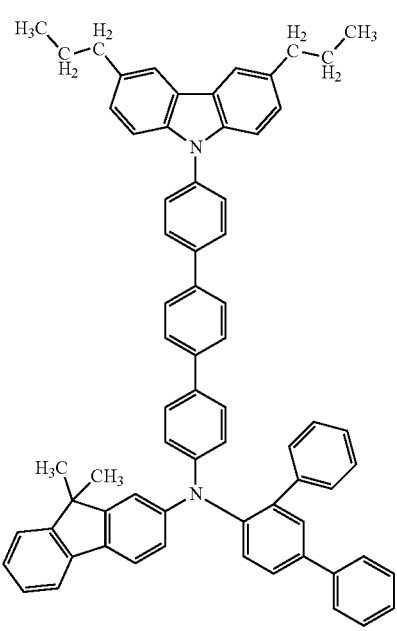
(235)
(237)

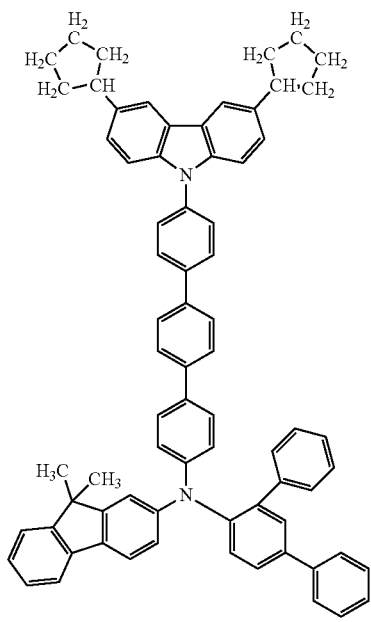
(238)
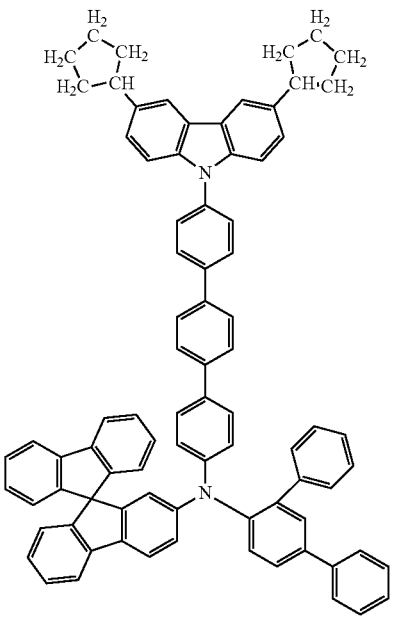
(240)
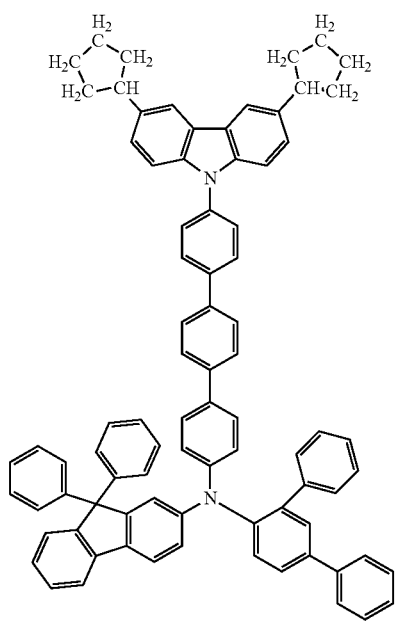
(239)
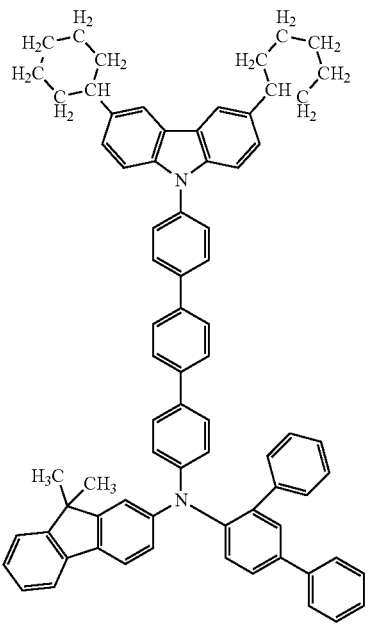
(241)

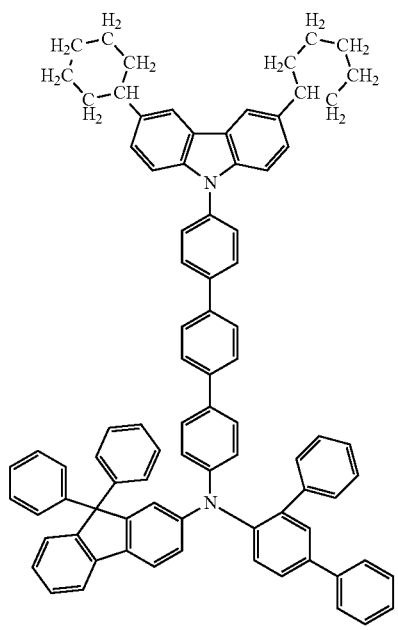
(242)
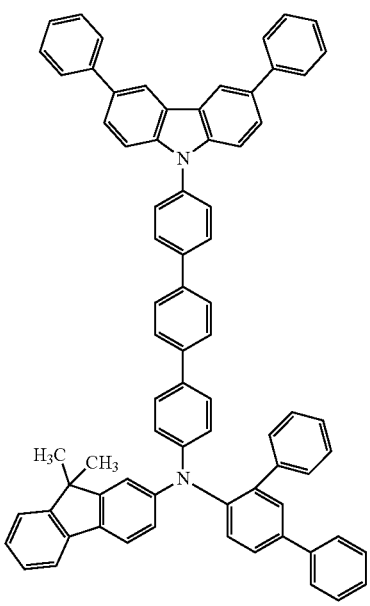
(244)
[Chemical Formula 29]
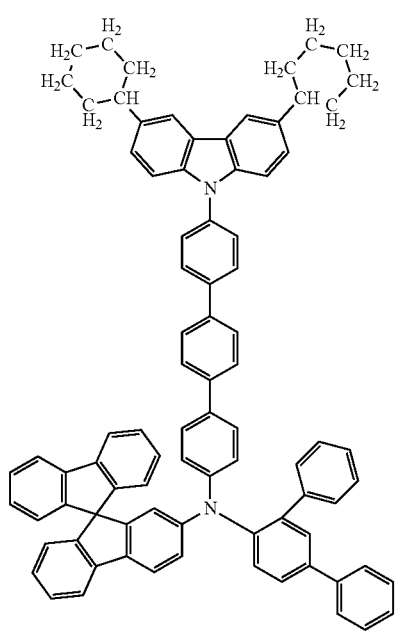
(243)
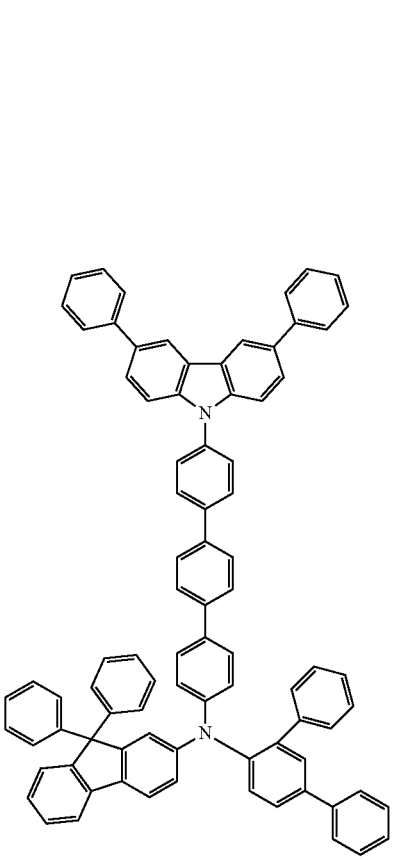
(245)

(246)

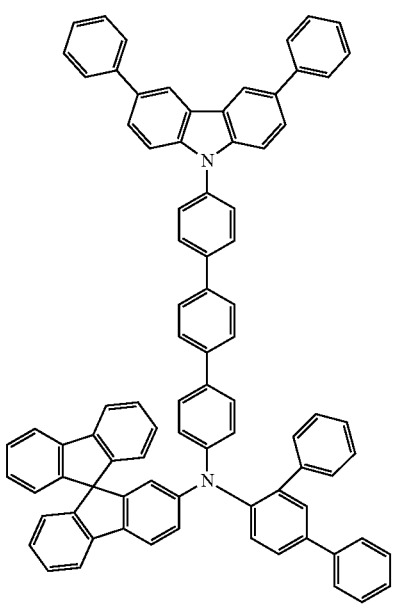

[Synthesis Method of Organic Compound of One Embodiment of the Present Invention]

A variety of reactions can be applied to a synthesis method of an organic compound of one embodiment of the present invention. As an example, a method of synthesizing the organic compound represented by General Formula (G0) is shown below. An example of a method for synthesizing the organic compound represented by General Formula (G1) is described below.

[Chemical Formula 30]

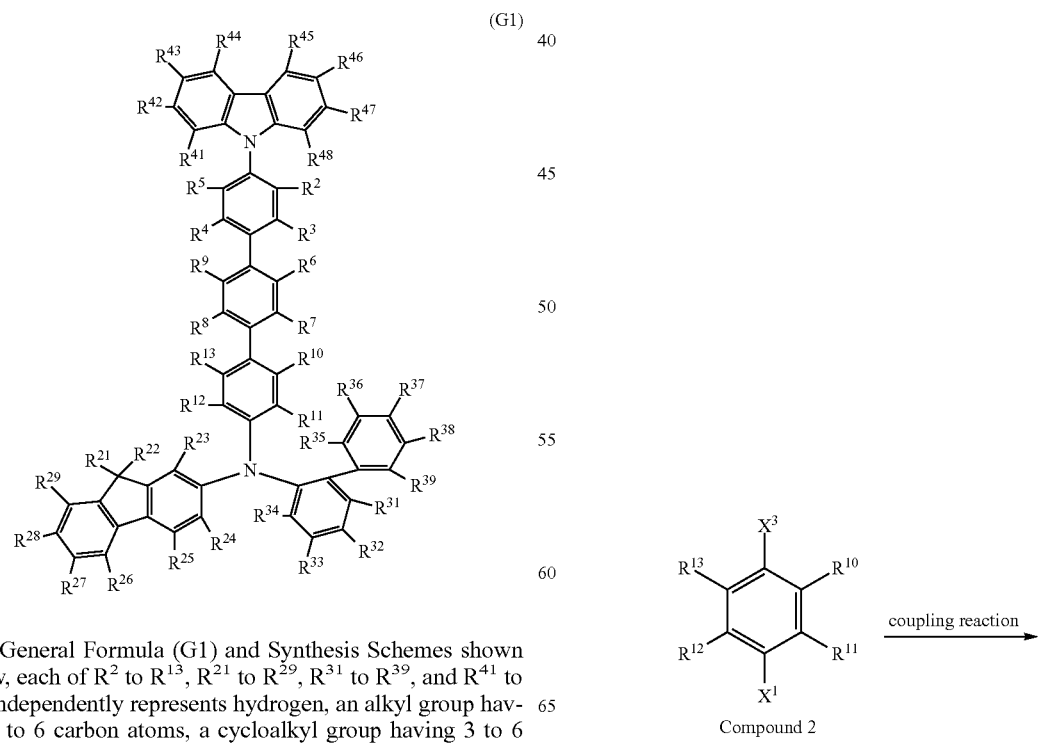

(G1)

In General Formula (G1) and Synthesis Schemes shown below, each of $R^2$ to $R^{13}$, $R^{21}$ to $R^{29}$, $R^{31}$ to $R^{39}$, and $R^{41}$ to $R^{48}$ independently represents hydrogen, an alkyl group having 1 to 6 carbon atoms, a cycloalkyl group having 3 to 6 carbon atoms, or a substituted or unsubstituted aryl group having 6 to 13 carbon atoms. Furthermore, $R^{21}$ and $R^{22}$ may be bonded to each other to form a spiro ring.

<<Synthesis Method 1 of Organic Compound Represented by General Formula (G1)>>

The organic compound represented by General Formula (G1) can be synthesized through Synthesis Scheme (a-1) or Synthesis Scheme (a-2) and Synthesis Scheme (a-3).

First, as shown in Synthesis Scheme (a-1), a 9-biphenyl-9H-carbazole compound (Compound 1) and a dihalogenated benzene (Compound 2) are coupled, whereby a halogenated 9-terphenyl-9H-carbazole compound (Compound 3) is obtained.

[Chemical Formula 31]

(a-1)

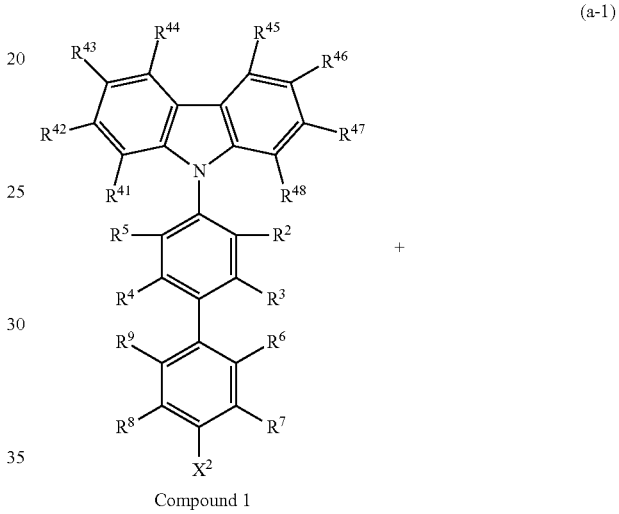

-continued

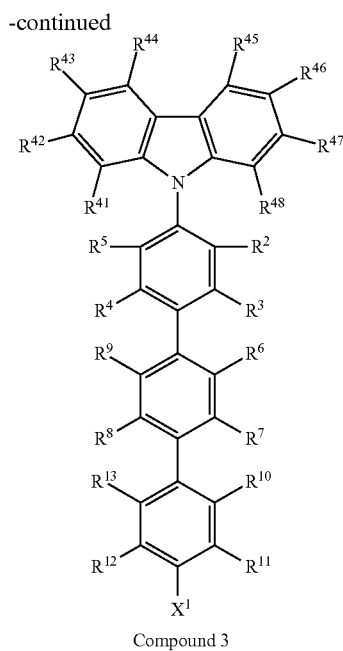

Compound 3

In Synthesis Scheme (a-1), each of $X^1$ to $X^3$ independently represents a halogen, a boronic acid group, an organoboron group, a triflate group, an organotin group, an organozinc group, or a magnesium halide group.

In the case where a Suzuki-Miyaura coupling reaction using a palladium catalyst is performed in Synthesis Scheme (a-1), $X^1$ represents a halogen, one of $X^2$ and $X^3$ represents a boronic acid group or an organoboron group, and the other represents a halogen or a triflate group. As the halogen, iodine, bromine, or chlorine is preferred.

In the reaction, a palladium compound such as bis(dibenzylideneacetone)palladium(0), palladium(II) acetate, [1,1-bis(diphenylphosphino)ferrocene]palladium(II) dichloride, or tetrakis(triphenylphosphine)palladium(0) and a ligand such as tri(tert-butyl)phosphine, tri(n-hexyl)phosphine, tricyclohexylphosphine, di(1-adamantyl)-n-butylphosphine, 2-dicyclohexylphosphino-2',6'-dimethoxybiphenyl, or tri(ortho-tolyl)phosphine can be used. In the reaction, an organic base such as sodium tert-butoxide, an inorganic base such as potassium carbonate, cesium carbonate, or sodium carbonate, or the like can be used.

In the reaction, toluene, xylene, benzene, tetrahydrofuran, dioxane, ethanol, methanol, water, diethylene glycol dimethyl ether, ethylene glycol monomethyl ether, or the like can be used as a solvent. Reagents that can be used for the reaction are not limited to these.

As the reaction represented by Synthesis Scheme (a-1), a Migita-Kosugi-Stille coupling reaction using an organotin compound, a Kumada-Tamao-Corriu coupling reaction using a Grignard reagent, a Negishi coupling reaction using an organozinc compound, an Ullmann reaction using copper or a copper compound, or the like can also be performed.

In the case of employing the Migita-Kosugi-Stille coupling reaction, one of $X^2$ and $X^3$ represents an organotin group and the other represents a halogen. That is, one of Compound 1 and Compound 2 is an organotin compound and the other is a halide.

In the case of employing the Kumada-Tamao-Corriu coupling reaction, one of $X^2$ and $X^3$ represents a magnesium halide group and the other represents a halogen group. That is, one of Compound 1 and Compound 2 is a Grignard reagent and the other is a halide.

In the case of employing the Negishi coupling reaction, one of $X^2$ and $X^3$ represents an organozinc group and the other represents a halogen. That is, one of Compound 1 and Compound 2 is an organozinc compound and the other is a halide.

Alternatively, as shown in Synthesis Scheme (a-2), a 9-phenyl-9H-carbazole compound (Compound 4) and a biphenyl compound (Compound 5) are coupled, whereby a halogenated 9-terphenyl-9H-carbazole compound (Compound 3) is obtained.

[Chemical Formula 32]

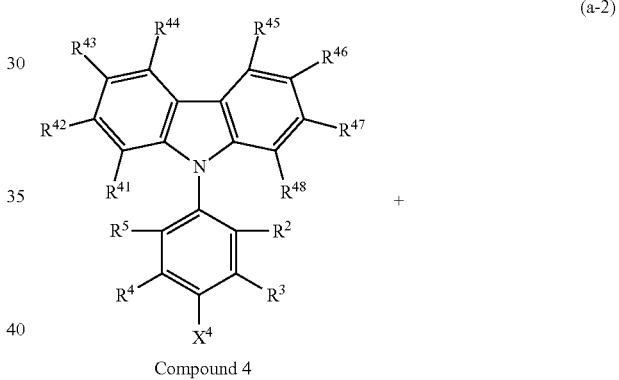

Compound 4

+

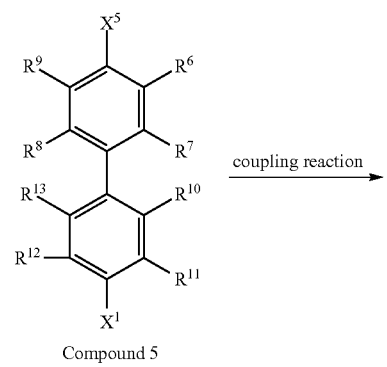

Compound 5

-continued

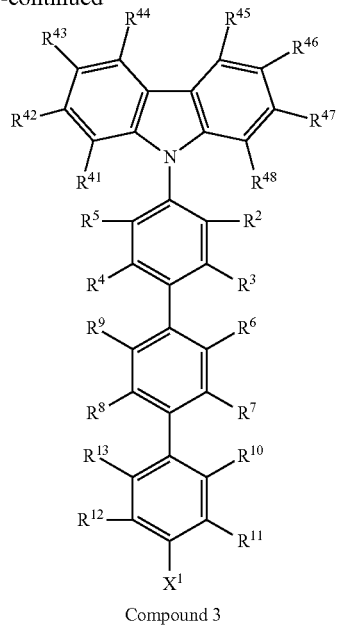

Compound 3

[Chemical Formula 33]

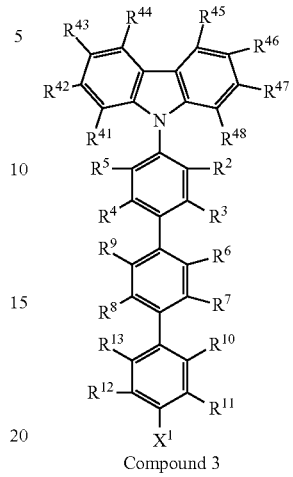

Compound 3

+

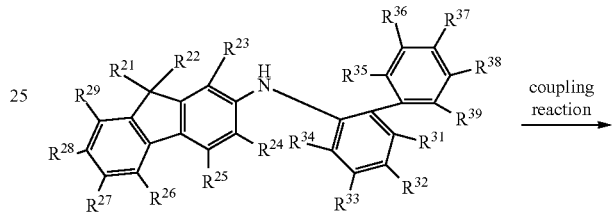

Compound 6

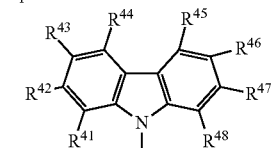

(G1)

In Synthesis Scheme (a-2), each of $X^1$, $X^4$, and $X^5$ independently represents a halogen, a boronic acid group, an organoboron group, a triflate group, an organotin group, an organozinc group, or a magnesium halide group. As the halogen, iodine, bromine, or chlorine is preferred.

As the reaction represented by Synthesis Scheme (a-2), a Suzuki-Miyaura coupling reaction using a palladium catalyst, a Migita-Kosugi-Stille coupling reaction using an organotin compound, a Kumada-Tamao-Corriu coupling reaction using a Grignard reagent, a Negishi coupling reaction using an organozinc compound, an Ullmann reaction using copper or a copper compound, or the like can be performed. In the case where these reactions are employed, the description of Synthesis Scheme (a-1) can be referred to for the details.

Compound 3 can be used for the coupling reaction in a combination with various diarylamine compounds; thus, Compound 3 greatly contributes to facilitation and progress of material development. Furthermore, since Compound 3 includes a halogen, Compound 3 can be used as a source material for not only the amination reaction but also for the Suzuki-Miyaura coupling reaction, the Migita-Kosugi-Stille coupling reaction, the Kumada-Tamao-Corriu coupling reaction, the Negishi coupling reaction, and the Ullmann reaction. That is, Compound 3 can be widely used for coupling reactions to make a carbon-carbon bond, and thus is an effective and useful compound.

Next, as shown in Synthesis Scheme (a-3), Compound 3 obtained in Synthesis Scheme (a-1) or Synthesis Scheme (a-2) and a diarylamine compound (Compound 6) are coupled, whereby the organic compound represented by General Formula (G1) can be obtained.

In Synthesis Scheme (a-3), X represents a halogen. As the halogen, iodine, bromine, or chlorine is preferable.

As the reaction represented by Synthesis Scheme (a-3), a Buchwald-Hartwig amination reaction using a palladium catalyst can be performed. As the palladium catalyst for the reaction, a palladium compound such as bis(dibenzylideneacetone)palladium(0), palladium(II) acetate, [1,1-bis(diphenylphosphino)ferrocene]palladium(II) dichloride, tetrakis(triphenylphosphine)palladium(0), or allylpalladium(II) chloride (dimer) can be used. As a ligand, tri(tert-butyl)phosphine, tri(n-hexyl)phosphine, tricyclohexylphosphine, di(1-adamantyl)-n-butylphosphine, 2-dicyclohexylphosphino-2', 6'-dimethoxybiphenyl, tri(ortho-tolyl)phosphine, di-tert-butyl(1-methyl-2,2-diphenylcyclopropyl)phosphine (abbreviation: cBRIDP (registered trademark)), or the like can be used. In the reaction, an organic base such as sodium tert-butoxide, an inorganic base such as potassium carbonate, cesium carbonate, or sodium carbonate, or the like can be used. As a solvent in the reaction, toluene, xylene, benzene, tetrahydrofuran, dioxane, or the like can be used. Note that reagents that can be used in the reaction are not limited to these.

In the case where the Ullmann reaction is performed in Synthesis Scheme (a-3), copper or a copper compound can be used as a reagent, and an inorganic base such as potassium carbonate can be used as a base. Examples of the solvent that can be used in the reaction include 1,3-dimethyl-3,4,5,6-tetrahydro-2(1H)pyrimidinone (DMPU), toluene, xylene, and benzene. In the Ullmann reaction, the target substance can be obtained in a shorter time and in a higher yield when the reaction temperature is 100° C. or higher; therefore, it is preferable to use DMPU or xylene, which have high boiling temperatures. In addition, the reaction temperature is more preferably 150° C. or higher; therefore, DMPU is more preferably used. Note that reagents that can be used in the reaction are not limited to these.

<<Synthesis Method 2 of Organic Compound Represented by General Formula (G1)>>

The organic compound represented by General Formula (G1) can be synthesized through Synthesis Scheme (b-1).

As shown in Synthesis Scheme (b-1), a 9-biphenyl-9H-carbazole compound (Compound 7) and a triarylamine compound (Compound 8) are coupled, whereby the organic compound represented by General Formula (G1) can be obtained.

[Chemical Formula 34]

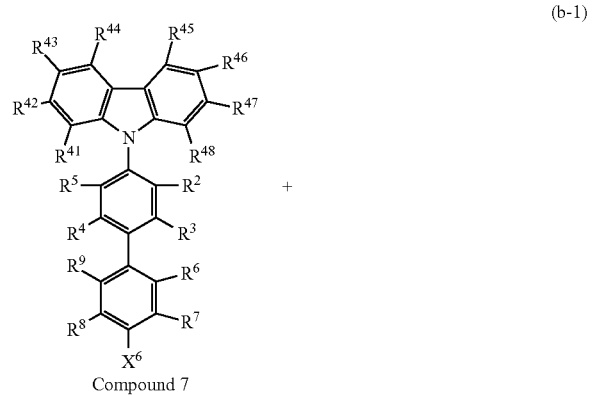

Compound 7

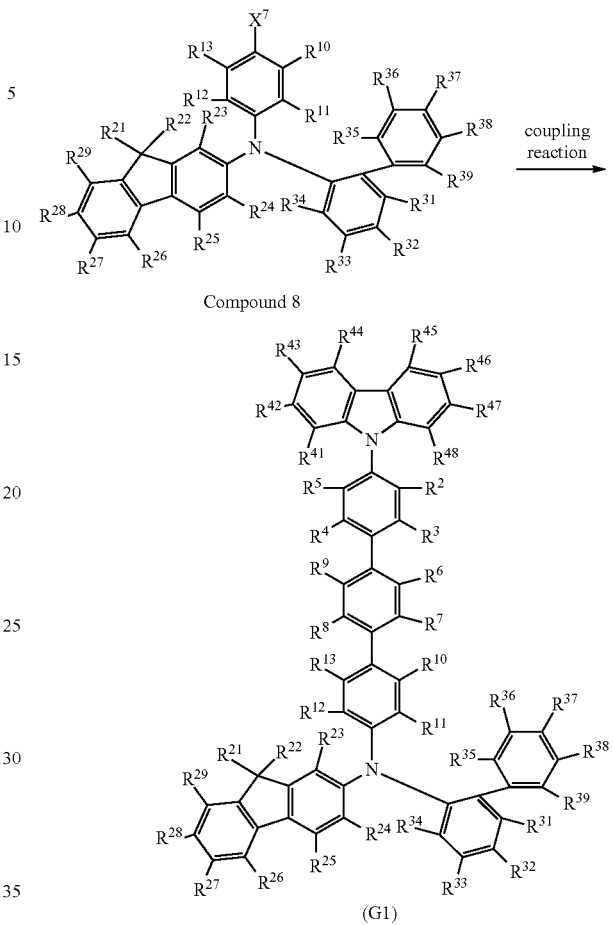

Compound 8

(G1)

In Synthesis Scheme (b-1), each of $X^6$ and $X^7$ independently represents a halogen, a boronic acid group, an organoboron group, a triflate group, an organotin group, an organozinc group, or a magnesium halide group. The halogen is preferably chlorine, bromine, or iodine; bromine or iodine is preferred in terms of reactivity, and chlorine or bromine is preferred in terms of cost.

As the reaction represented by Synthesis Scheme (b-1), a Suzuki-Miyaura coupling reaction using a palladium catalyst, a Migita-Kosugi-Stille coupling reaction using an organotin compound, a Kumada-Tamao-Corriu coupling reaction using a Grignard reagent, a Negishi coupling reaction using an organozinc compound, a reaction using copper or a copper compound, or the like can be performed. In the case where these reactions are employed, the description of Synthesis Scheme (a-1) can be referred to for the details.

<<Synthesis Method 3 of Organic Compound Represented by General Formula (G1)>>

The organic compound represented by General Formula (G1) can be synthesized through Synthesis Scheme (c-1).

As shown in Synthesis Scheme (c-1), a 9-phenyl-9H-carbazole compound (Compound 9) and a triarylamine compound (Compound 10) are coupled, whereby the organic compound represented by General Formula (G1) can be obtained.

[Chemical Formula 35]

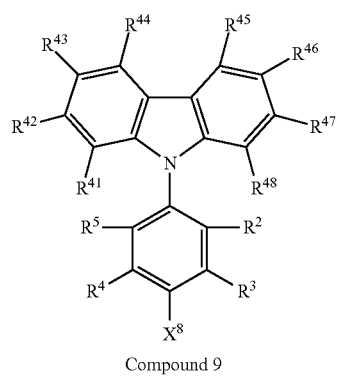

Compound 9

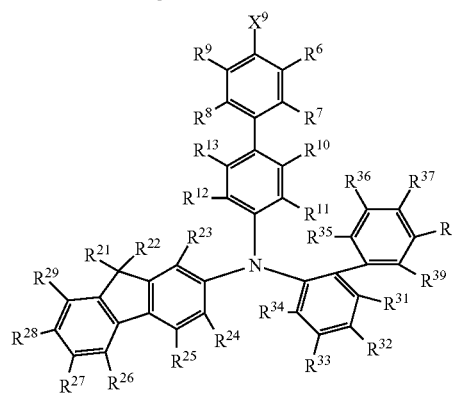

Compound 10

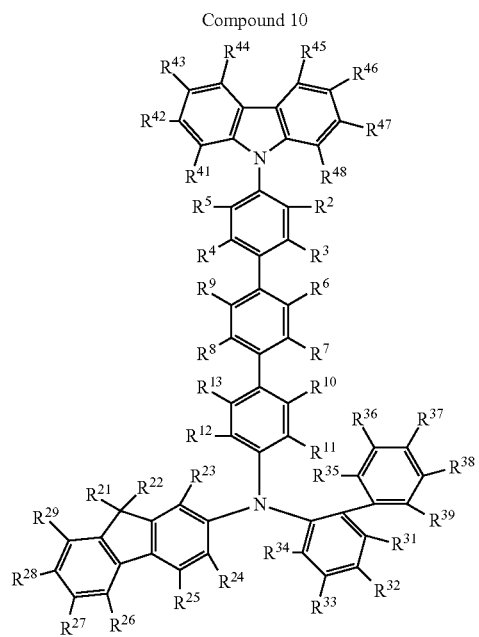

(G1)

In Synthesis Scheme (c-1), each of $X^8$ and $X^9$ independently represents a halogen, a boronic acid group, an organoboron group, a triflate group, an organotin group, an organozinc group, or a magnesium halide group. The halogen is preferably chlorine, bromine, or iodine; bromine or iodine is preferred in terms of reactivity, and chlorine or bromine is preferred in terms of cost.

As the reaction represented by Synthesis Scheme (c-1), a Suzuki-Miyaura coupling reaction using a palladium catalyst, a Migita-Kosugi-Stille coupling reaction using an organotin compound, a Kumada-Tamao-Corriu coupling reaction using a Grignard reagent, a Negishi coupling reaction using an organozinc compound, a reaction using copper or a copper compound, or the like can be performed. In the case where these reactions are employed, the description of Synthesis Scheme (a-1) can be referred to for the details.

<<Synthesis Method 4 of Organic Compound Represented by General Formula (G1)>>

The organic compound represented by General Formula (G1) can be synthesized through Synthesis Scheme (d-1).

As shown in Synthesis Scheme (d-1), a 9-terphenyl-9H-carbazole compound (Compound 11) and a biphenyl compound (Compound 12) are coupled, whereby a diarylamine compound (Compound 13) can be obtained. Subsequently, a fluorene compound (Compound 14) and Compound 13 are coupled, whereby the organic compound represented by General Formula (G1) can be obtained.

[Chemical Formula 36]

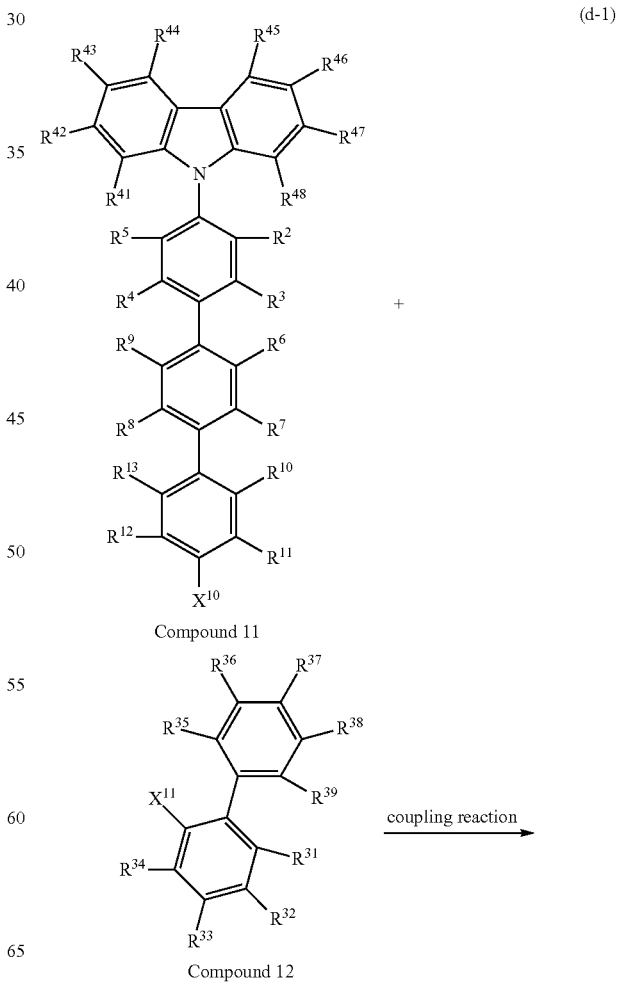

Compound 11

Compound 12

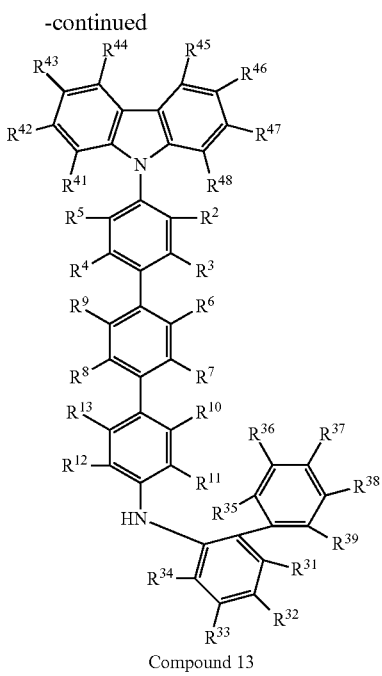

Compound 13

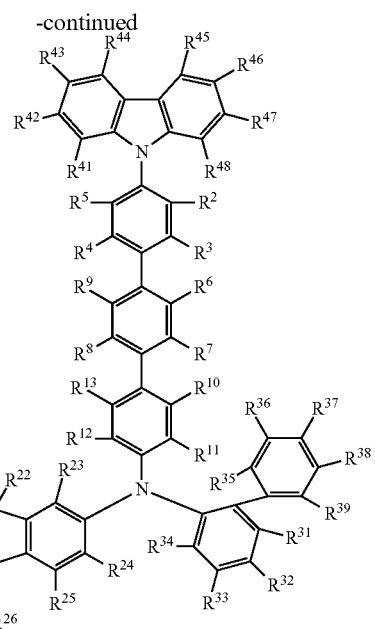

(G1)

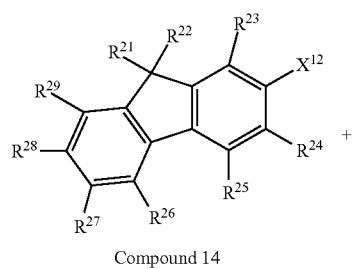

Compound 14

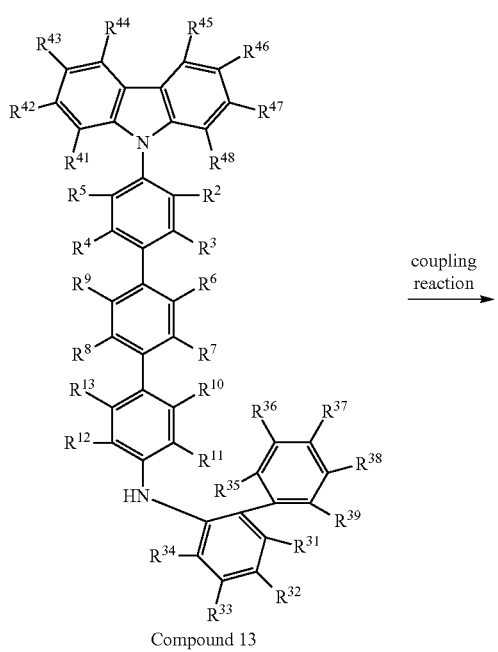

Compound 13

In Synthesis Scheme (d-1), one of $X^{10}$ and $X^{11}$ represents an amino group, and the other represents a halogen or a triflate group. $X^{12}$ represents a halogen or a triflate group. The halogen is preferably chlorine, bromine, or iodine; bromine or iodine is preferred in terms of reactivity, and chlorine or bromine is preferred in terms of cost.

As the reaction represented by Synthesis Scheme (d-1), a Buchwald-Hartwig amination reaction using a palladium catalyst, an Ullmann reaction using copper or a copper compound, or the like can be performed. In the case where these reactions are employed, the description of Synthesis Scheme (a-3) can be referred to for the details.

<<Synthesis Method 5 of Organic Compound Represented by General Formula (G1)>>

The organic compound represented by General Formula (G1) can be synthesized through Synthesis Scheme (e-1).

As shown in Synthesis Scheme (e-1), a 9-terphenyl-9H-carbazole compound (Compound 15) and a fluorene compound (Compound 16) are coupled, whereby a diarylamine compound (Compound 17) can be obtained. Subsequently, a biphenyl compound (Compound 18) and the diarylamine compound (Compound 17) are coupled, whereby an organic compound represented by General Formula (G1) can be obtained.

[Chemical Formula 37]
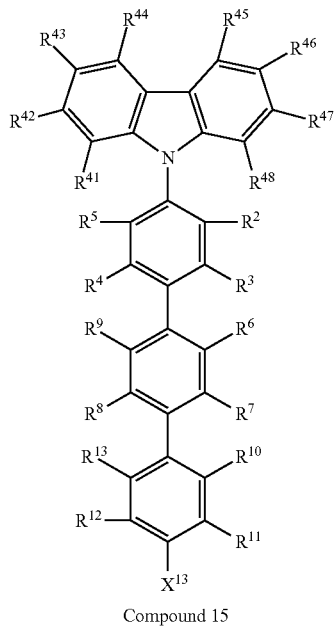
Compound 15
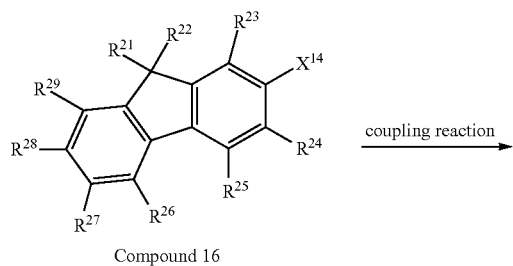
Compound 16
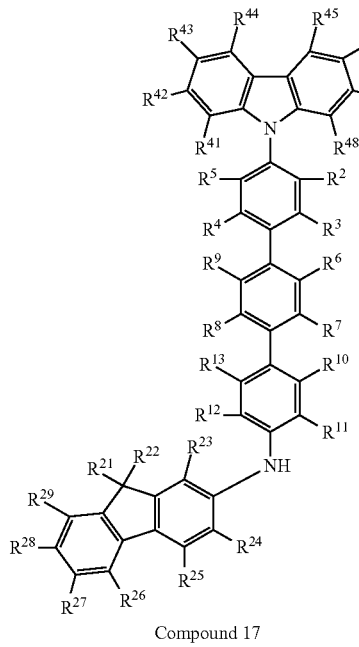
Compound 17
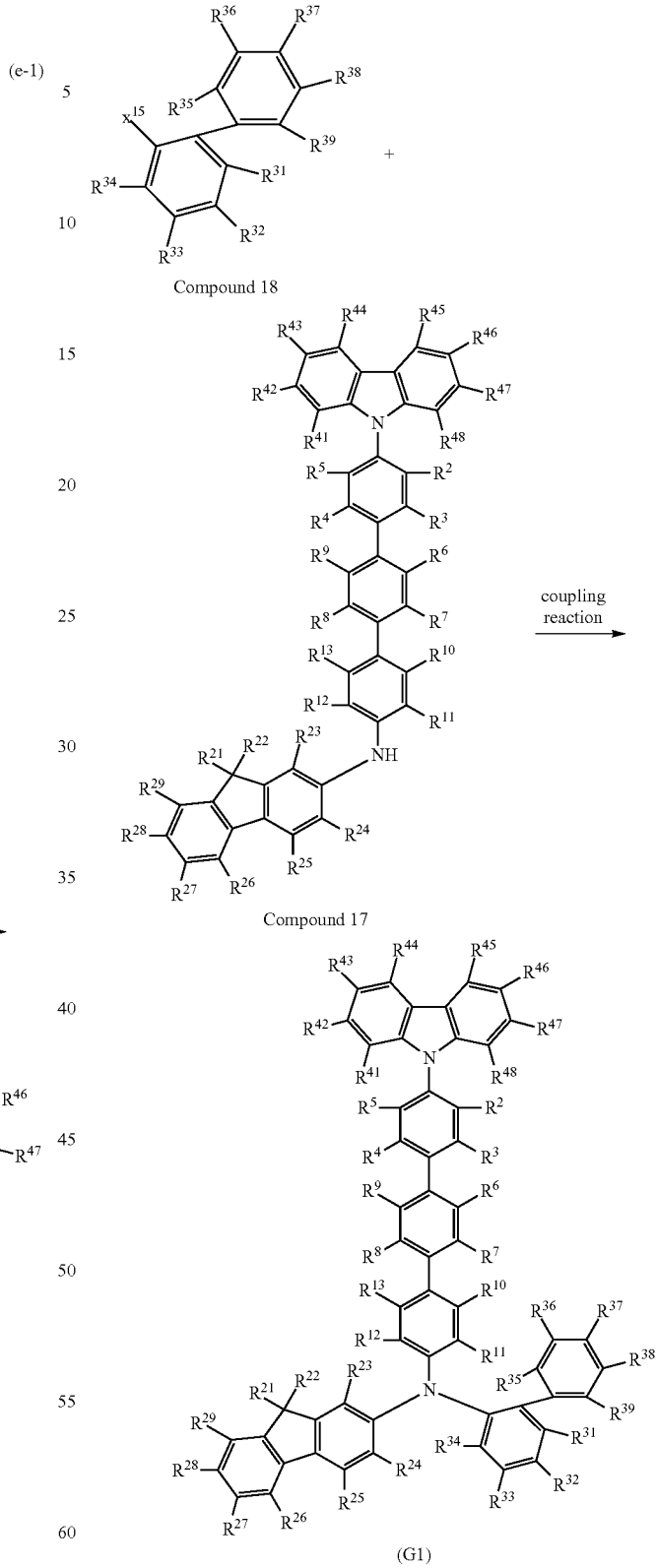
In Synthesis Scheme (e-1), one of $X^{13}$ and $X^{14}$ represents an amino group, and the other represents a halogen or a triflate group. $X^{15}$ represents a halogen or a triflate group. The halogen is preferably chlorine, bromine, or iodine;

bromine or iodine is preferred in terms of reactivity, and chlorine or bromine is preferred in terms of cost.

As the reaction represented by Synthesis Scheme (e-1), a Buchwald-Hartwig amination reaction using a palladium catalyst, an Ullmann reaction using copper or a copper compound, or the like can be performed. In the case where these reactions are employed, the description of Synthesis Scheme (a-3) can be referred to for the details.

The methods of synthesizing the organic compound of one embodiment of the present invention are described above; however, the present invention is not limited thereto, and another synthesis method may be employed.

The organic compound of one embodiment of the present invention has high heat resistance and high sublimability, and thus is suitable for a material of a light-emitting device or a material of a light-receiving device. The organic compound of one embodiment of the present invention has a high hole-transport property and a high electron-blocking property, and is suitable as a host material or a hole-transport material in a light-emitting device. A light-emitting device can have high emission efficiency by including the organic compound of one embodiment of the present invention. The light-emitting device can have high reliability by including the organic compound of one embodiment of the present invention.

This embodiment can be combined with the other embodiment as appropriate. In this specification, in the case where a plurality of structure examples are shown in one embodiment, the structure examples can be combined as appropriate.

Embodiment 2

In this embodiment, a light-emitting device of one embodiment of the present invention will be described with reference to FIGS. 1A to 1D. In this embodiment, a light-emitting device having a function of emitting visible light or near-infrared light is described.

Structure Example of Light-Emitting Device

<<Basic Structure of Light-Emitting Device>>

FIGS. 1A to 1D illustrate examples of light-emitting devices including an EL layer between a pair of electrodes.

The light-emitting device illustrated in FIG. 1A has a structure in which an EL layer 103 is provided between a first electrode 101 and a second electrode 102 (a single structure). The EL layer 103 includes at least a light-emitting layer.

Figure 1B:
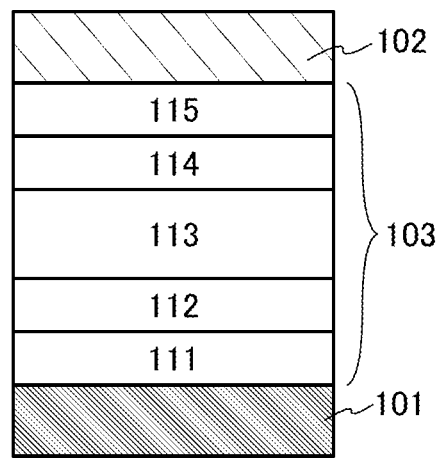

FIG. 1B illustrates an example of a stacked structure of the EL layer 103. In this embodiment, an example in which the first electrode 101 functions as an anode and the second electrode 102 functions as a cathode is described. The EL layer 103 has, over the first electrode 101, a structure in which a hole-injection layer 111, a hole-transport layer 112, a light-emitting layer 113, an electron-transport layer 114, and an electron-injection layer 115 are stacked in this order. Each of the hole-injection layer 111, the hole-transport layer 112, the light-emitting layer 113, the electron-transport layer 114, and the electron-injection layer 115 may have a single layer structure or a stacked structure. In the case where the first electrode 101 functions as a cathode and the second electrode 102 functions as an anode, the stacking order is reversed.

The light-emitting device may include a plurality of EL layers between the pair of electrodes. For example, it is preferable that the light-emitting device include n EL layers (n is an integer greater than or equal to 2) and a charge-generation layer 104 be provided between an (n−1)th EL layer and an n-th EL layer.

Figure 1C:
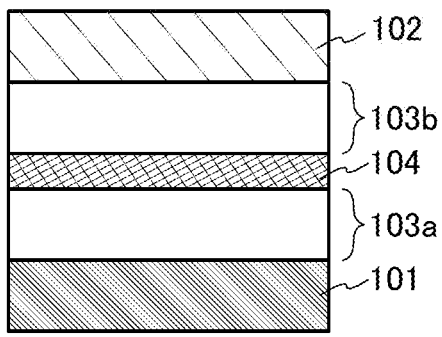
Figure 1D:
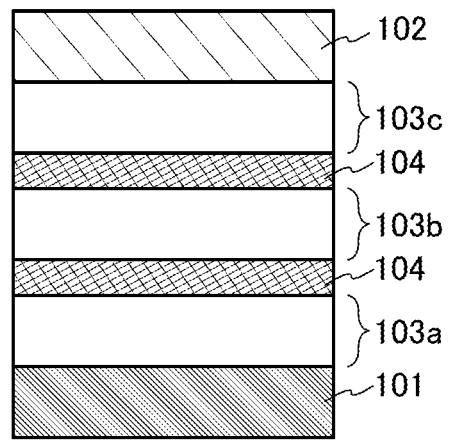

FIG. 1C illustrates a light-emitting device with a tandem structure in which two EL layers (103a and 103b) are provided between a pair of electrodes. FIG. 1D illustrates a light-emitting device with a tandem structure in which three EL layers (103a, 103b, and 103c) are provided.

Each of the EL layers 103a, 103b, and 103c includes at least a light-emitting layer. In the case where a plurality of EL layers are provided as in the tandem structure illustrated in FIG. 1C or FIG. 1D, each of the EL layers can have a stacked structure similar to that of the EL layer 103 illustrated in FIG. 1B. Each of the EL layers 103a, 103b, and 103c can include one or more of the hole-injection layer 111, the hole-transport layer 112, the electron-transport layer 114, and the electron-injection layer 115.

The charge-generation layer 104 in FIG. 1C has a function of injecting electrons into one of the EL layer 103a and the EL layer 103b and injecting holes into the other of the EL layers when voltage is applied to the first electrode 101 and the second electrode 102. Thus, when voltage is applied to the first electrode 101 in FIG. 1C such that the potential of the first electrode 101 becomes higher than that of the second electrode 102, the charge-generation layer 104 injects electrons into the EL layer 103a and injects holes into the EL layer 103b.

Note that in terms of light extraction efficiency, the charge-generation layer 104 preferably transmits visible light or near-infrared light (specifically, the transmittance of visible light or near-infrared light of the charge-generation layer 104 is preferably 40% or higher). Furthermore, the charge-generation layer 104 functions even if it has lower conductivity than the first electrode 101 or the second electrode 102.

Note that the EL layers can be provided in contact with each other with no charge-generation layer 104 provided therebetween when these EL layers allow the same structure as the charge-generation layer 104 to be formed therebetween. For example, when a charge-generation region is formed over one surface of an EL layer, another EL layer can be provided in contact with the surface.

A light-emitting device with a tandem structure has higher current efficiency than a light-emitting device with a single structure, and needs a smaller amount of current when the devices emit light with the same luminance. Thus, the light-emitting device with a tandem structure has a long lifetime, which can improve the reliability of a light-emitting apparatus or an electronic device.

The light-emitting layer 113 contains a light-emitting substance and a plurality of substances in appropriate combination, so that fluorescence or phosphorescence with a desired wavelength can be obtained. The light-emitting layer 113 may have a stacked structure of layers with different emission wavelengths. In that case, light-emitting substances and other substances are different between the stacked light-emitting layers. The EL layers 103a, 103b, and 103c illustrated in FIG. 1C or FIG. 1D may emit light with different wavelengths. Also in that case, the light-emitting substances and other substances are different between the stacked light-emitting layers. For example, in the structure of FIG. 1C, when the EL layer 103a emits red light and green light and the EL layer 103b emits blue light, the light-emitting device can emit white light as a whole. In one light-emitting device, a plurality of light-emitting layers or a plurality of EL layers may emit light of the same color. For example, in the structure of FIG. 1D, when the EL layer 103a emits first blue light, the EL layer 103b emits yellow light, yellowish green light, or green light and red light, and the EL layer 103c emits second blue light, the light-emitting device can emit white light as a whole.

In the light-emitting device of one embodiment of the present invention, light obtained from the EL layer may be resonated between a pair of electrodes in order to intensify the light. For example, for FIG. 1B, a micro optical resonator (microcavity) structure in which the first electrode 101 is a reflective electrode and the second electrode 102 is a transflective electrode is employed, whereby light obtained from the EL layer 103 can be intensified.

With the use of the microcavity structure for the light-emitting device, light with different wavelengths (monochromatic light) can be extracted even if the same EL layer is used. Thus, formation of functional layers for respective pixels (what is called separate coloring) is not necessary for obtaining different emission colors. Therefore, high definition can be easily achieved. Note that a combination with coloring layers (color filters) is also possible. Furthermore, the emission intensity of light with a specific wavelength in the front direction can be increased, whereby power consumption can be reduced.

Note that in the case where the first electrode 101 of the light-emitting device is a reflective electrode having a stacked structure of a conductive film having a reflecting property with respect to visible light or near-infrared light and a conductive film having a transmitting property with respect to visible light or near-infrared light, optical adjustment can be performed by controlling the thicknesses of the conductive film having a transmitting property. Specifically, when the wavelength of light obtained from the light-emitting layer 113 is k, the distance between the first electrode 101 and the second electrode 102 is preferably adjusted to around $m\lambda/2$ (m is a natural number).

To amplify desired light (wavelength: k) obtained from the light-emitting layer 113, it is preferable to adjust each of the optical path length from the first electrode 101 to a region where the desired light is obtained in the light-emitting layer 113 (light-emitting region) and the optical path length from the second electrode 102 to the region where the desired light is obtained in the light-emitting layer 113 (light-emitting region) to be around $(2m'+1)\lambda/4$ (m' is a natural number). Here, the light-emitting region means a region where holes and electrons are recombined in the light-emitting layer 113.

By such optical adjustment, the spectrum of light obtained from the light-emitting layer 113 can be narrowed and light emission with high color purity can be obtained.

In that case, the optical path length between the first electrode 101 and the second electrode 102 is, to be exact, the total thickness from a reflective region in the first electrode 101 to a reflective region in the second electrode 102. However, it is difficult to precisely determine the reflective regions in the first electrode 101 and the second electrode 102; thus, it is assumed that the above effect can be sufficiently obtained wherever the reflective regions may be set in the first electrode 101 and the second electrode 102. Furthermore, the optical path length between the first electrode 101 and the light-emitting layer that emits the desired light is, to be exact, the optical path length between the reflective region in the first electrode 101 and the light-emitting region in the light-emitting layer that emits the desired light. However, it is difficult to precisely determine the reflective region in the first electrode 101 and the light-emitting region in the light-emitting layer that emits the desired light; thus, it is assumed that the above effect can be sufficiently obtained wherever the reflective region and the light-emitting region may be set in the first electrode 101 and the light-emitting layer that emits the desired light, respectively.

At least one of the first electrode 101 and the second electrode 102 has a transmitting property with respect to visible light or near-infrared light. The transmissivity of visible light or near-infrared light of the electrode having a transmitting property with respect to visible light or near-infrared light is higher than or equal to 40%. In the case where the electrode having a transmitting property with respect to visible light or near-infrared light is the above-described transflective electrode, the reflectance of visible light or near-infrared light of the electrode is higher than or equal to 20% and lower than or equal to 80%, preferably higher than or equal to 40% and lower than or equal to 70%. These electrodes preferably have a resistivity of $1\times10^{-2}$ Ωm or lower.

When the first electrode 101 or the second electrode 102 is an electrode having reflectivity with respect to visible light or near-infrared light (reflective electrode), the reflectance of visible light or near-infrared light of the reflective electrode is higher than or equal to 40% and lower than or equal to 100%, preferably higher than or equal to 70% and lower than or equal to 100%. This electrode preferably has a resistivity of $1\times10^{-2}$ Ωm or lower.

<<<Specific Structure of Light-Emitting Device>>

Next, a specific structure of the light-emitting device is described. Here, a light-emitting device having the single structure in FIG. 1B is described.

<First Electrode and Second Electrode>

As materials used for the first electrode 101 and the second electrode 102, any of the materials below can be used in an appropriate combination as long as the functions of both electrodes described above can be fulfilled. For example, a metal, an alloy, an electrically conductive compound, a mixture of these, and the like can be appropriately used. Specifically, an In—Sn oxide (also referred to as ITO), an In—Si—Sn oxide (also referred to as ITSO), an In—Zn oxide, and an In—W—Zn oxide can be given. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use a Group 1 element or a Group 2 element in the periodic table, which is not described above (e.g., a rare earth metal such as lithium (Li), cesium (Cs), calcium (Ca), strontium (Sr), europium (Eu), or ytterbium (Yb), an alloy containing an appropriate combination of any of these, graphene, or the like.

Note that in the case where a light-emitting device having a microcavity structure is fabricated, the first electrode 101 is formed as a reflective electrode and the second electrode 102 is formed as a transflective electrode. Thus, a single-layer structure or a stacked-layer structure can be formed using one or more kinds of desired conductive materials. Note that the second electrode 102 is formed after formation of the EL layer 103, with the use of a material selected as described above. For fabrication of these electrodes, a sputtering method or a vacuum evaporation method can be used.

<Hole-Injection Layer and Hole-Transport Layer>

The hole-injection layer 111 injects holes from the first electrode 101 that is an anode to the EL layer 103 and contains a material with a high hole-injection property.

As the material with a high hole-injection property, for example, a transition metal oxide such as molybdenum oxide, vanadium oxide, ruthenium oxide, tungsten oxide, or manganese oxide or a phthalocyanine-based compound such as phthalocyanine (abbreviation: $H_2Pc$) or copper(II) phthalocyanine (abbreviation: CuPc) can be used.

As the material with a high hole-injection property, an aromatic amine compound, such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), or 3-[N-(1-naphthyl)-N-(9-phenylcarbazol-3-yl)amino]-9-phenylcarbazole (abbreviation: PCzPCN1), can be used.

As the material with a high hole-injection property, poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide](abbreviation: PTPDMA), or poly[N,N'-bis(4-butylphenyl)-N,N'-bis(phenyl)benzidine](abbreviation: Poly-TPD) can be used. Alternatively, a high-molecular compound to which acid is added, such as poly(3,4-ethylenedioxythiophene)/poly(styrenesulfonic acid) (abbreviation: PEDOT/PSS) or polyaniline/poly(styrenesulfonic acid) (abbreviation: PAni/PSS), can be used.

Alternatively, as the material with a high hole-injection property, a composite material containing a hole-transport material and an acceptor material (an electron-accepting material) can also be used. In that case, the acceptor material extracts electrons from a hole-transport material, so that holes are generated in the hole-injection layer 111 and the holes are injected into the light-emitting layer 113 through the hole-transport layer 112. Note that the hole-injection layer 111 may be formed to have a single-layer structure including a composite material containing a hole-transport material and an acceptor material, or may be formed by stacking respective layers of a hole-transport material and an acceptor material.

The hole-transport layer 112 transports the holes, which are injected from the first electrode 101 by the hole-injection layer 111, to the light-emitting layer 113. The hole-transport layer 112 contains a hole-transport material. It is particularly preferable that the highest occupied molecular orbital (HOMO) level of the hole-transport material included in the hole-transport layer 112 be the same as or close to that of the hole-injection layer 111.

As the acceptor material used for the hole-injection layer 111, an oxide of a metal belonging to any of Group 4 to Group 8 of the periodic table can be used. As specific examples, molybdenum oxide, vanadium oxide, niobium oxide, tantalum oxide, chromium oxide, tungsten oxide, manganese oxide, and rhenium oxide can be given. Among these, molybdenum oxide is especially preferable since it is stable in the air, has a low hygroscopic property, and is easy to handle. Alternatively, organic acceptors such as a quinodimethane derivative, a chloranil derivative, and a hexaazatriphenylene derivative can be used. Examples of a compound having an electron-withdrawing group (a halogen group or a cyano group) include 7,7,8,8-tetracyano-2,3,5,6-tetrafluoroquinodimethane (abbreviation: $F_4$-TCNQ), chloranil, 2,3,6,7,10,11-hexacyano-1,4,5,8,9,12-hexaazatriphenylene (abbreviation: HAT-CN), and 1,3,4,5,7,8-hexafluorotetracyano-naphthoquinodimethane (abbreviation: F6-TCNNQ). In particular, a compound in which electron-withdrawing groups are bonded to a condensed aromatic ring having a plurality of heteroatoms, such as HAT-CN, is preferred because it is thermally stable. A [3]radialene derivative having an electron-withdrawing group (in particular, a cyano group or a halogen group such as a fluoro group) has a very high electron-accepting property and thus is preferred. Specific examples include $\alpha,\alpha',\alpha''$-1,2,3-cyclopropanetriylidenetris[4-cyano-2,3,5,6-tetrafluorobenzeneacetonitrile], $\alpha,\alpha',\alpha''$-1,2,3-cyclopropanetriylidenetris[2,6-dichloro-3,5-difluoro-4-(trifluoromethyl)benzeneacetonitrile], and $\alpha,\alpha',\alpha''$-1,2,3-cyclopropanetriylidenetris[2,3,4,5,6-pentafluorobenzeneacetonitrile].

The hole-transport materials used for the hole-injection layer 111 and the hole-transport layer 112 are preferably substances with a hole mobility of greater than or equal to $10^{-6}$ cm$^2$/Vs. Note that other substances may be used as long as the substances have a hole-transport property higher than an electron-transport property.

The light-emitting device of one embodiment of the present invention preferably includes the organic compound of one embodiment of the present invention as a hole-transport material that is used for the hole-injection layer 111 and/or the hole-transport layer 112. Since the organic compound of one embodiment of the present invention has a high electron-blocking property, use of the organic compound for the hole-transport layer 112 can improve the emission efficiency of the light-emitting device.

As the hole-transport material, materials having a high hole-transport property, such as a π-electron rich heteroaromatic compound (e.g., a carbazole derivative, a thiophene derivative, and a furan derivative) and an aromatic amine (a compound having an aromatic amine skeleton), are preferred.

Examples of the carbazole derivative (a compound having a carbazole skeleton) include a bicarbazole derivative (e.g., a 3,3'-bicarbazole derivative) and an aromatic amine having a carbazolyl group.

Specific examples of the bicarbazole derivative (e.g., a 3,3'-bicarbazole derivative) include 3,3'-bis(9-phenyl-9H-carbazole) (abbreviation: PCCP), 9,9'-bis(1,1'-biphenyl-4-yl)-3,3'-bi-9H-carbazole, 9,9'-bis(1,1'-biphenyl-3-yl)-3,3'-bi-9H-carbazole, 9-(1,1'-biphenyl-3-yl)-9'-(1,1'-biphenyl-4-yl)-9H,9'H-3,3'-bicarbazole (abbreviation: mBPCCBP), 9-(2-naphthyl)-9'-phenyl-9H,9'H-3,3'-bicarbazole (abbreviation: βNCCP).

Specific examples of the aromatic amine having a carbazolyl group include 4-phenyl-4'-(9-phenyl-9H-carbazol-3-yl)triphenylamine (abbreviation: PCBA1BP), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N',N''-triphenyl-N,N',N''-tris(9-phenylcarbazol-3-yl)benzene-1,3,5-triamine (abbreviation: PCA3B), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), PCzPCA1, PCzPCA2, PCzPCN1, 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 2-[N-(9-phenylcarbazol-3-yl)-N-phenylamino]spiro-9,9'-bifluorene (abbreviation: PCASF), N-[4-(9H-carbazol-9-yl)phenyl]-N-(4-phenyl)phenylaniline (abbreviation: YGA1BP), N,N'-bis[4-(carbazol-9-yl)phenyl]-N,N'-diphenyl-9,9-dimethylfluorene-2,7-diamine (abbreviation: YGA2F), and 4,4',4''-tris(carbazol-9-yl)triphenylamine (abbreviation: TCTA).

In addition to the above, other examples of the carbazole derivative include 3-[4-(9-phenanthryl)-phenyl]-9-phenyl-9H-carbazole (abbreviation: PCPPn), 3-[4-(1-naphthyl)-phenyl]-9-phenyl-9H-carbazole (abbreviation: PCPN), 1,3-bis(N-carbazolyl)benzene (abbreviation: mCP), 4,4'-di(N-carbazolyl)biphenyl (abbreviation: CBP),3,6-bis(3,5-diphenylphenyl)-9-phenylcarbazole(abbreviation: CzTP),1,3,5-tris[4-(N-carbazolyl)phenyl]benzene (abbreviation: TCPB), and 9-[4-(10-phenyl-9-anthracenyl)phenyl]-9H-carbazole(abbreviation: CzPA).

Specific examples of the thiophene derivative (a compound having a thiophene skeleton) and the furan derivative (a compound having a furan skeleton) include a compound having a thiophene skeleton, such as 4,4',4''-(benzene-1,3,5-triyl)tri(dibenzothiophene)(abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV), 4,4',4''-(benzene-1,3,5-triyl)tri(dibenzofuran)(abbreviation: DBF3P-II), and 4-{3-[3-(9-phenyl-9H-fluoren-9-yl)phenyl]phenyl}dibenzofuran(abbreviation: mmDBFFLBi-II).

Specific examples of the aromatic amine include 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 2,7-bis[N-(4-diphenylaminophenyl)-N-phenylamino]-spiro-9,9'-bifluorene (abbreviation: DPA2SF), 4,4',4''-tris[N-(1-naphthyl)-N-phenylamino]triphenylamine (abbreviation: 1'-TNATA), TDATA, m-MTDATA, N,N'-di(p-tolyl)-N,N'-diphenyl-p-phenylenediamine (abbreviation: DTDPPA), DPAB, DNTPD, and DPA3B.

As the hole-transport material, a high molecular compound such as PVK, PVTPA, PTPDMA, or Poly-TPD can also be used.

Note that the hole-transport material is not limited to the above examples and one of or a combination of various known materials can be used as the hole-transport material for the hole-injection layer 111 and the hole-transport layer 112.

<Light-Emitting Layer>

The light-emitting layer 113 contains a light-emitting substance. The light-emitting layer 113 can contain one or more kinds of light-emitting substances. As the light-emitting substance, a substance whose emission color is blue, violet, bluish violet, green, yellowish green, yellow, orange, red, or the like is appropriately used. Alternatively, as the light-emitting substance, a substance that emits near-infrared light can be used. When a plurality of light-emitting layers are formed using different light-emitting substances, different emission colors can be exhibited (for example, complementary emission colors are combined to achieve white light emission). Furthermore, a light-emitting layer may contain different light-emitting substances.

The light-emitting layer 113 preferably contains one or more kinds of organic compounds (e.g., a host material and an assist material) in addition to the light-emitting substance (a guest material). As the one or more kinds of organic compounds, the hole-transport material and/or the electron-transport material described in this embodiment can be used. Alternatively, as the one or more kinds of organic compounds, a bipolar material may be used.

In the case where the hole-transport material is used for the light-emitting layer 113, the hole-transport material is preferably the organic compound of one embodiment of the present invention.

There is no particular limitation on the light-emitting substances that can be used for the light-emitting layer 113, and a light-emitting substance that converts singlet excitation energy into light emission in the visible light range or the near-infrared light range or a light-emitting substance that converts triplet excitation energy into light emission in the visible light range or the near-infrared light range can be used.

As an example of the light-emitting substance that converts singlet excitation energy into light emission, a substance that emits fluorescence (fluorescent material) can be given, and the examples include pyrene derivatives, anthracene derivatives, triphenylene derivatives, fluorene derivatives, carbazole derivatives, dibenzothiophene derivatives, dibenzofuran derivatives, dibenzoquinoxaline derivatives, quinoxaline derivatives, pyridine derivatives, pyrimidine derivatives, phenanthrene derivatives, and naphthalene derivatives. Pyrene derivatives are particularly preferable because they have a high emission quantum yield. Specific examples of pyrene derivatives include N,N'-bis(3-methylphenyl)-N,N'-bis[3-(9-phenyl-9H-fluoren-9-yl)phenyl]pyrene-1,6-diamine (abbreviation: 1,6mMemFLPAPrn), (N,N'-diphenyl-N,N'-bis[4-(9-phenyl-9H-fluoren-9-yl)phenyl]pyrene-1,6-diamine) (abbreviation: 1,6FLPAPrn), N,N'-bis(dibenzofuran-2-yl)-N,N'-diphenylpyrene-1,6-diamine (abbreviation: 1,6FrAPrn), N,N'-bis(dibenzothiophen-2-yl)-N,N'-diphenylpyrene-1,6-diamine (abbreviation: 1,6ThAPrn), N,N'-(pyrene-1,6-diyl)bis[(N-phenylbenzo[b]naphtho[1,2-d]furan)-6-amine] (abbreviation: 1,6BnfAPrn), N,N'-(pyrene-1,6-diyl)bis[(N-phenylbenzo[b]naphtho[1,2-d]furan)-8-amine] (abbreviation: 1,6BnfAPrn-02), and N,N'-(pyrene-1,6-diyl)bis[(6,N-diphenylbenzo[b]naphtho[1,2-d]furan)-8-amine](abbreviation: 1,6BnfAPrn-03).

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra(tert-butyl)perylene (abbreviation: TBP), N,N'''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), or the like.

As examples of a light-emitting substance that converts triplet excitation energy into light emission, a substance that emits phosphorescence (phosphorescent material) and a thermally activated delayed fluorescence (TADF) material that exhibits thermally activated delayed fluorescence can be given.

Examples of a phosphorescent material include an organometallic complex, a metal complex (platinum complex), and a rare earth metal complex. These substances exhibit the respective emission colors (emission peaks) and thus, any of them is appropriately selected and used according to need.

As examples of a phosphorescent material which exhibits blue or green and whose emission spectrum has a peak wavelength at greater than or equal to 450 nm and less than or equal to 570 nm, the following substances can be given.

For example, organometallic complexes having a 4H-triazole skeleton, such as tris{2-[5-(2-methylphenyl)-4-(2,6-dimethylphenyl)-4H-1,2,4-triazol-3-yl-κN$^2$]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole skeleton, such as tris[3-methyl-1-(2-methylphenyl)-5-phenyl-1H-1,2,4-triazolato]iridium(III) (abbreviation: [Ir(Mptzi-mp)$_3$]) and tris(1-methyl-5-phenyl-3-propyl-H-1,2,4-triazolato)iridium(III) (abbreviation: [Ir(PrptzI-Me)$_3$]); organometallic complexes having an imidazole skeleton, such as fac-tris[1-(2,6-diisopropylphenyl)-2-phenyl-H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and organometallic complexes in which a phenylpyridine derivative having an electron-withdrawing group is a ligand, such as bis[2-(4',6'-difluorophenyl)pyridinato-N,C$^2$']iridium(III) tetrakis(1-pyrazolyl)borate (abbreviation: FIr6), bis[2-(4',6'-difluorophenyl)pyridinato-N,C$^2$']iridium(III) picolinate (abbreviation: FIrpic), bis{2-[3',5'-bis(trifluoromethyl)phenyl]pyridinato-N,C$^2$'}iridium(III) picolinate (abbreviation: [Ir(CF$_3$ppy)$_2$(pic)]), and bis[2-(4',6'-difluorophenyl)pyridinato-N,C$^2$']iridium(III) acetylacetonate (abbreviation: FIr(acac)) can be given.

As examples of a phosphorescent material which exhibits green or yellow and whose emission spectrum has a peak wavelength at greater than or equal to 495 nm and less than or equal to 590 nm, the following substances can be given.

Examples of the phosphorescent material include organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato)bis{4,6-dimethyl-2-[6-(2,6-dimethylphenyl)-4-pyrimidinyl-κN$^3$]phenyl-κC}iridium(III) (abbreviation: [Ir(dmppm-dmp)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^2$')iridium(III) (abbreviation: [Ir(ppy)$_3$]), bis(2-phenylpyridinato-N,C$^2$')iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^2$')iridium(III) (abbreviation: [Ir(pq)$_3$]), bis(2-phenylquinolinato-N,C$^2$')iridium(III) acetylacetonate (abbreviation: [Ir(pq)$_2$(acac)]), [2-(4-phenyl-2-pyridinyl-κN)phenyl-κC]bis[2-(2-pyridinyl-κN)phenyl-κC]iridium(III) (abbreviation: [Ir(ppy)$_2$(4dppy)]), and bis[2-(2-pyridinyl-κN)phenyl-κC][2-(4-methyl-5-phenyl-2-pyridinyl-κN)phenyl-κC]; organometallic complexes such as bis(2,4-diphenyl-1,3-oxazolato-N,C$^2$')iridium(III) acetylacetonate (abbreviation: [Ir(dpo)$_2$(acac)]), bis{2-[4'-(perfluorophenyl)phenyl]pyridinato-N,C$^2$'}iridium(III) acetylacetonate (abbreviation: [Ir(p-PF-ph)$_2$(acac)]), and bis(2-phenylbenzothiazolato-N,C$^2$')iridium(III) acetylacetonate (abbreviation: [Ir(bt)$_2$(acac)]); and a rare earth metal complex such as tris(acetylacetonato)(monophenanthroline)terbium(III)(abbreviation: [Tb(acac)$_3$(Phen)]).

As examples of a phosphorescent material which exhibits yellow or red and whose emission spectrum has a peak wavelength at greater than or equal to 570 nm and less than or equal to 750 nm, the following substances can be given.

For example, organometallic complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), bis[4,6-di(naphthalen-1-yl)pyrimidinato](dipivaloylmethanato)iridium(III) (abbreviation: [Ir(d1npm)$_2$(dpm)]), and tris(4-t-butyl-6-phenylpyrimidinato)iridium(III) (abbreviation: [Ir(tBuppm)$_3$]); organometallic complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), bis{4,6-dimethyl-2-[3-(3,5-dimethylphenyl)-5-phenyl-2-pyrazinyl-κN]phenyl-κC}(2,6-dimethyl-3,5-heptanedionato-κ$^2$O,O')iridium(III) (abbreviation: [Ir(dmdppr-P)$_2$(dibm)]), bis{4,6-dimethyl-2-[5-(4-cyano-2,6-dimethylphenyl)-3-(3,5-dimethylphenyl)-2-pyrazinyl-κN]phenyl-κC}(2,2,6,6-tetramethyl-3,5-heptanedionato-κ2O,O')iridium(III) (abbreviation: [Ir(dmdppr-dmCP)$_2$(dpm)]), (acetylacetonato)bis[2-methyl-3-phenylquinoxalinato-N,C$^2$']iridium(III) (abbreviation: [Ir (mpq)₂(acac)]), (acetylacetonato)bis(2,3-diphenylquinoxalinato-N,C²')iridium(III) (abbreviation: [Ir(dpq)₂(acac)]), (acetylacetonato)bis[2,3-bis(4-fluorophenyl)quinoxalinato]iridium(III) (abbreviation: [Ir(Fdpq)₂(acac)]), and bis{4,6-dimethyl-2-[5-(5-cyano-2-methylphenyl)-3-(3,5-dimethylphenyl)-2-pyrazinyl-κN]phenyl-κC}(2,2,6,6-tetramethyl-3,5-heptanedionato-κ²O,O')iridium(III) (abbreviation: [Ir(dmdppr-m⁵CP)₂(dpm)]); organometallic complexes having a pyridine skeleton, such as tris(1-phenylisoquinolinato-N,C²')iridium(III) (abbreviation: [Ir(piq)₃]), bis(1-phenylisoquinolinato-N,C²')iridium(III) acetylacetonate (abbreviation: [Ir(piq)₂(acac)]), and bis[4,6-dimethyl-2-(2-quinolinyl-κN)phenyl-κC] (2,4-pentanedionato-κ²O,O')iridium(III); platinum complexes such as 2,3,7,8,12,13,17,18-octaethyl-21H,23H-porphyrin platinum(II) (abbreviation: [PtOEP]); and rare earth metal complexes, such as tris(1,3-diphenyl-1,3-propanedionato) (monophenanthroline)europium(III) (abbreviation: [Eu(DBM)₃(Phen)]) and tris[1-(2-thenoyl)-3,3,3-trifluoroacetonato](monophenanthroline)europium(III) (abbreviation: [Eu(TTA)₃(Phen)]), can be given.

As the compounds (the host material and the assist material) used in the light-emitting layer 113, one or more kinds of substances having a larger energy gap than the light-emitting substance has can be used.

In the case where the light-emitting substance used in the light-emitting layer 113 is a fluorescent material, an organic compound used in combination with the light-emitting substance is preferably an organic compound that has a high energy level in a singlet excited state and has a low energy level in a triplet excited state.

In terms of a preferable combination with a light-emitting substance (a fluorescent material or a phosphorescent material), specific examples of the organic compounds are shown below though some of them overlap the specific examples shown above.

In the case where the light-emitting substance is a fluorescent material, examples of the organic compound that can be used in combination with the light-emitting substance include condensed polycyclic aromatic compounds, such as an anthracene derivative, a tetracene derivative, a phenanthrene derivative, a pyrene derivative, a chrysene derivative, and a dibenzo[g,p]chrysene derivative.

Specific examples of the organic compound that is used in combination with the fluorescent material include 9-phenyl-3-[4-(10-phenyl-9-anthryl)phenyl]-9H-carbazole (abbreviation: PCzPA), 3,6-diphenyl-9-[4-(10-phenyl-9-anthryl)phenyl]-9H-carbazole (abbreviation: DPCzPA), PCPN, 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 6,12-dimethoxy-5,11-diphenylchrysene, N,N,N',N',N'',N'',N''',N'''-octaphenyldibenzo[g,p]chrysene-2,7,10,15-tetraamine (abbreviation: DBC1), CzPA, 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan(abbreviation: 2mBnfPPA), 9-phenyl-10-{4-(9-phenyl-9H-fluoren-9-yl)biphenyl-4'-yl}anthracene (abbreviation: FLPPA), 9,10-bis(3,5-diphenylphenyl)anthracene(abbreviation:DPPA),9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), 5,12-diphenyltetracene, and 5,12-bis(biphenyl-2-yl)tetracene.

In the case where the light-emitting substance is a phosphorescent material, as the organic compound that is used in combination with the light-emitting substance, an organic compound having triplet excitation energy (an energy difference between a ground state and a triplet excited state) which is higher than that of the light-emitting substance is selected.

In the case where a plurality of organic compounds (e.g., a first host material and a second host material (or an assist material) are used in combination with a light-emitting substance in order to form an exciplex, the plurality of organic compounds are preferably mixed with a phosphorescent material (particularly, an organometallic complex).

With such a structure, light emission can be efficiently obtained by exciplex-triplet energy transfer (ExTET), which is energy transfer from an exciplex to a light-emitting substance. Note that a combination of the plurality of organic compounds that easily forms an exciplex is preferably employed, and it is particularly preferable to combine a compound that easily accepts holes (hole-transport material) and a compound that easily accepts electrons (electron-transport material). The organic compound of one embodiment of the present invention described in Embodiment 1 is suitable as the compound that easily accepts holes. As the hole-transport material and the electron-transport material, specifically, any of the materials described in this embodiment can be used. With the above structure, high efficiency, low-voltage driving, and a long lifetime of a light-emitting device can be achieved at the same time.

In the case where the light-emitting substance is a phosphorescent material, examples of the organic compound that can be used in combination with the light-emitting substance include an aromatic amine, a carbazole derivative, a dibenzothiophene derivative, a dibenzofuran derivative, a zinc- or aluminum-based metal complex, an oxadiazole derivative, a triazole derivative, a benzimidazole derivative, a quinoxaline derivative, a dibenzoquinoxaline derivative, a pyrimidine derivative, a triazine derivative, a pyridine derivative, a bipyridine derivative, and a phenanthroline derivative.

Among the above-described compounds, specific examples of the aromatic amine, (a compound having an aromatic amine skeleton), the carbazole derivative, the dibenzothiophene derivative (a thiophene derivative), and the dibenzofuran derivative (a furan derivative), which are organic compounds having a high hole-transport property, are the same as the compounds given above as specific examples of the hole-transport material.

Specific examples of zinc- and aluminum-based metal complexes, which are organic compounds having a high electron-transport property, include metal complexes having a quinoline skeleton or a benzoquinoline skeleton, such as tris(8-quinolinolato)aluminum(III) (abbreviation: Alq), tris(4-methyl-8-quinolinolato)aluminum(III) (abbreviation: Almq₃), bis(10-hydroxybenzo[h]quinolinato)beryllium(II) (abbreviation: BeBq2), bis(2-methyl-8-quinolinolato)(4-phenylphenolato)aluminum(III) (abbreviation: BAlq), and bis(8-quinolinolato)zinc(II) (abbreviation: Znq).

Alternatively, a metal complex having an oxazole-based or thiazole-based ligand, such as bis[2-(2-benzoxazolyl)

phenolato]zinc(II) (abbreviation: ZnPBO) or bis[2-(2-benzothiazolyl)phenolato]zinc(II) (abbreviation: ZnBTZ), can be used.

Specific examples of an oxadiazole derivative, a triazole derivative, a benzimidazole derivative, a quinoxaline derivative, a dibenzoquinoxaline derivative, and a phenanthroline derivative, which are organic compounds having a high electron-transport property, include 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 3-(4-biphenylyl)-4-phenyl-5-(4-tert-butylphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), 2,2',2"-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), 4,4'-bis(5-methylbenzoxazol-2-yl)stilbene (abbreviation: BzOS), bathophenanthroline (abbreviation: BPhen), bathocuproine (abbreviation: BCP), 2,9-bis(naphthalen-2-yl)-4,7-diphenyl-1,10-phenanthroline (abbreviation: NBPhen), 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

Specific examples of a heterocyclic compound having a diazine skeleton, a heterocyclic compound having a triazine skeleton, and a heterocyclic compound having a pyridine skeleton, which are organic compounds having a high electron-transport property, include 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), 4,6-bis[3-(9H-carbazol-9-yl)phenyl]pyrimidine (abbreviation: 4,6mCzP2Pm), 2-{4-[3-(N-phenyl-9H-carbazol-3-yl)-9H-carbazol-9-yl]phenyl}-4,6-diphenyl-1,3,5-triazine (abbreviation: PCCzPTzn), 9-[3-(4,6-diphenyl-1,3,5-triazin-2-yl)phenyl]-9'-phenyl-2,3'-bi-9H-carbazole (abbreviation: mPCCzPTzn-02), 2-[3'-(9,9-dimethyl-9H-fluorene-2-yl)-1,1'-biphenyl-3-yl]-4,6-diphenyl-1,3,5-triazine (abbreviation: mFBPTzn), 2-[(1,1'-biphenyl)-4-yl]-4-phenyl-6-[9,9'-spirobi(9H-fluoren)-2-yl]-1,3,5-triazine (abbreviation: BP-SFTzn), 2-{3-[3-(benzo[b]naphtho[1,2-d]furan-8-yl)phenyl]phenyl}-4,6-diphenyl-1,3,5-triazine (abbreviation: mBnfBPTzn), 2-{3-[3-(benzo[b]naphtho[1,2-d]furan-6-yl)phenyl]phenyl}-4,6-diphenyl-1,3,5-triazine (abbreviation: mBnfBPTzn-02), 3,5-bis(3-(9H-carbazol-9-yl)phenyl)pyridine (abbreviation: 35DCzPPy), and 1,3,5-tri[3-(3-pyridyl)phenyl]benzene (abbreviation: TmPyPB).

As an organic compound having a high electron-transport property, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can also be used.

The TADF material is a material that can up-convert a triplet excited state into a singlet excited state (reverse intersystem crossing) using a little thermal energy and efficiently exhibits light emission (fluorescence) from the singlet excited state. The thermally activated delayed fluorescence is efficiently obtained under the condition where the difference in energy between the triplet excited level and the singlet excited level is greater than or equal to 0 eV and less than or equal to 0.2 eV, preferably greater than or equal to 0 eV and less than or equal to 0.1 eV. Note that delayed fluorescence by the TADF material refers to light emission having the same spectrum as normal fluorescence and an extremely long lifetime. The lifetime is $10^{-6}$ seconds or longer, preferably $10^{-3}$ seconds or longer.

Examples of the TADF material include fullerene, a derivative thereof, an acridine derivative such as proflavine, and eosin. Other examples include a metal-containing porphyrin such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (abbreviation: $SnF_2$(Proto IX)), a mesoporphyrin-tin fluoride complex (abbreviation: $SnF_2$(Meso IX)), a hematoporphyrin-tin fluoride complex (abbreviation: $SnF_2$(Hemato IX)), a coproporphyrin tetramethyl ester-tin fluoride complex (abbreviation: $SnF_2$(Copro III-4Me)), an octaethylporphyrin-tin fluoride complex (abbreviation: $SnF_2$(OEP)), an etioporphyrin-tin fluoride complex (abbreviation: $SnF_2$(Etio I)), and an octaethylporphyrin-platinum chloride complex (abbreviation: $PtCl_2OEP$).

It is also possible to use a heterocyclic compound having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), PCCzPTzn, 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA). Note that a substance in which a π-electron rich heteroaromatic ring is directly bonded to a π-electron deficient heteroaromatic ring is particularly preferable because both the donor property of the π-electron rich heteroaromatic ring and the acceptor property of the π-electron deficient heteroaromatic ring are improved and the energy difference between the singlet excited state and the triplet excited state becomes small.

Note that the TADF material can also be used in combination with another organic compound. In particular, the TADF material can be used in combination with the host material, the hole-transport material, or the electron-transport material which are described above.

Furthermore, when used in combination with a low molecular material or a high molecular material, the above materials can be used to form the light-emitting layer 113. For the film formation, a known method (an evaporation method, a coating method, a printing method, or the like) can be used as appropriate.

<Electron-Transport Layer>

The electron-transport layer 114 transports electrons injected from the second electrode 102 through the electron-injection layer 115 to the light-emitting layer 113. Note that the electron-transport layer 114 contains an electron-transport material. It is preferable that the electron-transport material contained in the electron-transport layer 114 be a substance with an electron mobility of higher than or equal to $1 \times 10^{-6}$ cm$^2$/Vs. Note that any other substance can also be used as long as the substance transports electrons more easily than it transports holes.

As the electron-transport material, any of the following materials having a high electron-transport property can be used, for example: a metal complex having a quinoline skeleton, a metal complex having a benzoquinoline skeleton, a metal complex having an oxazole skeleton, a metal complex having a thiazole skeleton, an oxadiazole derivative, a triazole derivative, an imidazole derivative, an oxazole derivative, a thiazole derivative, a phenanthroline derivative, a quinoline derivative having a quinoline ligand, a benzoquinoline derivative, a quinoxaline derivative, a dibenzoquinoxaline derivative, a pyridine derivative, a bipyridine derivative, a pyrimidine derivative, and a π-electron deficient heteroaromatic compound such as a nitrogen-containing heteroaromatic compound.

As specific examples of the electron-transport material, the above-described materials can be used.

<Electron-Injection Layer>

The electron-injection layer 115 is a layer containing a material having a high electron-injection property. For the electron-injection layer 115, an alkali metal, an alkaline earth metal, or a compound thereof such as lithium fluoride (LiF), cesium fluoride (CsF), calcium fluoride ($CaF_2$), or lithium oxide ($LiO_x$) can be used. A rare earth metal compound like erbium fluoride ($ErF_3$) can also be used. In addition, an electride may be used for the electron-injection layer 115. As an example of the electride, a substance in which electrons are added at high concentration to calcium oxide-aluminum oxide is given. Any of the above-described substances for forming the electron-transport layer 114 can also be used.

Alternatively, for the electron-injection layer 115, a composite material containing an electron-transport material and a donor material (an electron-donating material) may be used. Such a composite material is excellent in an electron-injection property and an electron-transport property because electrons are generated in the organic compound by the electron donor. The organic compound here is preferably a material excellent in transporting the generated electrons; specifically, for example, the above-described electron-transport materials for the electron-transport layer 114 (e.g., a metal complex or a heteroaromatic compound) can be used. As the electron donor, a substance showing an electron-donating property with respect to an organic compound is used. Specifically, an alkali metal, an alkaline earth metal, and a rare earth metal are preferable, and lithium, cesium, magnesium, calcium, erbium, ytterbium, and the like are given. In addition, an alkali metal oxide and an alkaline earth metal oxide are preferable, and lithium oxide, calcium oxide, barium oxide, and the like are given. Alternatively, a Lewis base such as magnesium oxide can be used. Further alternatively, an organic compound such as tetrathiafulvalene (abbreviation: TTF) can be used.

<Charge-Generation Layer>

In the light-emitting device in FIG. 1C, the charge-generation layer 104 has a function of injecting electrons into the EL layer 103a and injecting holes into the EL layer 103b when voltage is applied between the first electrode 101 (anode) and the second electrode 102 (cathode).

The charge-generation layer 104 may contain a hole-transport material and an acceptor material (electron-accepting material) or may contain an electron-transport material and a donor material. The charge-generation layer 104 with such constituents can suppress an increase in driving voltage caused by stacking EL layers.

As the hole-transport material, the acceptor material, the electron-transport material, and the donor material, the above-described materials can be used.

For fabrication of the light-emitting device described in this embodiment, a vacuum process such as an evaporation method or a solution process such as a spin coating method or an ink-jet method can be used. When an evaporation method is used, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the functional layers (the hole-injection layer, the hole-transport layers, the light-emitting layer, the electron-transport layers, and the electron-injection layer) included in the EL layer and the charge-generation layer can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, or micro-contact printing), or the like.

Materials of the functional layers and the charge-generation layer included in the EL layer 103 are not limited to the above-described corresponding materials. For example, as the material of the functional layer, a high-molecular compound (e.g., an oligomer, a dendrimer, and a polymer), a middle molecular compound (a compound between a low molecular compound and a high-molecular compound with a molecular weight of 400 to 4000), or an inorganic compound (e.g., a quantum dot material) may be used. The quantum dot material may be a colloidal quantum dot material, an alloyed quantum dot material, a core-shell quantum dot material, a core quantum dot material, or the like.

This embodiment can be combined with the other embodiment as appropriate.

Embodiment 3

In this embodiment, light-emitting apparatuses of embodiments of the present invention will be described with reference to FIGS. 2A to 2C, FIGS. 3A to 3C, FIGS. 4A and 4B, and FIGS. 5A to 5D.

Structure Example 1 of Light-Emitting Apparatus

Figure 2A:
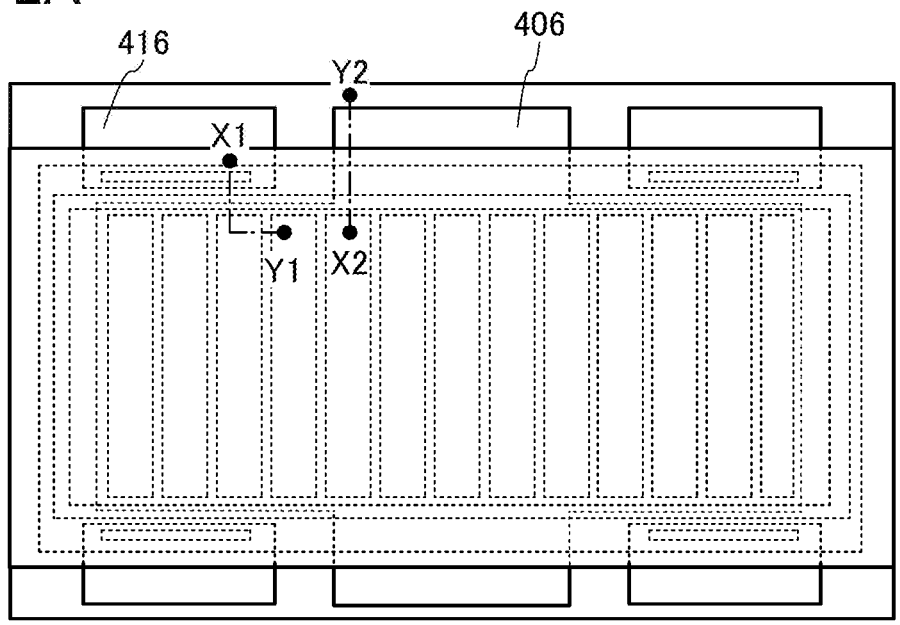
FIG. 2A is a top view illustrating an example of a light-emitting apparatus.
Figure 2B:
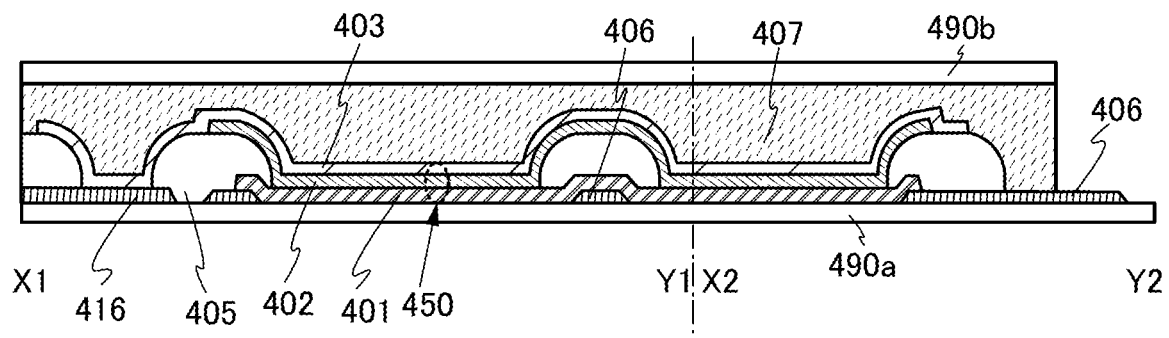
FIGS. 2B and 2C are cross-sectional views illustrating examples of light-emitting apparatuses.
Figure 2C:
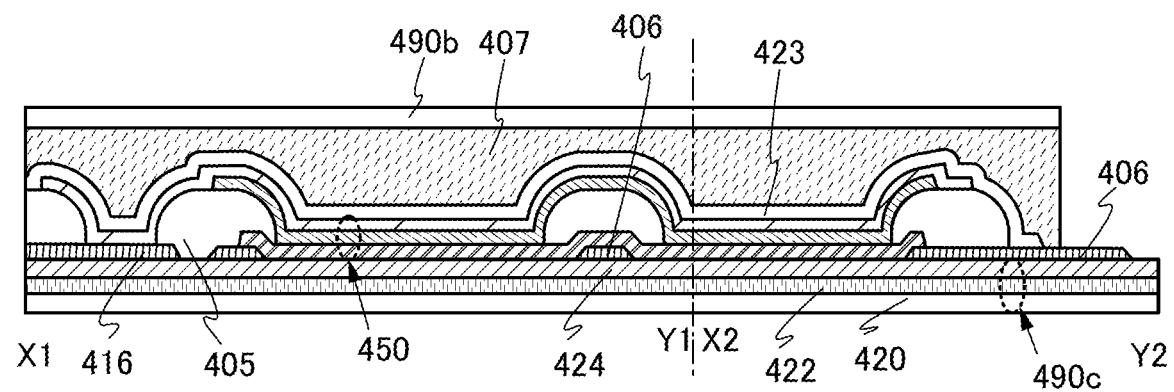

FIG. 2A is a top view of a light-emitting apparatus, FIGS. 2B and 2C are cross-sectional views taken along dashed-dotted lines X1-Y1 and X2-Y2 in FIG. 2A. The light-emitting apparatus in FIGS. 2A to 2C can be used as a lighting device, for example. The light-emitting apparatus may have a bottom-emission structure, a top-emission structure, or a dual-emission structure.

The light-emitting apparatus illustrated in FIG. 2B includes a substrate 490a, a substrate 490b, a conductive layer 406, a conductive layer 416, an insulating layer 405, an organic EL device 450 (a first electrode 401, an EL layer 402, and a second electrode 403), and an adhesive layer 407. The organic EL device 450 can also be referred to as a light-emitting element, an organic EL element, a light-emitting device, or the like. The EL layer 402 preferably includes the organic compound of one embodiment of the present invention described in Embodiment 1. For example, the organic compound is preferably included as at least one of the material of the hole-injection layer, the material of the hole-transport layer, and the host material of the light-emitting layer.

The organic EL device 450 includes the first electrode 401 over the substrate 490a, the EL layer 402 over the first electrode 401, and the second electrode 403 over the EL layer 402. The organic EL device 450 is sealed by the substrate 490a, the adhesive layer 407, and the substrate 490b.

End portions of the first electrode 401, the conductive layer 406, and the conductive layer 416 are covered with the insulating layer 405. The conductive layer 406 is electrically connected to the first electrode 401, and the conductive layer 416 is electrically connected to the second electrode 403. The conductive layer 406 covered with the insulating layer 405 with the first electrode 401 positioned therebetween functions as an auxiliary wiring and is electrically connected to the first electrode 401. It is preferable that the auxiliary wiring be electrically connected to the electrode of the organic EL device 450, in which case a voltage drop due to the resistance of the electrode can be inhibited. The conductive layer 406 may be provided over the first electrode 401. Furthermore, an auxiliary wiring that is electrically connected to the second electrode 403 may be provided, for example, over the insulating layer 405.

For the substrate 490a and the substrate 490b, glass, quartz, ceramic, sapphire, an organic resin, or the like can be used. When the substrate 490a and the substrate 490b are formed using a flexible material, the flexibility of the display device can be increased.

A light-emitting surface of the light-emitting apparatus may be provided with a light extraction structure for increasing the light extraction efficiency, an antistatic film preventing the attachment of a foreign substance, a water repellent film suppressing the attachment of stain, a hard coat film suppressing generation of a scratch in use, an impact absorption layer, or the like.

Examples of insulating materials that can be used for the insulating layer 405 include a resin material such as an acrylic resin and an epoxy resin, and an inorganic insulating material such as silicon oxide, silicon oxynitride, silicon nitride oxide, silicon nitride, and aluminum oxide.

As the adhesive layer 407, a variety of curable adhesives such as a reactive curable adhesive, a thermosetting adhesive, an anaerobic adhesive, and a photocurable adhesive such as an ultraviolet curable adhesive can be used. Examples of these adhesives include an epoxy resin, an acrylic resin, a silicone resin, a phenol resin, a polyimide resin, an imide resin, a polyvinyl chloride (PVC) resin, a polyvinyl butyral (PVB) resin, and an ethylene vinyl acetate (EVA) resin. In particular, a material with low moisture permeability, such as an epoxy resin, is preferred. A two-component-mixture-type resin may be used. An adhesive sheet or the like may be used.

The light-emitting apparatus illustrated in FIG. 2C includes a barrier layer 490c, the conductive layer 406, the conductive layer 416, the insulating layer 405, the organic EL device 450, the adhesive layer 407, the barrier layer 423, and the substrate 490b.

The barrier layer 490c illustrated in FIG. 2C includes a substrate 420, an adhesive layer 422, and an insulating layer 424 having a high barrier property.

In the light-emitting apparatus illustrated in FIG. 2C, the organic EL device 450 is provided between the insulating layer 424 having a high barrier property and the barrier layer 423. Thus, even when resin films with relatively-low water resistance or the like are used as the substrate 420 and the substrate 490b, impurities such as water can be prevented from entering the organic EL device, that is, a reduction in lifetime can be suppressed.

For the substrate 420 and the substrate 490b, any of the following can be used, for example: polyester resins such as polyethylene terephthalate (PET) and polyethylene naphthalate (PEN), a polyacrylonitrile resin, an acrylic resin, a polyimide resin, a polymethyl methacrylate resin, a polycarbonate (PC) resin, a polyethersulfone (PES) resin, polyamide resins (e.g., nylon and aramid), a polysiloxane resin, a cycloolefin resin, a polystyrene resin, a polyamide-imide resin, a polyurethane resin, a polyvinyl chloride resin, a polyvinylidene chloride resin, a polypropylene resin, a polytetrafluoroethylene (PTFE) resin, an ABS resin, and cellulose nanofiber. Glass that is thin enough to have flexibility may be used for the substrate 420 and the substrate 490b.

As the insulating layer 424 having a high barrier property, an inorganic insulating film is preferably used. As the inorganic insulating film, a silicon nitride film, a silicon oxynitride film, a silicon oxide film, a silicon nitride oxide film, an aluminum oxide film, or an aluminum nitride film can be used, for example. A hafnium oxide film, an yttrium oxide film, a zirconium oxide film, a gallium oxide film, a tantalum oxide film, a magnesium oxide film, a lanthanum oxide film, a cerium oxide film, a neodymium oxide film, or the like may be used. A stack including two or more of the above insulating films may also be used.

The barrier layer 423 preferably includes at least single-layer inorganic film. For example, the barrier layer 423 can have a single-layer structure of an inorganic film or a stacked structure of an inorganic film and an organic film. As the inorganic film, the above-described inorganic insulating film is preferably used. As the stacked structure, for example, a structure in which a silicon oxynitride film, a silicon oxide film, an organic film, a silicon oxide film, and a silicon nitride film are formed sequentially is given. When the barrier layer has a stacked structure of an inorganic film and an organic film, entry of an impurity that can enter the organic EL device 450 (typically, hydrogen, water, or the like) can be suitably prevented.

The insulating layer 424 having a high barrier property and the organic EL device 450 can be directly formed on the substrate 420 having flexibility. In that case, the adhesive layer 422 is not necessary. Alternatively, the insulating layer 424 and the organic EL device 450 can be formed over a rigid substrate with a separation layer provided therebetween and then transferred to the substrate 420. For example, the insulating layer 424 and the organic EL device 450 may be transferred to the substrate 420 in the following manner: the insulating layer 424 and the organic EL device 450 are separated from the rigid substrate by applying heat, force, laser light, or the like to the separation layer, and the insulating layer 424 and the organic EL device 450 are bonded to the substrate 420 with the use of the adhesive layer 422. For the separation layer, a stacked structure including inorganic films such as a tungsten film and a silicon oxide film, or an organic resin film of polyimide or the like can be used, for example. In the case where a rigid substrate is used, the insulating layer 424 can be formed at high temperature as compared with the case where a resin substrate or the like is used; thus, the insulating layer 424 can have high density and an excellent barrier property.

Structure Example 2 of Light-Emitting Apparatus

Figure 3A:
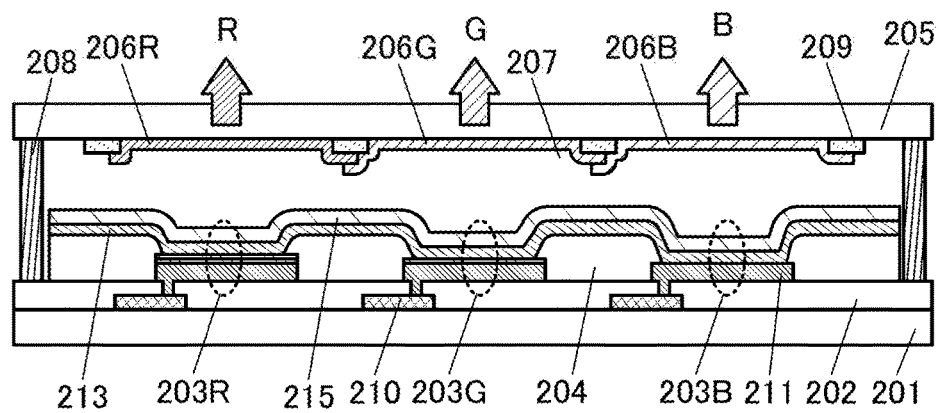
FIGS. 3A and 3C are cross-sectional views illustrating examples of light-emitting apparatuses.

FIG. 3A is a cross-sectional view of a light-emitting apparatus. The light-emitting apparatus illustrated in FIG.

3A is an active-matrix light-emitting apparatus in which a transistor is electrically connected to a light-emitting device.

The light-emitting apparatus illustrated in FIG. 3A includes a substrate 201, a transistor 210, a light-emitting device 203R, a light-emitting device 203G, a light-emitting device 203B, a color filter 206R, a color filter 206G, a color filter 206B, a substrate 205, and the like.

In FIG. 3A, the transistor 210 is provided over the substrate 201, the insulating layer 202 is provided over the transistor 210, and the light-emitting devices 203R, 203G, and 203B are provided over the insulating layer 202.

The transistor 210 and the light-emitting devices 203R, 203G, and 203B are sealed in a space 207 surrounded by the substrate 201, the substrate 205, and the adhesive layer 208. The space 207 can be filled with, for example, a reduced-pressure atmosphere, an inert atmosphere, or a resin.

In the light-emitting apparatus illustrated in FIG. 3A, one pixel includes a red subpixel (R), a green subpixel (G), and a blue subpixel (B).

The light-emitting apparatus of one embodiment of the present invention includes a plurality of pixels arranged in a matrix. One pixel includes at least one subpixel. One subpixel includes one light-emitting device. For example, one pixel can include three subpixels (e.g., three colors of R, G, and B or three colors of yellow (Y), cyan (C), and magenta (M)) or four subpixels (e.g., four colors of R, G, B, and white (W) or four colors of R, G, B, and Y).

Figure 3B:
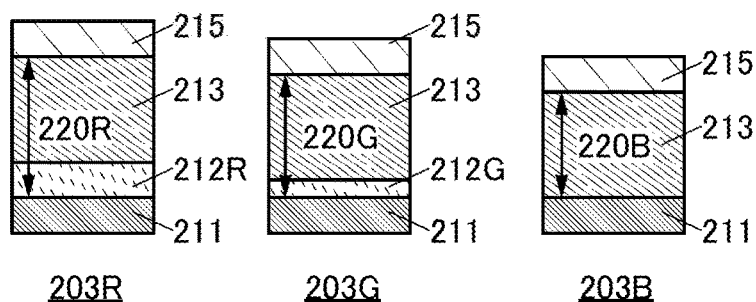
FIG. 3B is a cross-sectional view illustrating examples of light-emitting devices.

FIG. 3B illustrates specific structures of the light-emitting device 203R, the light-emitting device 203G, and the light-emitting device 203B. The light-emitting devices 203R, 203G, and 203B include the same EL layer 213, and have microcavity structures in which the optical path length between electrodes of each light-emitting device is adjusted in accordance with the emission color of the light-emitting device. The EL layer 213 preferably includes the organic compound of one embodiment of the present invention described in Embodiment 1. For example, it is preferable that the organic compound be included as at least one of the material of the hole-injection layer, the material of the hole-transport layer, and the host material of the light-emitting layer.

The first electrode 211 functions as a reflective electrode and the second electrode 215 functions as a transflective electrode.

In the light-emitting device 203R, the optical path length between the first electrode 211 and the second electrode 215 is adjusted to be an optical path length 220R in order to enhance the intensity of red light. Similarly, in the light-emitting device 203G, the optical path length between the first electrode 211 and the second electrode 215 is adjusted to be an optical path length 220G in order to enhance the intensity of green light. In the light-emitting device 203B, the optical path length between the first electrode 211 and the second electrode 215 is adjusted to be an optical path length 220B in order to enhance the intensity of blue light.

As illustrated in FIG. 3B, a conductive layer 212R is formed over the first electrode 211 in the light-emitting device 203R and a conductive layer 212G is formed over the first electrode 211 in the light-emitting device 203G, whereby optical adjustment can be performed. Furthermore, in the light-emitting device 203B, the optical path length 220B may be adjusted by forming a conductive layer whose thickness is different from those of the conductive layer 212R and the conductive layer 212G over the first electrode 211. Note that as shown in FIG. 3A, end portions of the first electrode 211, the conductive layer 212R, and the conductive layer 212G are covered with an insulating layer 204.

The light-emitting apparatus illustrated in FIG. 3A has a top-emission structure, which emits light obtained from the light-emitting devices through color filters formed on the substrate 205. Each of the color filters transmits visible light in a specific wavelength range and blocks visible light in a specific wavelength range.

In the red subpixel (R), light from the light-emitting device 203R is emitted through the red color filter 206R. As illustrated in FIG. 3A, the color filter 206R that transmits only light in the red wavelength range is provided in a position overlapping with the light-emitting device 203R, whereby red light emission can be obtained from the light-emitting device 203R.

Similarly, in the green subpixel (G), light from the light-emitting device 203G is emitted through the green color filter 206G, and in the blue subpixel (B), light from the light-emitting device 203B is emitted through the blue color filter 206B.

Note that the substrate 205 may be provided with a black matrix (also referred to as a black layer) 209. In that case, end portions of the color filters and the black matrix 209 preferably overlap with each other. Furthermore, the color filters for the respective colors and the black matrix 209 may be covered with an overcoat layer that transmits visible light.

Figure 3C:
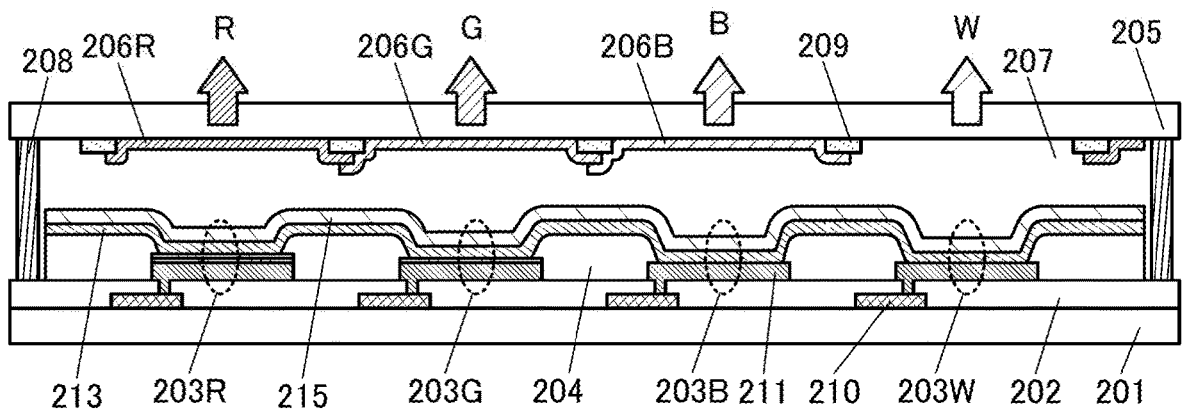

In the light-emitting apparatus illustrated in FIG. 3C, one pixel includes the red subpixel (R), the green subpixel (G), the blue subpixel (B), and a white subpixel (W). In FIG. 3C, light from a light-emitting device 203W included in the white subpixel (W) is emitted to the outside of the light-emitting apparatus without passing through a color filter.

Note that the optical path length between the first electrode 211 and the second electrode 215 in the light-emitting device 203W may be the same as the optical path length in any one of the light-emitting devices 203R, 203G, and 203B or may be different from the optical path lengths in the light-emitting devices 203R, 203G, and 203B.

In the case where the intensity of blue light is desired to be enhanced, for example, in the case where light emitted from the light-emitting device 203W is white light with a low color temperature, the optical path length in the light-emitting device 203W is preferably equal to the optical path length 220B in the light-emitting device 203B, as illustrated in FIG. 3C. Thus, light obtained from the light-emitting device 203W can be made closer to white light with a desired color temperature.

Figure 4A:
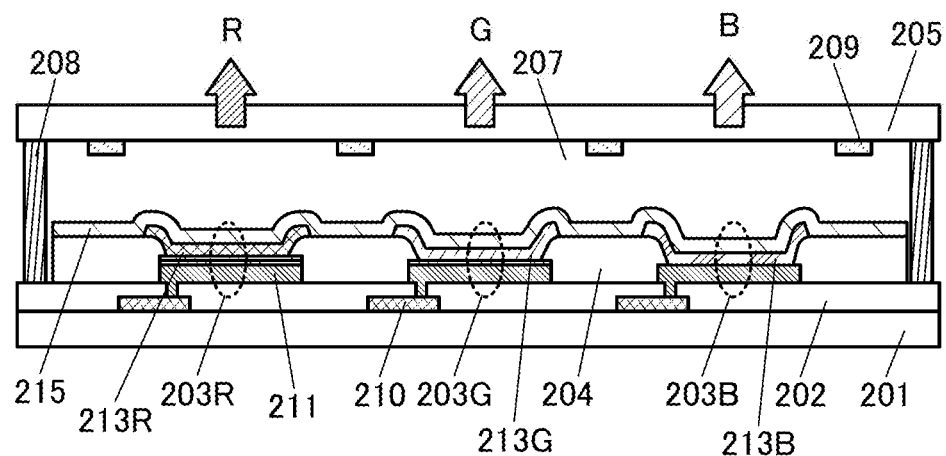
FIGS. 4A and 4B are cross-sectional views illustrating examples of light-emitting apparatuses.

Although FIG. 3A illustrates an example in which the light-emitting devices in the subpixels use the same EL layer 213, different EL layers may be used for the light-emitting devices in the subpixels as illustrated in FIG. 4A. The above-described microcavity structure can also be applied to FIG. 4A.

FIG. 4A illustrates an example in which the light-emitting device 203R includes an EL layer 213R, the light-emitting device 203G includes an EL layer 213G, and the light-emitting device 203B includes an EL layer 213B. The EL layers 213R, 213G, and 213B may include a common layer. For example, in the EL layers 213R, 213G, and 213B, the structures of the respective light-emitting layers may be different and the structures of the other layers may be the same. In FIG. 4A, light from the light-emitting devices 203R, 203G, and 203B may be emitted through a color filter or without passing through a color filter.

Figure 4B:
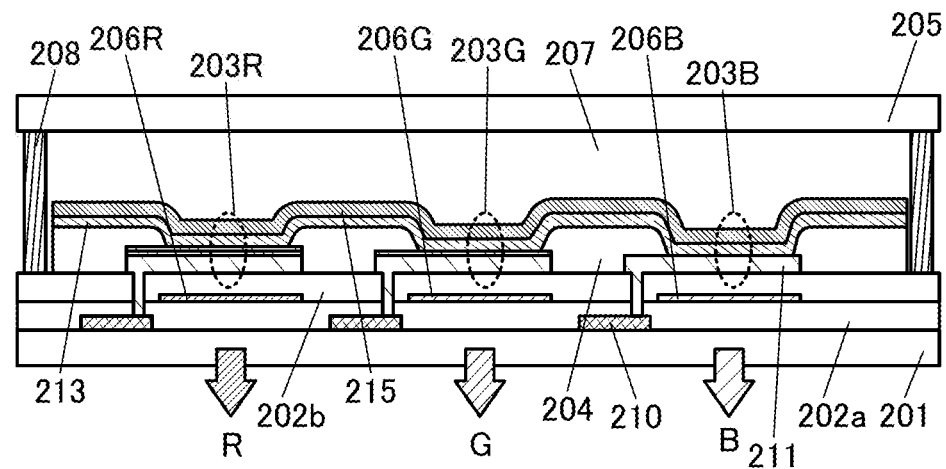

Although FIG. 3A illustrates a top-emission light-emitting apparatus, a light-emitting apparatus with a bottom-emission structure in which light is extracted to the substrate 201 side where the transistor 210 is formed as illustrated in FIG. 4B is also one embodiment of the present invention.

In the bottom-emission light-emitting apparatus, color filters for the respective colors are preferably provided between the substrate 201 and the light-emitting devices. In FIG. 4B, the transistor 210 is formed over the substrate 201, an insulating layer 202a is formed over the transistor 210, the color filters 206R, 206G, and 206B are formed over the insulating layer 202a, an insulating layer 202b is formed over the color filters 206R, 206G, and 206B, and the light-emitting devices 203R, 203G, and 203B are formed over the insulating layer 202b.

In the case of the top-emission light-emitting apparatus, a light-blocking substrate or a light-transmitting substrate can be used as the substrate 201, and a light-transmitting substrate can be used as the substrate 205.

In the case of the bottom-emission light-emitting apparatus, a light-blocking substrate or a light-transmitting substrate can be used as the substrate 205, and a light-transmitting substrate can be used as the substrate 201.

Structure Example 3 of Light-Emitting Apparatus

The light-emitting apparatus of one embodiment of the present invention can be of a passive matrix type or an active matrix type. An active-matrix light-emitting apparatus is described with reference to FIGS. 5A to 5D.

Figure 5A:
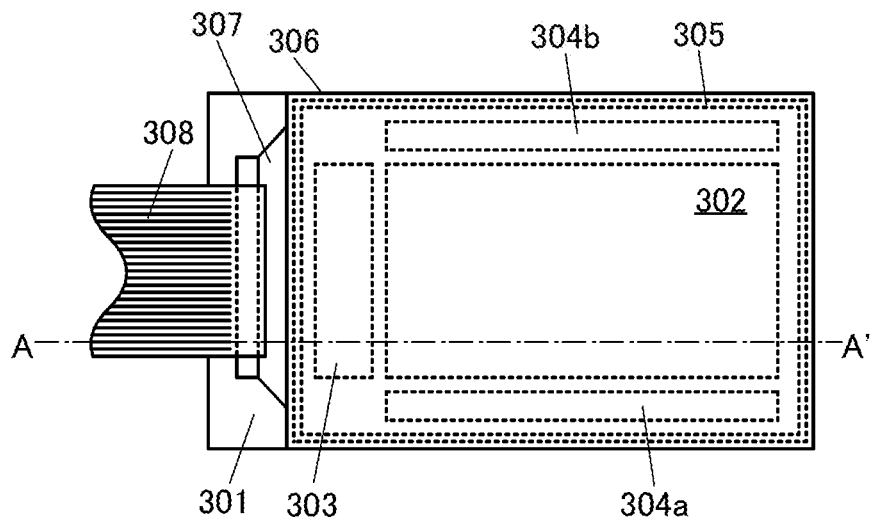
FIGS. 5A and 5B are a top view and a cross-sectional view, respectively, illustrating an example of a light-emitting apparatus.
Figure 5B:
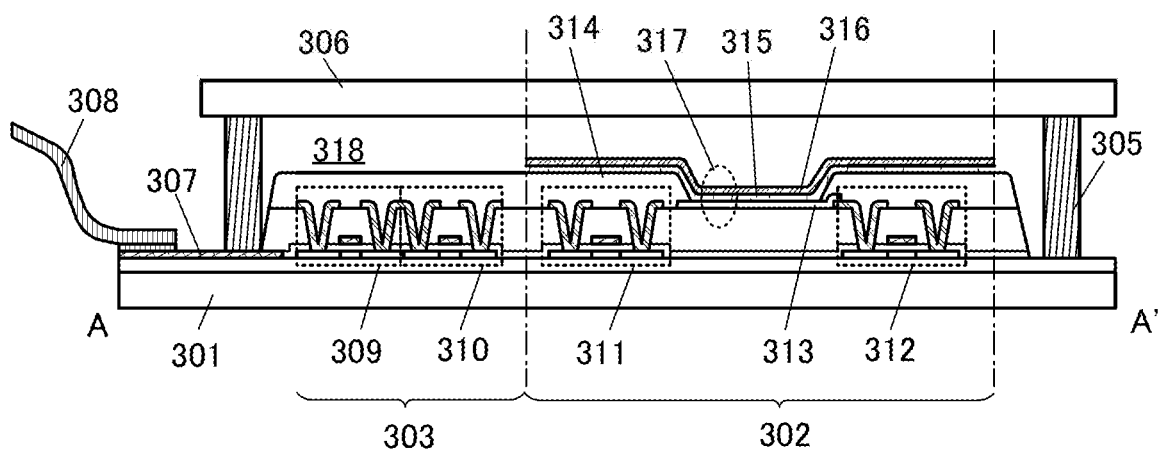

FIG. 5A is a top view of the light-emitting apparatus. FIG. 5B is a cross-sectional view taken along a dashed-dotted line A-A' in FIG. 5A.

The active-matrix light-emitting apparatus illustrated in FIGS. 5A and 5B includes a pixel portion 302, a circuit portion 303, a circuit portion 304a, and a circuit portion 304b.

Each of the circuit portions 303, 304a, and 304b functions as a scan line driver circuit (a gate driver) or a signal line driver circuit (a source driver). Alternatively, each of the circuit portions 303, 304a, and 304b may be a circuit that electrically connects the pixel portion 302 to an external gate driver or an external source driver.

A lead wiring 307 is provided over a first substrate 301. The lead wiring 307 is electrically connected to an FPC 308 that is an external input terminal. The FPC 308 transmits a signal (e.g., a video signal, a clock signal, a start signal, or a reset signal) or a potential from the outside to the circuit portion 303, the circuit portion 304a, and the circuit portion 304b. The FPC 308 may be provided with a printed wiring board (PWB). The structure illustrated in FIGS. 5A and 5B can also be referred to as a light-emitting module including a light-emitting device (or a light-emitting apparatus) and an FPC.

The pixel portion 302 includes a plurality of pixels each including an organic EL device 317, a transistor 311, and a transistor 312. The transistor 312 is electrically connected to a first electrode 313 included in the organic EL device 317. The transistor 311 functions as a switching transistor. The transistor 312 functions as a current control transistor. Note that the number of transistors included in each pixel is not particularly limited and can be set appropriately as needed.

The circuit portion 303 includes a plurality of transistors, such as a transistor 309 and a transistor 310. The circuit portion 303 may be formed with a circuit including transistors having the same conductivity type (either n-channel transistors or p-channel transistors) or a CMOS circuit including an n-channel transistor and a p-channel transistor. Furthermore, a driver circuit may be provided outside.

There is no particular limitation on the structure of the transistors included in the light-emitting apparatus of this embodiment. For example, a planar transistor, a staggered transistor, or an inverted staggered transistor can be used. A top-gate transistor or a bottom-gate transistor can be used. Alternatively, gates may be provided above and below a semiconductor layer where a channel is formed.

There is no particular limitation on the crystallinity of a semiconductor material used in the transistor, and an amorphous semiconductor or a semiconductor having crystallinity (a microcrystalline semiconductor, a polycrystalline semiconductor, a single crystal semiconductor, or a semiconductor partly including crystal regions) can be used. It is preferable to use a semiconductor having crystallinity, in which case degradation of the transistor characteristics can be suppressed.

The semiconductor layer of the transistor preferably contains a metal oxide (also referred to as an oxide semiconductor). Alternatively, the semiconductor layer of the transistor may contain silicon. Examples of silicon include amorphous silicon and crystalline silicon (e.g., low-temperature polysilicon and single crystal silicon).

The semiconductor layer preferably contains indium, M (M is one or more kinds selected from gallium, aluminum, silicon, boron, yttrium, tin, copper, vanadium, beryllium, titanium, iron, nickel, germanium, zirconium, molybdenum, lanthanum, cerium, neodymium, hafnium, tantalum, tungsten, and magnesium), and zinc, for example. Specifically, M is preferably one or more kinds selected from aluminum, gallium, yttrium, and tin.

It is particularly preferable to use an oxide containing indium (In), gallium (Ga), and zinc (Zn) (also referred to as IGZO) for the semiconductor layer.

In the case where the semiconductor layer is an In-M-Zn oxide, as for the atomic ratio of metal elements in a sputtering target used for forming the In-M-Zn oxide, it is preferable that the atomic proportion of In is greater than or equal to that of M. Examples of the atomic ratio of metal elements in such a sputtering target are as follows: In:M:Zn=1:1:1; In:M:Zn=1:1:1.2; In:M:Zn=2:1:3; In:M:Zn=3:1:2; In:M:Zn=4:2:3; In:M:Zn=4:2:4.1; In:M:Zn=5:1:6; In:M:Zn=5:1:7; In:M:Zn=5:1:8; In:M:Zn=6:1:6; and In:M:Zn=5:2:5.

The transistors included in the circuit portions 303, 304a, and 304b and the transistors included in the pixel portion 302 may have the same structure or different structures. The plurality of transistors included in the circuit portions 303, 304a, and 304b may have the same structure or two or more kinds of structures. Similarly, a plurality of transistors included in the pixel portion 302 may have the same structure or two or more kinds of structures.

An end portion of the first electrode 313 is covered with an insulating layer 314. The insulating layer 314 can be formed using an organic compound such as a negative photosensitive resin or a positive photosensitive resin (acrylic resin), or an inorganic compound such as silicon oxide, silicon oxynitride, or silicon nitride. The insulating layer 314 preferably has a curved surface with curvature at an upper end portion or a lower end portion thereof. In that case, favorable coverage with a film formed over the insulating layer 314 can be obtained.

An EL layer 315 is provided over the first electrode 313, and a second electrode 316 is provided over the EL layer 315. The EL layer 315 includes a light-emitting layer, a hole-injection layer, a hole-transport layer, an electron-transport layer, an electron-injection layer, a charge-generation layer, and the like. The EL layer 315 preferably includes the organic compound of one embodiment of the present invention described in Embodiment 1. For example, the organic compound is preferably included as at least one of the material of the hole-injection layer, the material of the hole-transport layer, and the host material of the light-emitting layer.

The plurality of transistors and the plurality of organic EL devices 317 are sealed with the first substrate 301, the second substrate 306, and the sealant 305. A space 318 surrounded by the first substrate 301, the second substrate 306, and the sealant 305 may be filled with an inert gas (e.g., nitrogen or argon) or an organic substance (including the sealant 305).

An epoxy resin, glass frit, or the like can be used for the sealant 305. It is preferable to use a material that is permeable to as little moisture and oxygen as possible for the sealant 305. In the case where glass frit is used for the sealant, the first substrate 301 and the second substrate 306 are preferably glass substrates in terms of adhesion.

Figure 5C:
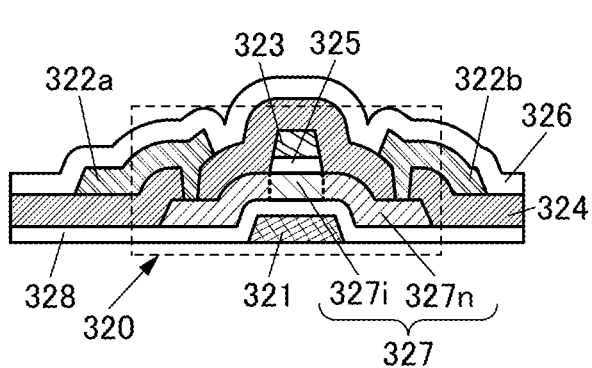
FIGS. 5C and 5D are cross-sectional views illustrating examples of transistors.
Figure 5D:
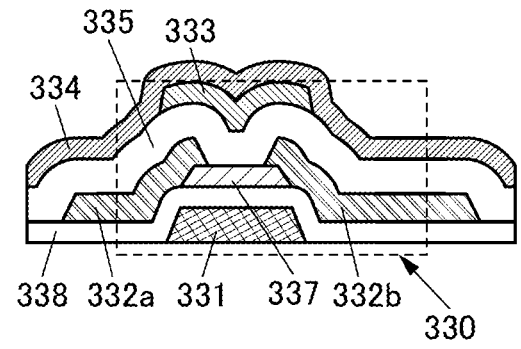

FIGS. 5C and 5D illustrate examples of transistors that can be used in a light-emitting apparatus.

A transistor 320 illustrated in FIG. 5C includes a conductive layer 321 functioning as a gate, an insulating layer 328 functioning as a gate insulating layer, a semiconductor layer 327 including a channel formation region 327i and a pair of low-resistance regions 327n, a conductive layer 322a connected to one of the pair of low-resistance regions 327n, a conductive layer 322b connected to the other of the pair of low-resistance regions 327n, an insulating layer 325 functioning as a gate insulating layer, a conductive layer 323 functioning as a gate, and an insulating layer 324 covering the conductive layer 323. The insulating layer 328 is positioned between the conductive layer 321 and the channel formation region 327i. The insulating layer 325 is positioned between the conductive layer 323 and the channel formation region 327i. The transistor 320 is preferably covered with an insulating layer 326. The insulating layer 326 may be included as a component in the transistor 320.

The conductive layer 322a and the conductive layer 322b are individually connected to the low-resistance region 327n through openings in the insulating layer 324. One of the conductive layers 322a and 322b functions as a source and the other functions as a drain.

The insulating layer 325 overlaps with at least the channel formation region 327i of the semiconductor layer 327. The insulating layer 325 may cover top surfaces and side surfaces of the pair of low-resistance regions 327n.

A transistor 330 illustrated in FIG. 5D includes a conductive layer 331 functioning as a gate, an insulating layer 338 functioning as a gate insulating layer, a conductive layer 332a and a conductive layer 332b which function as a source and a drain, a semiconductor layer 337, an insulating layer 335 functioning as a gate insulating layer, and a conductive layer 333 functioning as agate. The insulating layer 338 is positioned between the conductive layer 331 and the semiconductor layer 337. The insulating layer 335 is positioned between the conductive layer 333 and the semiconductor layer 337. The transistor 330 is preferably covered with an insulating layer 334. The insulating layer 334 may be included in the transistor 330 as a component.

The transistors 320 and 330 employ a structure in which the semiconductor layer where a channel is formed is positioned between two gates. The two gates may be connected to each other and supplied with the same signal to operate the transistor. Alternatively, the threshold voltage of the transistor may be controlled by supplying a potential for controlling the threshold voltage to one of the two gates and a potential for driving to the other.

A material through which impurities such as water and hydrogen do not easily diffuse is preferably used for at least one of the insulating layers that cover the transistors. This is because such an insulating layer can function as a barrier film. Such a structure can effectively suppress diffusion of the impurities into the transistors from the outside; thus, the reliability of the light-emitting apparatus can be increased.

As each of the insulating layers 325, 326, 328, 334, 335, and 338, an inorganic insulating film is preferably used. As the inorganic insulating film, a silicon nitride film, a silicon oxynitride film, a silicon oxide film, a silicon nitride oxide film, an aluminum oxide film, or an aluminum nitride film can be used, for example. A hafnium oxide film, an yttrium oxide film, a zirconium oxide film, a gallium oxide film, a tantalum oxide film, a magnesium oxide film, a lanthanum oxide film, a cerium oxide film, a neodymium oxide film, or the like may be used. A stack including two or more of the above insulating films may also be used.

As materials that can be used for the conductive layers included in the light-emitting apparatus, any of metals such as aluminum, titanium, chromium, nickel, copper, yttrium, zirconium, molybdenum, silver, tantalum, and tungsten, an alloy containing any of these metals as its main component, or the like can be used. A single layer structure or a stacked-layer structure including a film containing any of these materials can be used. For example, the following structures can be used: a single-layer structure of an aluminum film containing silicon, a two-layer structure in which an aluminum film is stacked over a titanium film, a two-layer structure in which an aluminum film is stacked over a tungsten film, a two-layer structure in which a copper film is stacked over a copper-magnesium-aluminum alloy film, a two-layer structure in which a copper film is stacked over a titanium film, a two-layer structure in which a copper film is stacked over a tungsten film, a three-layer structure in which a titanium film or a titanium nitride film, an aluminum film or a copper film, and a titanium film or a titanium nitride film are stacked in this order, and a three-layer structure in which a molybdenum film or a molybdenum nitride film, an aluminum film or a copper film, and a molybdenum film or a molybdenum nitride film are stacked in this order. Note that an oxide such as indium oxide, tin oxide, or zinc oxide may be used. Copper containing manganese is preferably used because controllability of the shape by etching is increased.

This embodiment can be combined with the other embodiment as appropriate.

Embodiment 4

In this embodiment, electronic devices of one embodiment of the present invention will be described with reference to drawings.

Examples of electronic devices include a television set, a monitor of a computer or the like, a digital camera, a digital video camera, a digital photo frame, a mobile phone (also referred to as a cellular phone or a mobile phone device), a portable game machine, a portable information terminal, an audio reproducing device, a large game machine such as a pinball machine, a biometric identification device, and a testing device.

The electronic devices of one embodiment of the present invention include the light-emitting device of one embodiment of the present invention in its display portion and thus has high light-emitting efficiency and high reliability.

The display portion of the electronic device in this embodiment can display a video with a resolution of, for example, full high definition, 4K2K, 8K4K, 16K8K, or higher. In addition, as a screen size of the display portion, the diagonal size can be greater than or equal to 20 inches, greater than or equal to 30 inches, greater than or equal to 50 inches, greater than or equal to 60 inches, or greater than or equal to 70 inches.

The electronic device of one embodiment of the present invention has flexibility and therefore can be incorporated along a curved surface of an inside or outside wall of a house or a building or a curved surface of an interior or an exterior of an automobile.

Furthermore, the electronic device of one embodiment of the present invention may include a secondary battery. It is preferable that the secondary battery be capable of being charged by contactless power transmission.

Examples of the secondary battery include a lithium ion secondary battery such as a lithium polymer battery using a gel electrolyte (lithium ion polymer battery), a nickel-hydride battery, a nickel-cadmium battery, an organic radical battery, a lead-acid battery, an air secondary battery, a nickel-zinc battery, and a silver-zinc battery.

The electronic device of one embodiment of the present invention may include an antenna. When a signal is received by the antenna, the electronic device can display a video, data, or the like on a display portion. When the electronic device includes the antenna and a secondary battery, the antenna may be used for contactless power transmission.

The electronic device in this embodiment may include a sensor (a sensor having a function of measuring force, displacement, position, speed, acceleration, angular velocity, rotational frequency, distance, light, liquid, magnetism, temperature, a chemical substance, sound, time, hardness, electric field, current, voltage, electric power, radiation, flow rate, humidity, gradient, oscillation, a smell, or infrared rays).

The electronic device in this embodiment can have a variety of functions. For example, the electronic device in this embodiment can have a function of displaying a variety of data (a still image, a moving image, a text image, and the like) on the display portion, a touch panel function, a function of displaying a calendar, date, time, and the like, a function of executing a variety of software (programs), a wireless communication function, and a function of reading out a program or data stored in a recording medium.

Figure 6A:
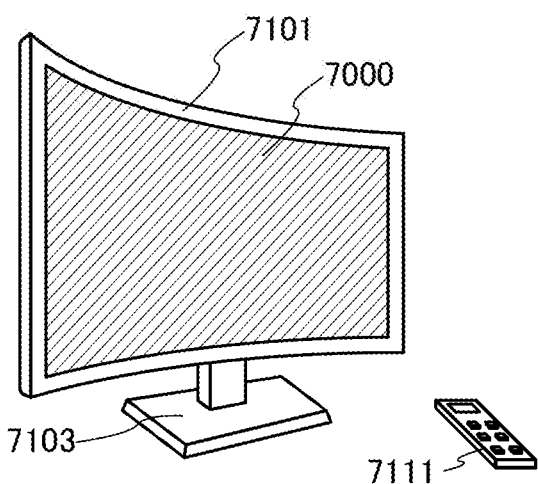
FIGS. 6A to 6D illustrate examples of electronic devices.

FIG. 6A illustrates an example of a television device. In a television device 7100, a display portion 7000 is incorporated in a housing 7101. Here, a structure in which the housing 7101 is supported by a stand 7103 is illustrated.

The light-emitting device of one embodiment of the present invention can be used for the display portion 7000.

Operation of the television device 7100 illustrated in FIG. 6A can be performed with an operation switch provided in the housing 7101 or a separate remote controller 7111. Alternatively, the display portion 7000 may include a touch sensor, and the television device 7100 can be operated by touching the display portion 7000 with a finger or the like. The remote controller 7111 may be provided with a display portion for displaying data output from the remote controller 7111. With operation keys or a touch panel provided in the remote controller 7111, channels and volume can be operated and videos displayed on the display portion 7000 can be operated.

Note that the television device 7100 has a structure in which a receiver, a modem, and the like are provided. A general television broadcast can be received with the receiver. When the television device is connected to a communication network with or without wires via the modem, one-way (from a transmitter to a receiver) or two-way (between a transmitter and a receiver or between receivers, for example) data communication can be performed.

Figure 6B:
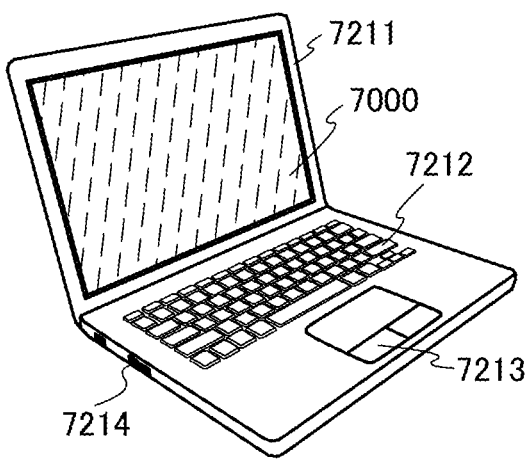

FIG. 6B illustrates an example of a laptop personal computer. A laptop personal computer 7200 includes a housing 7211, a keyboard 7212, a pointing device 7213, an external connection port 7214, and the like. In the housing 7211, the display portion 7000 is incorporated.

The light-emitting device of one embodiment of the present invention can be used for the display portion 7000.

Figure 6C:
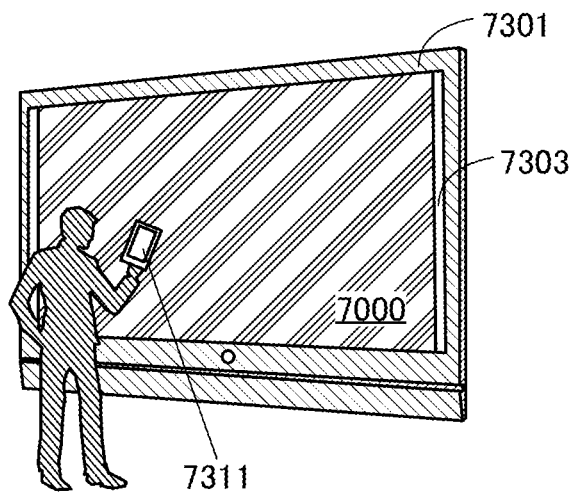
Figure 6D:
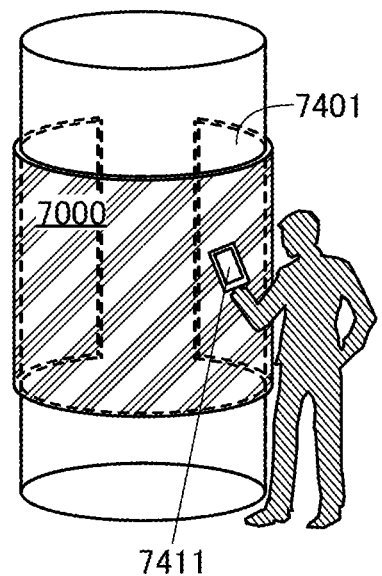

FIGS. 6C and 6D illustrate examples of digital signage.

Digital signage 7300 illustrated in FIG. 6C includes a housing 7301, the display portion 7000, a speaker 7303, and the like. Furthermore, the digital signage can include an LED lamp, operation keys (including a power switch or an operation switch), a connection terminal, a variety of sensors, a microphone, and the like.

FIG. 6D is digital signage 7400 attached to a cylindrical pillar 7401. The digital signage 7400 includes the display portion 7000 provided along a curved surface of the pillar 7401.

The light-emitting device of one embodiment of the present invention can be used for the display portion 7000 in FIGS. 6C and 6D.

A larger area of the display portion 7000 can increase the amount of data that can be provided at a time. The larger display portion 7000 attracts more attention, so that the effectiveness of the advertisement can be increased, for example.

The use of a touch panel in the display portion 7000 is preferable because in addition to display of a still image or a moving image on the display portion 7000, intuitive operation by a user is possible. Moreover, for an application for providing information such as route information or traffic information, usability can be enhanced by intuitive operation.

Furthermore, as illustrated in FIGS. 6C and 6D, it is preferable that the digital signage 7300 or the digital signage 7400 work with an information terminal 7311 or an information terminal 7411 such as a smartphone a user has through wireless communication. For example, information of an advertisement displayed on the display portion 7000 can be displayed on a screen of the information terminal 7311 or the information terminal 7411. By operation of the information terminal 7311 or the information terminal 7411, display on the display portion 7000 can be switched.

It is possible to make the digital signage 7300 or the digital signage 7400 execute a game with the use of the screen of the information terminal 7311 or the information terminal 7411 as an operation means (controller). Thus, an unspecified number of users can join in and enjoy the game concurrently.

FIGS. 7A to 7F illustrate examples of a portable information terminal including a flexible display portion 7001.

The display portion 7001 is manufactured using the light-emitting device of one embodiment of the present invention. For example, a light-emitting device that can be bent with a radius of curvature of greater than or equal to 0.01 mm and less than or equal to 150 mm can be used. The display portion 7001 may include a touch sensor so that the portable information terminal can be operated by touching the display portion 7001 with a finger or the like.

Figure 7A:
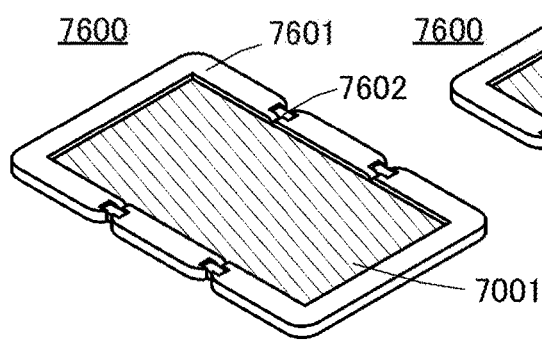
FIGS. 7A to 7F illustrate examples of electronic devices.
Figure 7B:
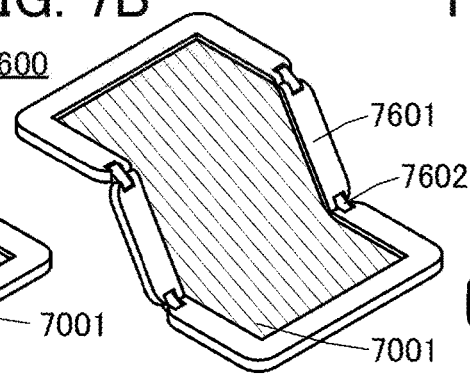
Figure 7C:
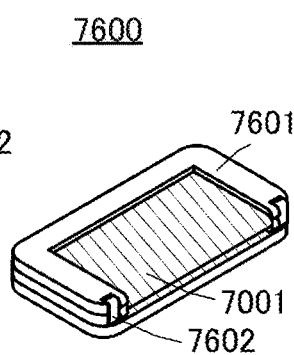

FIGS. 7A to 7C illustrate an example of a foldable portable information terminal. FIG. 7A illustrates an opened state, FIG. 7B illustrates a state in the middle of change from one of an opened state and a folded state to the other, and FIG. 7C illustrates a folded state of the portable information terminal 7600. The portable information terminal 7600 is highly portable when folded, and is highly browsable when opened because of a seamless large display area.

The display portion 7001 is supported by three housings 7601 joined together by hinges 7602. By folding a space between two housings 7601 with the hinges 7602, the portable information terminal 7600 can be reversibly changed in shape from an opened state to a folded state.

Figure 7D:
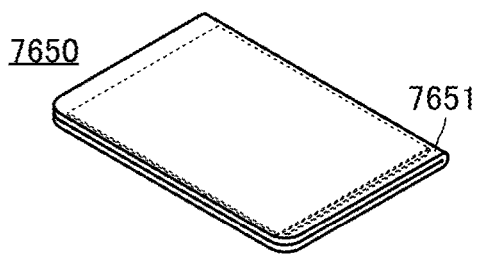
Figure 7E:
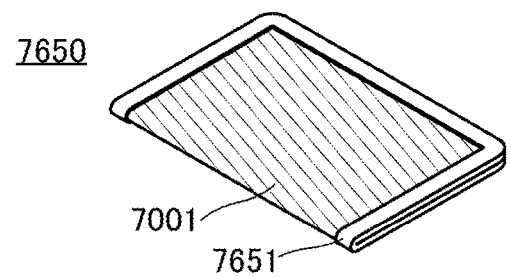

FIGS. 7D and 7E illustrate an example of a foldable portable information terminal. FIG. 7D illustrates a portable information terminal 7650 that is folded so that the display portion 7001 is on the inside; FIG. 7E illustrates the portable information terminal 7650 that is folded so that the display portion 7001 is on the outside. The portable information terminal 7650 includes the display portion 7001 and a non-display portion 7651. When the portable information terminal 7650 is not used, the portable information terminal 7650 is folded so that the display portion 7001 is on the inside, whereby contamination of or damage to the display portion 7001 can be suppressed.

Figure 7F:
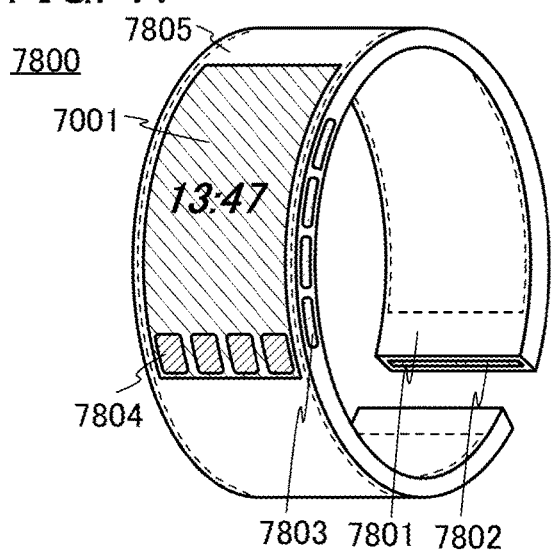

FIG. 7F illustrates an example of a wrist-watch-type portable information terminal. A portable information terminal 7800 includes a band 7801, the display portion 7001, an input-output terminal 7802, operation buttons 7803, and the like. The band 7801 has a function of a housing. A flexible battery 7805 can be mounted on the portable information terminal 7800. The battery 7805 may overlap with the display portion 7001 or the band 7801, for example.

The band 7801, the display portion 7001, and the battery 7805 have flexibility. Thus, the portable information terminal 7800 can be easily curved to have a desired shape.

The operation button 7803 can give a variety of functions such as time setting, on/off of the power, on/off of wireless communication, setting and cancellation of silent mode, and setting and cancellation of power saving mode. For example, the functions of the operation button 7803 can be set freely by the operating system incorporated in the portable information terminal 7800.

By touching an icon 7804 displayed on the display portion 7001 with a finger or the like, application can be started.

The portable information terminal 7800 can execute near field communication conformable to a communication standard. For example, mutual communication with a headset capable of wireless communication enables hands-free calling.

The portable information terminal 7800 may include the input-output terminal 7802. In the case where the input-output terminal 7802 is included, data can be directly transmitted to and received from another information terminal via a connector. Charging through the input-output terminal 7802 is also possible. Note that charging of the portable information terminal described as an example in this embodiment can be performed by non-contact power transmission without using the input-output terminal.

Figure 8A:
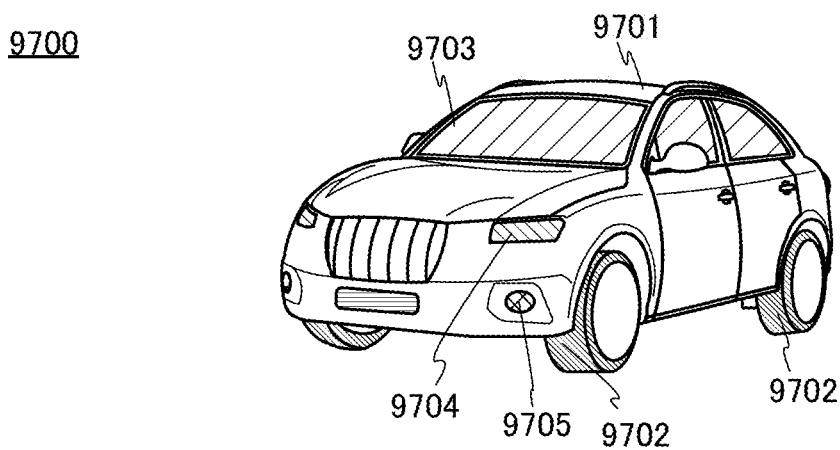
FIGS. 8A to 8C illustrate examples of electronic devices.
Figure 8B:
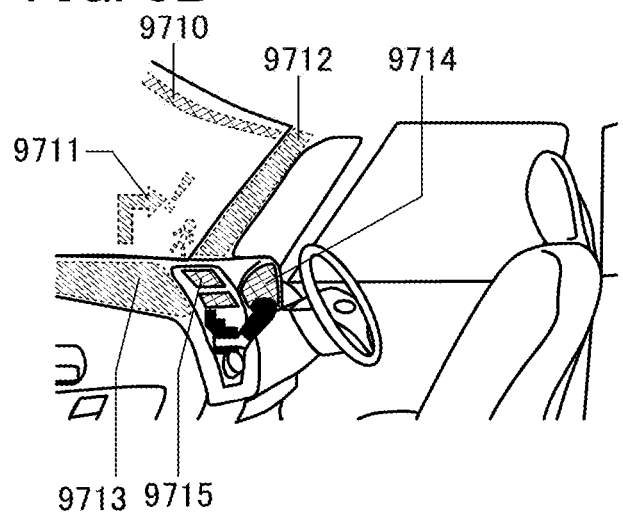

FIG. 8A is an external view of an automobile 9700. FIG. 8B illustrates a driver's seat of the automobile 9700. The automobile 9700 includes a car body 9701, wheels 9702, a windshield 9703, lights 9704, fog lamps 9705, and the like. The light-emitting device of one embodiment of the present invention can be used in a display portion of the automobile 9700, for example. For example, the light-emitting device or the like of one embodiment of the present invention can be provided for a display portion 9710 to a display portion 9715 illustrated in FIG. 8B. Alternatively, the light-emitting device or the like of one embodiment of the present invention may be used in the lights 9704 or the fog lamps 9705.

The display portion 9710 and the display portion 9711 are display devices provided in an automobile windshield. The light-emitting device of one embodiment of the present invention can be a see-through device, through which the opposite side can be seen, by using a light-transmitting conductive material for forming its electrodes and wirings. Such a display portion 9710 or 9711 in a see-through state does not hinder driver's vision during driving of the automobile 9700. Therefore, the light-emitting device of one embodiment of the present invention can be provided in the windshield of the automobile 9700. In the case where a transistor for driving the light-emitting device is provided, a transistor having a light-transmitting property, such as an organic transistor using an organic semiconductor material or a transistor using an oxide semiconductor, is preferably used.

The display portion 9712 is a display device provided on a pillar portion. For example, the display portion 9712 can compensate for the view hindered by the pillar portion by showing an image taken by an imaging unit provided in the car body. The display portion 9713 is a display device provided on the dashboard. For example, the display portion 9713 can compensate for the view hindered by the dashboard by showing an image taken by an imaging unit provided in the car body. That is, by displaying an image taken by an imaging unit provided on the outside of the automobile, blind areas can be eliminated and safety can be increased. Displaying an image to compensate for the area which a driver cannot see, makes it possible for the driver to confirm safety easily and comfortably.

Figure 8C:
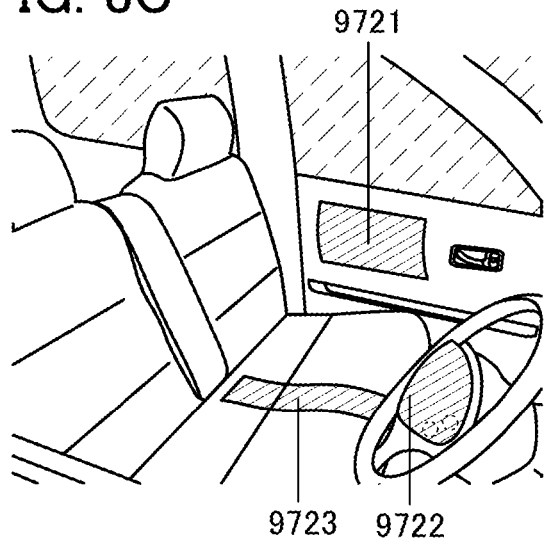

FIG. 8C illustrates the inside of a car in which a bench seat is used as a driver seat and a front passenger seat. A display portion 9721 is a display device provided in a door portion. For example, the display portion 9721 can compensate for the view hindered by the door by showing an image taken by an imaging unit provided in the car body. A display portion 9722 is a display device provided in a steering wheel. A display portion 9723 is a display device provided in the middle of a seating face of the bench seat. Provided on the seating surface, backrest, or the like, the display device can be used as a seat heater with heat generation of the display device as a heat source.

The display portion 9714, the display portion 9715, and the display portion 9722 can provide a variety of kinds of information by displaying navigation data, a speedometer, a tachometer, a mileage, a fuel meter, a gearshift indicator, air-condition setting, and the like. The content, layout, or the like of the display on the display portions can be changed freely by a user as appropriate. The above information can also be displayed on the display portion 9710 to the display portion 9713, the display portion 9721, and the display portion 9723. The display portion 9710 to the display portion 9715 and the display portion 9721 to the display portion 9723 can also be used as lighting devices. The display portion 9710 to the display portion 9715 and the display portion 9721 to the display portion 9723 can also be used as heating devices.

An electronic device of one embodiment of the present invention has high emission efficiency and high reliability because the electronic device includes the light-emitting apparatus of one embodiment of the present invention as a light source. For example, the light-emitting apparatus of one embodiment of the present invention can be used for a light source that emits visible light or near-infrared light. The light-emitting apparatus of one embodiment of the present invention can also be used as a light source of a lighting device.

Figure 9A:
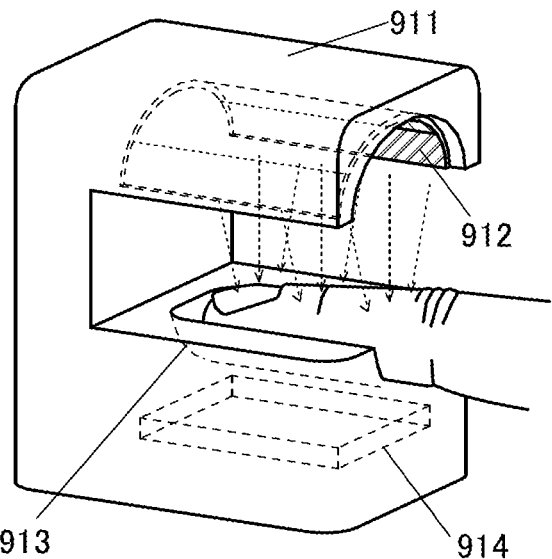
FIGS. 9A to 9E illustrate examples of electronic devices.

FIG. 9A illustrates a biometric identification device which senses a finger vein and includes a housing 911, a light source 912, a sensing stage 913, and the like. By putting a finger on the sensing stage 913, an image of a form of the finger vein can be taken. The light source 912 which emits near-infrared light is provided over the sensing stage 913, and an imaging device 914 is provided under the sensing stage 913. The sensing stage 913 includes a material that transmits near-infrared light. An image of near-infrared light emitted from the light source 912 and passes through the finger can be taken by the imaging device 914. Note that an optical system may be provided between the sensing stage 913 and the imaging device 914. The device structure described above can be applied to a biometric identification device that senses a palm vein.

The light-emitting apparatus of one embodiment of the present invention can be used for the light source 912. The light-emitting apparatus of one embodiment of the present invention can be set with a curved shape, and can emit light uniformly with respect to a target. In particular, the light-emitting apparatus preferably emits near-infrared light with the maximum peak intensity at a wavelength from 700 nm to 1200 nm. Light passing through a finger or a palm is received and its image is taken, whereby the position of the vein can be detected. This action can be utilized for biometric identification. Furthermore, when combined with a global shutter system, the light-emitting apparatus enables highly accurate sensing even while the target is moving.

Figure 9B:
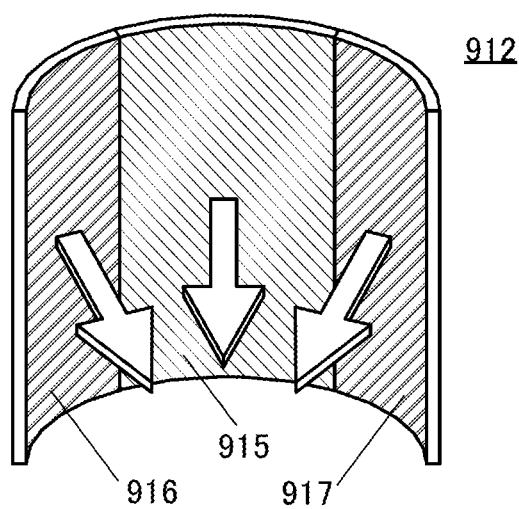

The light source 912 can include a plurality of light-emitting portions, such as light-emitting portions 915, 916, and 917 illustrated in FIG. 9B. Light emitted from the light-emitting portions 915, 916, and 917 may have different wavelengths. Furthermore, the timings when the light-emitting portions emit light can be made different. By changing wavelengths and angles of light, different images can be taken successively and a plurality of images can be used for the identification, which achieves high security.

Figure 9C:
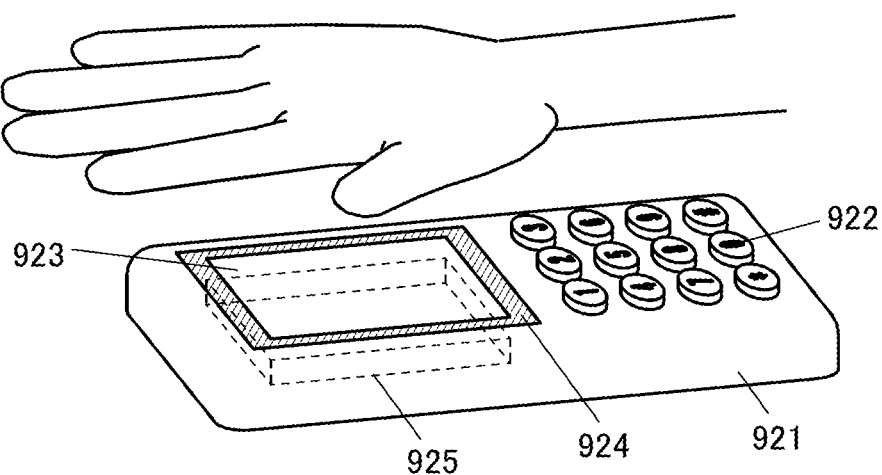

FIG. 9C illustrates a biometric identification device which senses a palm vein and includes a housing 921, operation buttons 922, a sensing portion 923, a light source 924 that emits near-infrared light, and the like. By holding a hand over the sensing portion 923, a form of the palm vein can be recognized. Furthermore, a security code or the like can be input with the operation buttons. The light source 924 is provided to surround the sensing portion 923 and irradiates a target (hand) with light. Then, light reflected by the target enters the sensing portion 923. The light-emitting apparatus of one embodiment of the present invention can be used for the light source 924. An imaging device 925 is provided directly under the sensing portion 923, and can take an image of the target (a whole image of the hand). Note that an optical system may be provided between the sensing portion 923 and the imaging device 925. The device structure described above can be applied to a biometric identification device that senses a finger vein.

Figure 9D:
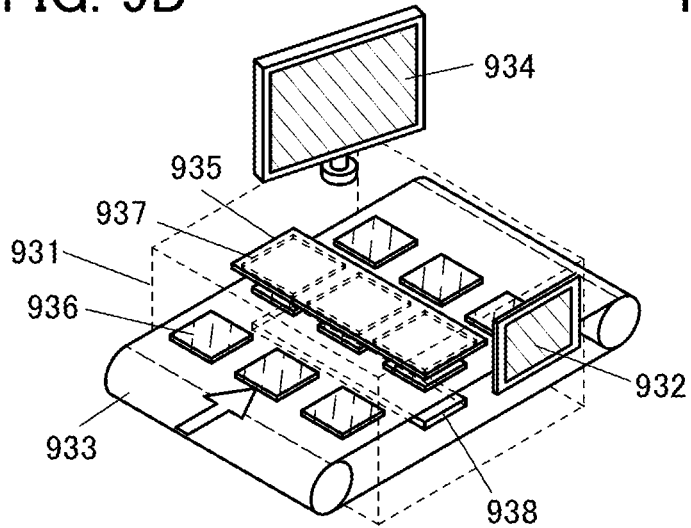

FIG. 9D illustrates a non-destructive testing device which includes a housing 931, an operation panel 932, a transport mechanism 933, a monitor 934, a sensing unit 935, a light source 938 emitting near-infrared light, and the like. The light-emitting apparatus of one embodiment of the present invention can be used for the light source 938. Inspection members 936 are transported to the position directly under the sensing unit 935 by the transport mechanism 933. The inspection member 936 is irradiated with near-infrared light from the light source 938, and an image of the light passing therethrough is taken by an imaging device 937 provided in the sensing unit 935. The taken image is displayed on the monitor 934. After that, the inspection members 936 are transported to an exit of the housing 931 and a defective member is separately collected. Imaging with use of near-infrared light enables non-destructive and high-speed sensing of defective elements inside the inspection member, such as defects and foreign substances.

Figure 9E:
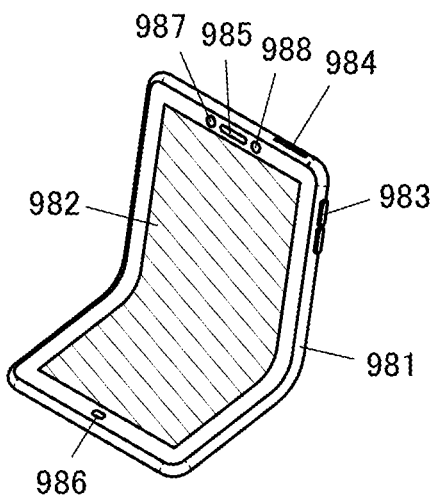

FIG. 9E illustrates a mobile phone device which includes a housing 981, a display portion 982, operation buttons 983, an external connection port 984, a speaker 985, a microphone 986, a first camera 987, a second camera 988, and the like. The display portion 982 of the mobile phone device includes a touch sensor. The housing 981 and the display portion 982 have flexibility. All operations including making a call and inputting text can be performed by touch on the display portion 982 with a finger, a stylus, or the like. The first camera 987 can take an image of visible light, and the second camera 988 can take an image of infrared light (an image of near-infrared light). The mobile phone device or the display portion 982 illustrated in FIG. 9E may include the light-emitting apparatus of one embodiment of the present invention.

This embodiment can be combined with the other embodiment as appropriate.

Example 1

Synthesis Example 1

In this example, a method of synthesizing an organic compound of one embodiment of the present invention will be described. In this example, a method of synthesizing N-[4"-(9H-carbazol-9-yl)-1,1':4',1"-terphenyl-4-yl]-N-(1,1'-biphenyl-2-yl)-9,9-dimethyl-9H-fluoren-2-amine (abbreviation: oYGTBiF(2)), which is represented by Structural Formula (100) in Embodiment 1, will be described.

[Chemical Formula 38]

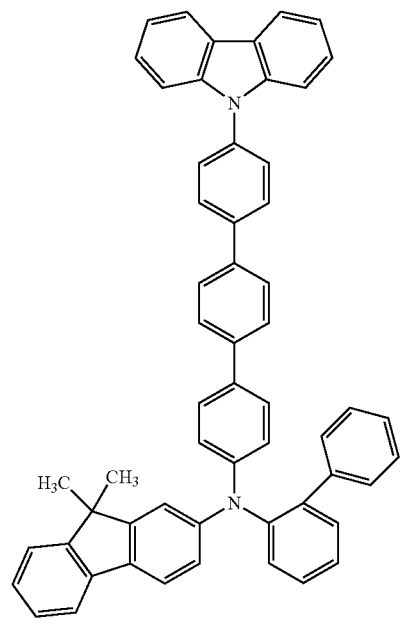

oYGTBiF(2)

First, 1.3 g (3.7 mmol) of N-[1,1'-biphenyl]-2-yl-9,9-dimethyl-9H-fluoren-2-amine, 1.6 g (3.7 mmol) of 9-(4"-chloro[1,1':4',1"-terphenyl]-4-yl)-9H-carbazole, and 26 mg (74 µmol) of di-tert-butyl(1-methyl-2,2-diphenylcyclopropyl)phosphine (registered trademark: cBRIDP) were put into a 200 mL three-neck flask equipped with a reflux pipe; then, the air in the system was replaced with nitrogen. To the system, 0.71 g (7.4 mmol) of sodium tert-butoxide and 30 mL of xylene were added. Then, degassing under reduced pressure and replacement of the air in the system with nitrogen were performed three times. To the system, 21 mg (37 µmol) of bis(dibenzylideneacetone)palladium(0) was added, and the mixture was stirred at 150° C. for 10 hours. After the stirring, an insoluble matter was removed from the mixture by suction filtration. Water was added to the obtained filtrate so that an aqueous layer was subjected to extraction with toluene. The obtained organic layer was washed twice with water and then washed with saturated saline. The organic layer was dried with magnesium sulfate. The obtained mixture was gravity-filtered to remove the magnesium sulfate. The obtained filtrate was concentrated to give 2.6 g of a yellow viscous solid. The obtained solid was purified by silica gel chromatography (with a developing solvent containing toluene and hexane in a 1:2 ratio), and the obtained pale yellow solid was recrystallized with toluene, whereby 0.83 g of a pale yellow solid was obtained in a yield of 30%.

By a train sublimation method, 0.83 g of the obtained solid was purified. In the sublimation purification, the solid was heated at 320° C. for 16 hours under a pressure of 3.8 Pa with an argon flow rate of 15 mL/min. After the sublimation purification, 0.55 g of a target pale yellow solid was obtained at a collection rate of 66%. In the sublimation purification, the material was sublimed by heating at 320° C. and the collection rate was as high as 66%, which means that the organic compound of one embodiment of the present invention had high sublimability and there was no problem on the evaporation process. Synthesis Scheme (A-1) is shown below.

[Chemical Formula 39]

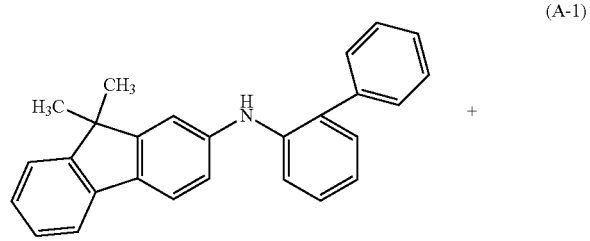

(A-1)

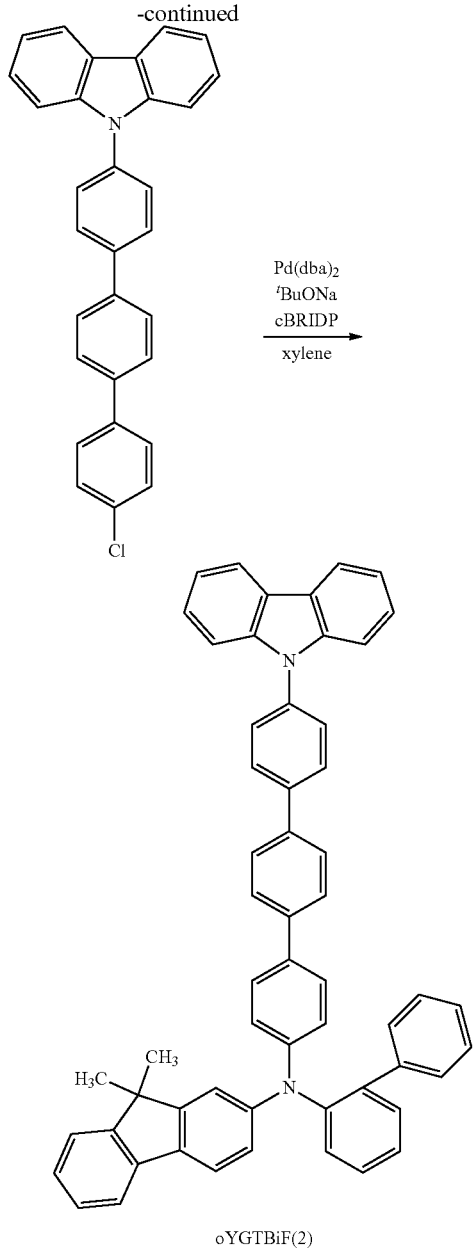

oYGTBiF(2)

Analysis results by nuclear magnetic resonance (H NMR) spectroscopy of the obtained pale yellow solid are shown below. The results show that oYGTBiF(2) represented by Structural Formula (100) was obtained in this example.

$^1$H NMR (dichloromethane-$d_2$, 300 MHz): δ=8.17 (d, J=7.8 Hz, 2H), 7.91 (d, J=8.7 Hz, 2H), 7.78 (d, J=8.7 Hz, 2H), 7.71 (d, J=8.7 Hz, 2H), 7.67 (d, J=8.7 Hz, 2H), 7.57 (d, J=7.2 Hz, 1H), 7.52-7.19 (m, 18H), 7.14-7.06 (m, 5H), 6.92 (d, J=1.8 Hz, 1H), 6.79 (dd, J1=6.0 Hz, J2=2.1 Hz, 1H), 1.30 (s, 6H).

Next, ultraviolet-visible absorption spectra (hereinafter simply referred to as "absorption spectra") and emission spectra of oYGTBiF(2) in a toluene solution and a solid thin film of oYGTBiF(2) were measured. The solid thin film was formed over a quartz substrate by a vacuum evaporation method.

The absorption spectra were measured using UV-visible spectrophotometers (solution: V-550 manufactured by JASCO Corporation, thin film: U-4100 manufactured by Hitachi High-Technologies Corporation). To calculate the absorption spectrum of oYGTBiF(2) in a toluene solution, the absorption spectrum of toluene put in a quartz cell was measured and then subtracted from the absorption spectrum of the toluene solution of oYGTBiF(2) put in a quartz cell. The absorption spectrum of the thin film was calculated using an absorbance ($-\log_{10}$ [% T/(100–% R)]) obtained from the transmittance and reflectance of the thin film including the substrate. Note that % T represents transmittance and % R represents reflectance. The emission spectra were measured with a fluorescence spectrophotometer (FS920 produced by Hamamatsu Photonics K.K.). Note that absorption spectra and the emission spectra were measured at room temperature.

Figure 10A:
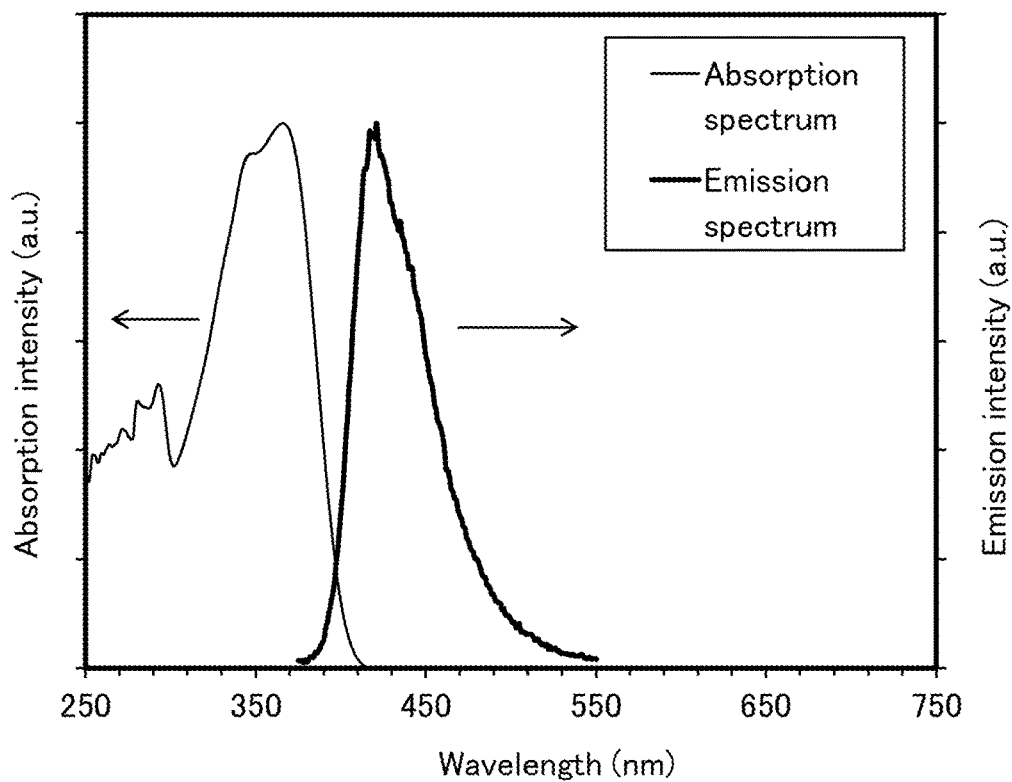
FIGS. 10A and 10B each show an ultraviolet-visible absorption spectrum and an emission spectrum of an organic compound represented by Structural Formula (100).

FIG. 10A shows the obtained absorption and emission spectra of the toluene solution. The horizontal axis represents wavelength, and the vertical axes represent absorption intensity and emission intensity.

As seen in FIG. 10A, an absorption peak of oYGTBiF(2) in the toluene solution was observed at around 366 nm, and an emission peak thereof was observed at around 421 nm (excitation wavelength: 366 nm).

Figure 10B:
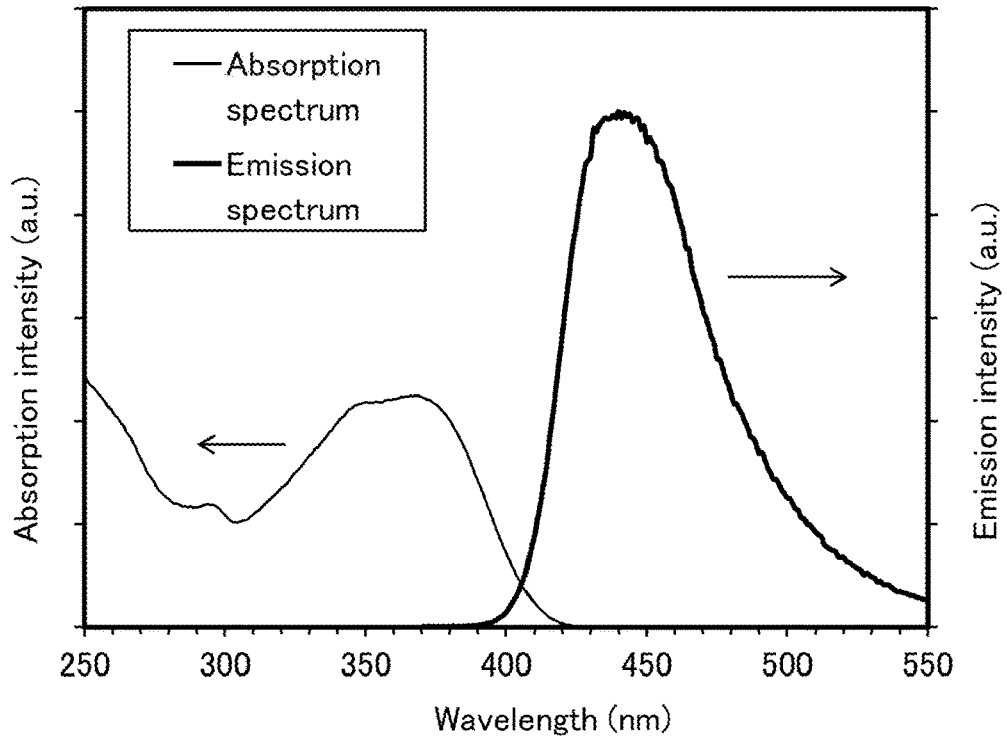

FIG. 10B shows the obtained absorption and emission spectra of the obtained solid thin film. The horizontal axis represents wavelength and the vertical axes represent absorption intensity and emission intensity.

As seen in FIG. 10B, absorption peaks of oYGTBiF(2) in a solid thin film were observed at around 294 nm, 350 nm, and 367 nm, and an emission peak thereof was observed at around 440 nm (excitation wavelength: 365 nm).

It was found that the organic compound of one embodiment of the present invention, oYGTBiF(2), is a host material suitable for a fluorescent material that emits blue light or energy with a longer wavelength than blue light and for a phosphorescent material that emits green light or energy with a longer wavelength than green light. Furthermore, oYGTBiF(2) can be used as a host material that is used with a light-emitting substance in the visible region or the near infrared region (e.g., a fluorescent material, a delayed fluorescent material, or a phosphorescent material) or as a light-emitting substance.

Next, the HOMO level and the LUMO level of oYGTBiF(2) were obtained through a cyclic voltammetry (CV) measurement. The calculation method is shown below.

An electrochemical analyzer (ALS model 600A or 600C, produced by BAS Inc.) was used as the measurement apparatus. A solution for the CV measurement was prepared in the following manner: tetra-n-butylammonium perchlorate (n-Bu$_4$NClO$_4$, produced by Tokyo Chemical Industry Co., Ltd., catalog No. T0836) as a supporting electrolyte was dissolved in dehydrated dimethylformamide (DMF, produced by Sigma-Aldrich Co. LLC., 99.8%, catalog No. 22705-6) as a solvent at a concentration of 100 mmol/L, and the object to be measured was dissolved therein at a concentration of 2 mmol/L.

A platinum electrode (PTE platinum electrode, produced by BAS Inc.) was used as a working electrode, another platinum electrode (Pt counter electrode for VC-3 (5 cm), produced by BAS Inc.) was used as an auxiliary electrode, and an Ag/Ag$^+$ electrode (RE7 reference electrode for non-aqueous solvent, produced by BAS Inc.) was used as a reference electrode. Note that the measurement was performed at a room temperature (20° C. to 25° C.).

In addition, the scan speed at the CV measurement was set to 0.1 V/sec, and an oxidation potential Ea [V] and a reduction potential Ec [V] with respect to the reference electrode were measured. The potential Ea is an intermediate potential of an oxidation-reduction wave, and the potential Ec is an intermediate potential of a reduction-oxidation wave. Here, the potential energy of the reference electrode used in this example with respect to the vacuum level is found to be –4.94 [eV], and thus, the HOMO level and the LUMO level can be obtained from the following formula: HOMO level [eV]=–4.94–Ea and LUMO level [eV]–4.94–Ec.

Furthermore, CV measurement was repeated 100 times, and the oxidation-reduction wave in the hundredth cycle was compared with the oxidation-reduction wave in the first cycle to examine the electrical stability of the compound.

As a result, in the measurement of an oxidation potential Ea [V] of oYGTBiF(2), the HOMO level was –5.42 eV. In contrast, the LUMO level was –2.31 eV in the measurement of the reduction potential Ec [V]. Accordingly, it was found that oYGTBiF(2) has a high electron-blocking property. When the oxidation-reduction wave was repeatedly measured, in the Ea measurement, the peak intensity of the oxidation-reduction wave after the hundredth cycle was maintained to be 88% of that of the oxidation-reduction wave in the first cycle, and in the Ec measurement, the peak intensity of the oxidation-reduction wave after the hundredth cycle was maintained to be 99% of that of the oxidation-reduction wave in the first cycle; thus, resistance to oxidation and reduction of oYGTBiF(2) was found to be extremely high.

Differential scanning calorimetry (DSC measurement) was performed on oYGTBiF(2) by Pyris1DSC produced by PerkinElmer, Inc. In the differential scanning calorimetry, after the temperature was raised from –10° C. to 320° C. at a temperature rising rate of 40° C./min, the temperature was held for a minute and then decreased to –10° C. at a temperature decreasing rate of 100° C./min. This operation was repeated twice successively. It was found from the DSC measurement result of the second cycle that the glass transition point of oYGTBiF(2) is 137° C., that is, oYGTBiF(2) is a substance with extremely high heat resistance.

The thermogravimetry-differential thermal analysis was performed on oYGTBiF(2). The measurement was performed using a high vacuum differential type differential thermal balance (TG-DTA2410SA, produced by Bruker AXS K.K.). The measurement was performed under atmospheric pressure at a temperature rising rate of 10° C./min under a nitrogen stream (flow rate: 200 mL/min). In the thermogravimetry-differential thermal analysis, the temperature (decomposition temperature) at which the weight obtained by thermogravimetry was reduced by 5% of the weight at the beginning of the measurement was found to be 484° C., which shows that oYGTBiF(2) is a substance with high heat resistance.

From the above results, it was found that the organic compound of one embodiment of the present invention has both high heat resistance and high sublimability, and can provide an organic optical device (a light-emitting device and a light-receiving device) with high heat resistance and increase the productivity of device manufacturing.

Example 2

In this example, a light-emitting device of one embodiment of the present invention is fabricated and evaluated, and the evaluation results will be described.

In this example, Device 1 using oYGTBiF(2) (Structural Formula (100)) described in Example 1, Comparative Device 2, Comparative Device 3, and Comparative Device 4 were fabricated as light-emitting devices and evaluated. The results will be described.

Figure 11:
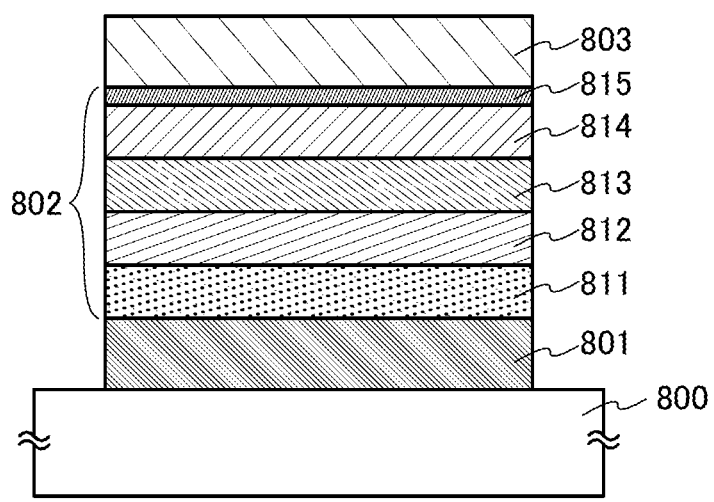
FIG. 11 is a cross-sectional view illustrating a light-emitting device in Example.

FIG. 11 illustrates structures of the four light-emitting devices used in this example, and Table 1 shows specific structures. The chemical formulae of materials used in this example are shown below.

TABLE 1

|  | First electrode 801 | Hole-injection layer 811 | Hole-transport layer 812 | Light-emitting layer 813 | Electron-transport layer 814 | Electron-injection layer 815 | Second electrode 803 |
| --- | --- | --- | --- | --- | --- | --- | --- |
| Device 1 | ITSO (70 nm) | oYGTBiF(2):ALD-MP001Q (1:0.1, 10 nm) | oYGTBiF(2) (20 nm) | DBfBB1TP (10 nm) | cgDBCzPA: 3,10PCA2Nbf(IV)-02 (1:0.015, 25 nm) | cgDBCzPA (15 nm) | NBPhen (10 nm) | LiF (1 nm) | Al (200 nm) |
| Comparative Device 2 |  | oYGBBiF:ALD-MP001Q (1:0.1, 10 nm) | oYGBBiF (20 nm) |  |  |  |  |  |
| Comparative Device 3 |  | oYGTBilBP:ALD-MP001Q (1:0.1, 10 nm) | oYGTBilBP (20 nm) |  |  |  |  |  |
| Comparative Device 4 |  | YGTBiF(2):ALD-MP001Q (1:0.1, 10 nm) | YGTBiF(2) (20 nm) |  |  |  |  |  |

[Chemical Formula 40]

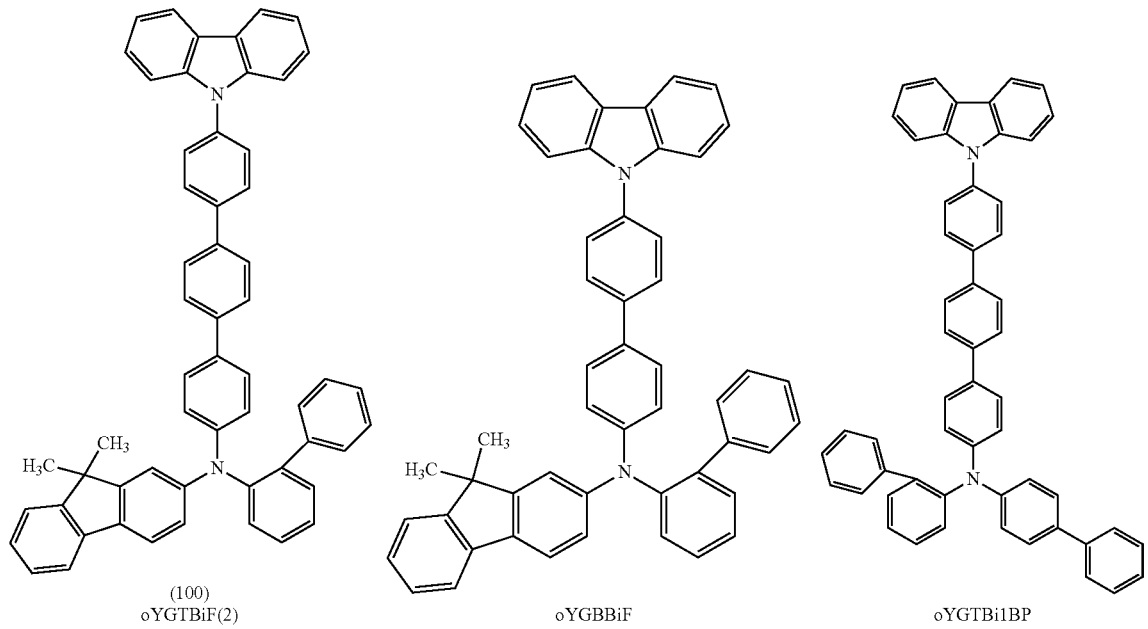

(100)
oYGTBiF(2)　　　oYGBBiF　　　oYGTBi1BP

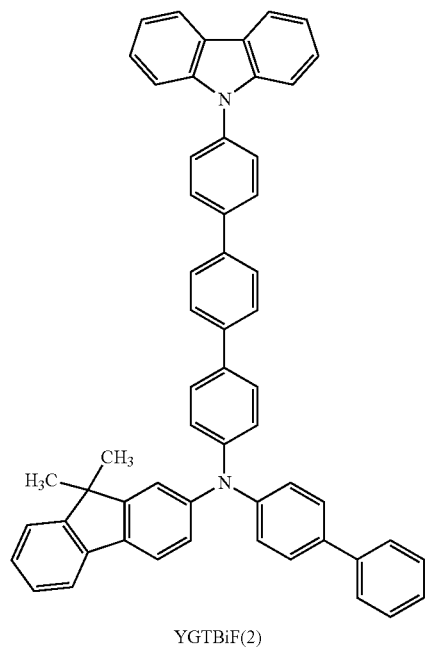
YGTBiF(2)
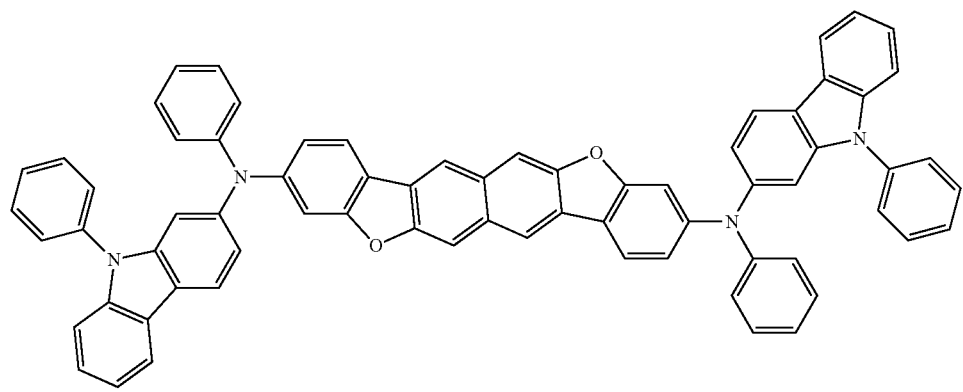
3,10PCA2Nbf(IV)-02
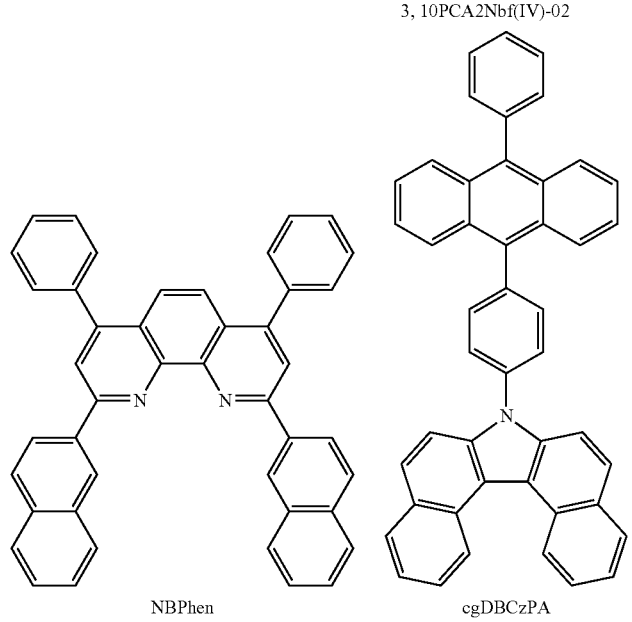
NBPhen  cgDBCzPA

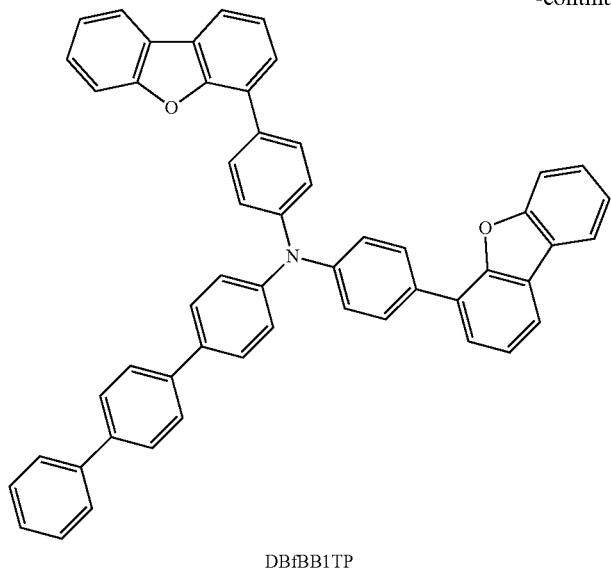

DBfBB1TP

<<<Fabrication of Light-Emitting Devices>>>

In each of the light-emitting devices described in this example, as illustrated in FIG. 11, a first electrode 801 is formed over a substrate 800; a hole-injection layer 811, a hole-transport layer 812, a light-emitting layer 813, an electron-transport layer 814, and an electron-injection layer 815, which constitute an EL layer 802, are stacked in this order over the first electrode 801; and a second electrode 803 is stacked over the electron-injection layer 815.

First, the first electrode 801 was formed over the substrate 800. The electrode area was set to 4 mm² (2 mm×2 mm). A glass substrate was used as the substrate 800. The first electrode 801 was formed to a thickness of 70 nm using indium tin oxide containing silicon oxide (ITSO) by a sputtering method. Note that in this example, the first electrode 801 functions as an anode.

For pretreatment, a surface of the substrate was washed with water, baking was performed at 200° C. for 1 hour, and then UV ozone treatment was performed for 370 seconds. After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the hole-injection layer 811 was formed over the first electrode 801. The hole-injection layer 811 was formed in such a manner that the pressure in the vacuum evaporation apparatus was reduced to $10^{-4}$ Pa, and then a material X and ALD-MP001Q (produced by Analysis Atelier Corporation, material serial No. 1S20180314) were co-evaporated to a thickness of 10 nm in a weight ratio of the material X: ALD-MP001Q=1:0.1. Note that ALD-MP001Q is an acceptor material.

Next, the hole-transport layer 812 was formed over the hole-injection layer 811. The hole-transport layer 812 was formed in such a manner that the material X was deposited by evaporation to a thickness of 20 nm, and N,N-bis[4-(dibenzofuran-4-yl)phenyl]-4-amino-p-terphenyl (abbreviation: DBfBB1TP) was deposited by evaporation to a thickness of 10 nm.

As the material X in the hole-injection layer 811 and the hole-transport layer 812, N-[4″-(9H-carbazol-9-yl)-1,1′:4′,1″-terphenyl-4-yl]-N-(1,1′-biphenyl-2-yl)-9,9-dimethyl-9H-fluoren-2-amine (abbreviation: oYGTBiF(2)) was used for Device 1, N-[4′-(9H-carbazol-9-yl)-1,1′-biphenyl-4-yl]-N-(1,1′-biphenyl-2-yl)-9,9′-dimethyl-9H-fluoren-2-amine (abbreviation: oYGBBiF) was used for Comparative Device 2, 2,4′-diphenyl-4″-[4′-(9H-carbazol-9-yl)-1,1′-biphenyl-4-yl]triphenylamine (abbreviation: oYGTBi1BP) was used for Comparative Device 3, and N-[4″-(9H-carbazol-9-yl)-1,1′:4′,1″-terphenyl-4-yl]-N-(1,1′-biphenyl-4-yl)-9,9-dimethyl-9H-fluoren-2-amine (abbreviation: YGTBiF(2)) was used for Comparative Device 4.

Next, the light-emitting layer 813 was formed over the hole-transport layer 812 as follows: 7-[4-(10-phenyl-9-anthryl)phenyl]-7H-dibenzo[c,g]carbazole (abbreviation: cgDBCzPA), which was used as a host material, and 3,10-bis[N-(9-phenyl-9H-carbazol-2-yl)-N-phenylamino]naphtho[2,3-b;6,7-b′]bisbenzofuran (abbreviation: 3,10PCA2Nbf(IV)-02), which was used as a guest material (fluorescent material), were co-evaporated in a weight ratio of cgDBCzPA:3,10PCA2Nbf(IV)-02=1:0.015. The thickness was set to 25 nm.

Next, the electron-transport layer 814 was formed over the light-emitting layer 813. The electron-transport layer 814 was formed in the following manner: cgDBCzPA was deposited by evaporation to a thickness of 15 nm and 2,9-bis(naphthalen-2-yl)-4,7-diphenyl-1,10-phenanthroline (abbreviation: NBPhen) was deposited by evaporation to a thickness of 10 nm.

Then, the electron-injection layer 815 was formed over the electron-transport layer 814. As the electron-injection layer 815, lithium fluoride (LiF) was deposited by evaporation to a thickness of 1 nm.

After that, the second electrode 803 was formed over the electron-injection layer 815. As the second electrode 803, aluminum was deposited by evaporation to a thickness of 200 nm. In this example, the second electrode 803 functions as a cathode.

Through the above steps, the light-emitting device including the EL layer 802 between the pair of electrodes was formed over the substrate 800. Note that the hole-injection layer 811, the hole-transport layer 812, the light-emitting layer 813, the electron-transport layer 814, and the electron-injection layer 815 described above are functional layers forming the EL layer in the light-emitting device of one embodiment of the present invention. Furthermore, in all the evaporation steps in the above fabrication method, evaporation was performed by a resistance-heating method.

The light-emitting device fabricated as described above was sealed using another substrate (not illustrated) in the following manner. The substrate (not illustrated) to which a sealant to be cured by ultraviolet light was applied was fixed to the substrate 800 in a glove box containing a nitrogen atmosphere, and the substrates were bonded to each other such that the sealant was attached so as to surround the light-emitting device formed over the substrate 800. In the sealing process, the sealant was irradiated with 365-nm ultraviolet light at 6 J/cm$^2$ to be cured, and the sealant was subjected to heat treatment at 80° C. for 1 hour to be stabilized.

<<<Operation Characteristics of Light-Emitting Devices>>>

Operation characteristics of the light-emitting devices fabricated in this example were measured. Note that the measurement was performed at room temperature.

Figure 12:
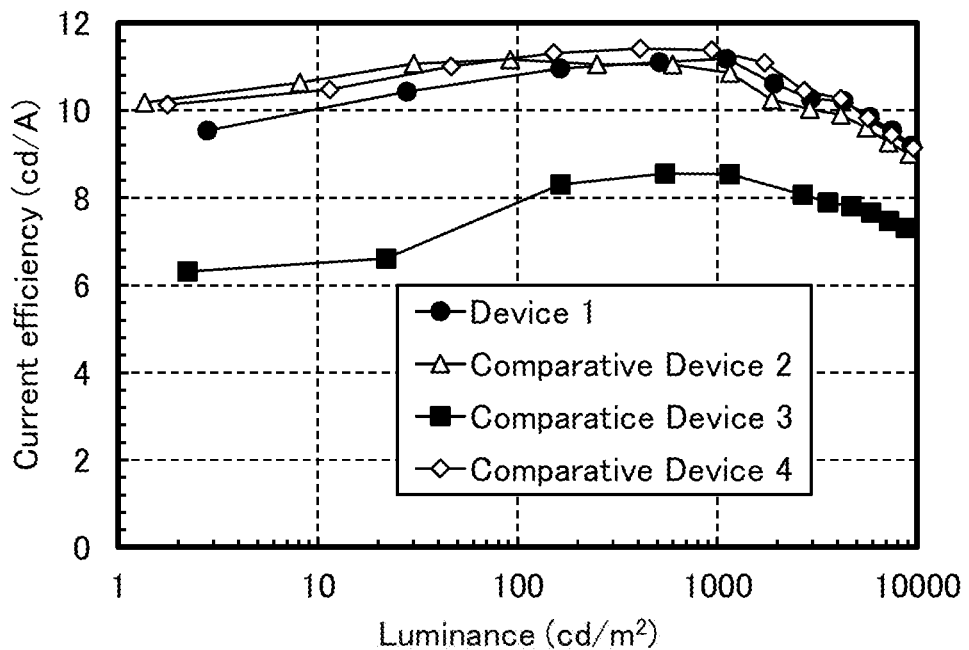
FIG. 12 shows luminance-current efficiency characteristics of light-emitting devices in Example 2.
Figure 13:
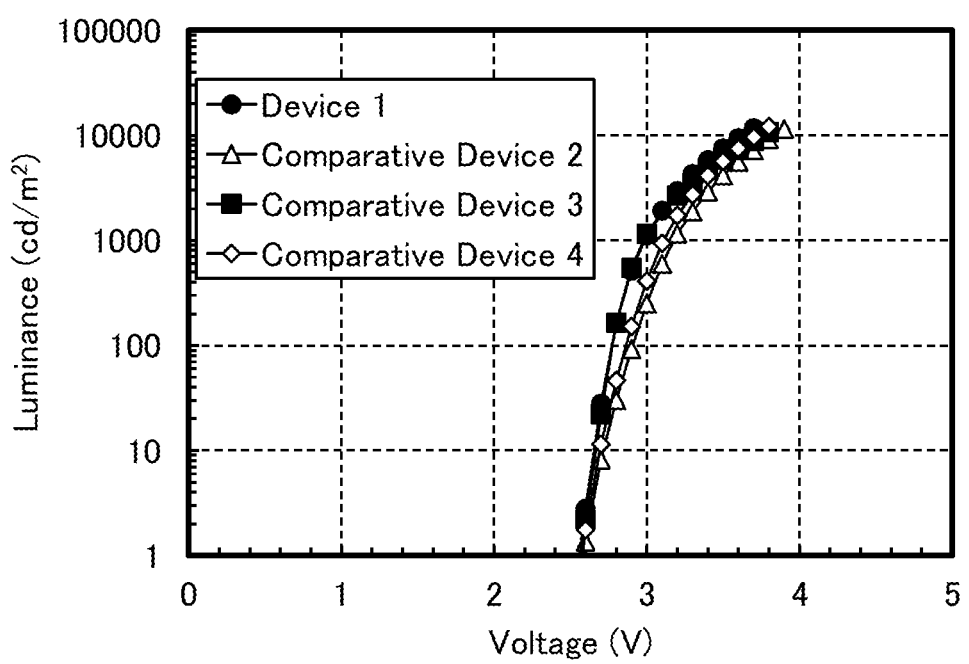
FIG. 13 shows voltage-luminance characteristics of light-emitting devices in Example 2.
Figure 14:
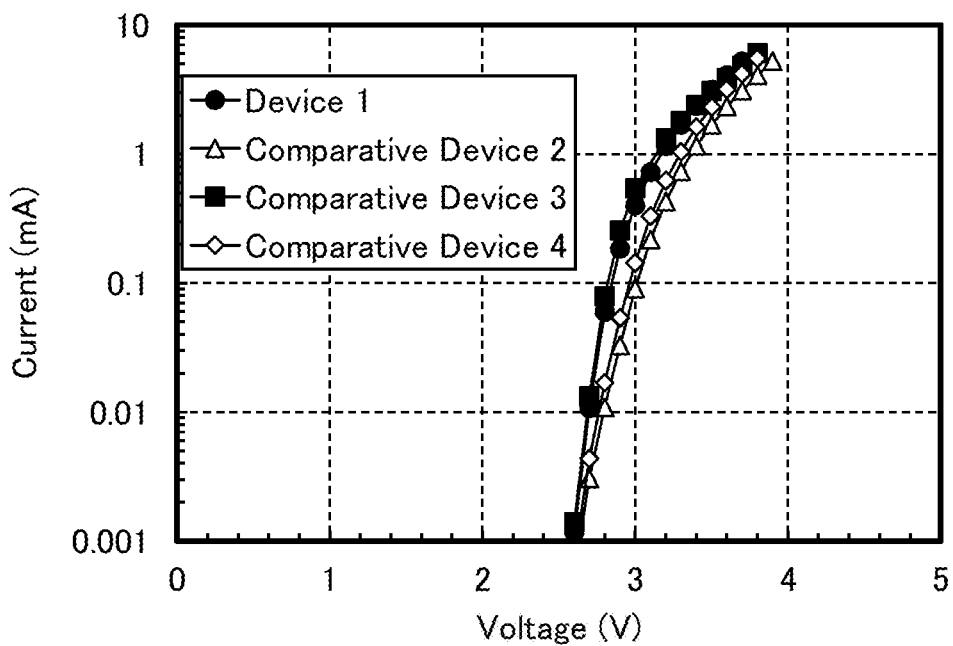
FIG. 14 shows voltage-current characteristics of light-emitting devices in Example 2.
Figure 15:
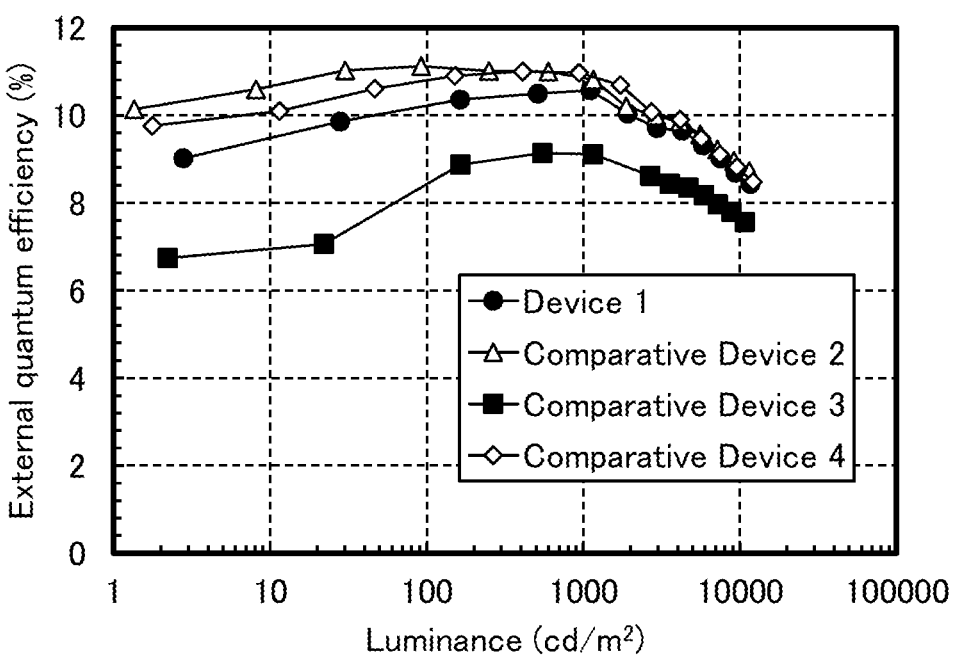
FIG. 15 shows luminance-external quantum efficiency characteristics of light-emitting devices in Example 2.

FIG. 12 shows luminance-current efficiency characteristics of the light-emitting devices. FIG. 13 shows the voltage-luminance characteristics of the light-emitting devices. FIG. 14 shows voltage-current characteristics of the light-emitting devices. FIG. 15 shows luminance-external quantum efficiency characteristics of the light-emitting devices.

Table 2 lists the initial values of main characteristics of the light-emitting devices at around 1000 cd/m$^2$.

time (h). In the reliability tests, the light-emitting devices were driven at a current density of 50 mA/cm$^2$.

After 330 hours, Device 1 kept 85% of the initial luminance, Comparative Device 2 kept 80% of the initial luminance, Comparative Device 3 kept 87% of the initial luminance, and Comparative Device 4 kept 82% of the initial luminance.

Accordingly, it is found that Device 1 has comparable emission efficiency and high reliability compared with Comparative Device 2 and Comparative Device 4. In addition, Device 1 has high emission efficiency and comparable reliability as compared with Comparative Device 3.

oYGTBiF(2) used for Device 1 is a tertiary amine. To nitrogen of the amine, the ortho position of a biphenyl skeleton, a fluorene skeleton, and a terphenylene skeleton are bonded. A carbazole skeleton is bonded to a phenylene group that is the farthest from nitrogen of amine of the terphenylene skeleton. That is, nitrogen of the amine is bonded to nitrogen of the carbazole through the terphenylene skeleton. On the other hand, oYGBBiF used for Comparative Device 2 is different from oYGTBiF(2) used for Device 1 in that nitrogen of carbazole and nitrogen of amine are bonded not through the terphenylene skeleton but through a biphenylene skeleton. Furthermore, oYGTBi1BP used for Comparative Device 3 is different from oYGTBiF (2) in that not the fluorene skeleton but the para position of a biphenyl skeleton is bonded to nitrogen of amine. YGTBiF (2) used for Comparative Device 4 is different from oYGT-BiF(2) in that not the ortho position of a biphenyl skeleton but the para position of the biphenyl skeleton is bonded to nitrogen of amine. Accordingly, the emission efficiency and

TABLE 2

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) | Energy efficiency (%) |
|---|---|---|---|---|---|---|---|---|---|
| Device 1 | 3.0 | 0.40 | 10.0 | (0.14, 0.14) | 1110 | 11.2 | 11.7 | 10.6 | 9.1 |
| Comparative Device 2 | 3.2 | 0.43 | 10.7 | (0.14, 0.13) | 1160 | 10.9 | 10.7 | 10.8 | 8.8 |
| Comparative Device 3 | 3.0 | 0.54 | 13.5 | (0.14, 0.11) | 1150 | 8.5 | 8.9 | 9.1 | 7.9 |
| Comparative Device 4 | 3.1 | 0.33 | 8.2 | (0.14, 0.13) | 940 | 11.4 | 11.5 | 11.0 | 9.2 |

As shown in FIGS. 12 to 15 and Table 2, Device 1, Comparative Device 2, and Comparative Device 4 have high emission efficiency. In addition, Device 1 has higher emission efficiency than Comparative Device 3.

Figure 16:
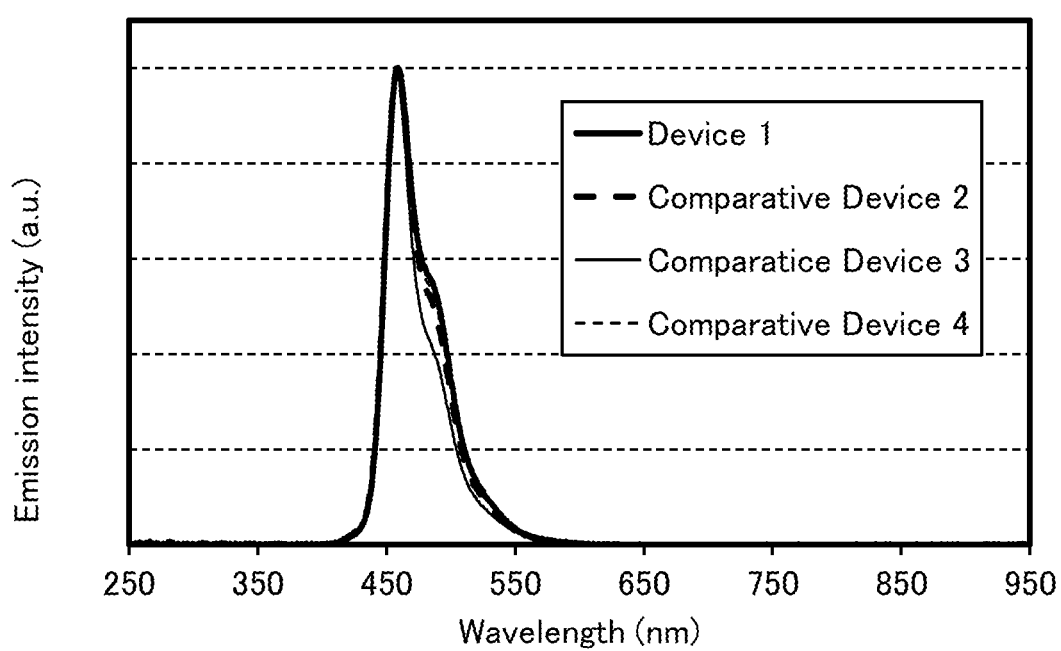
FIG. 16 shows emission spectra of light-emitting devices in Example 2.

FIG. 16 shows emission spectra when current at a current density of 12.5 mA/cm$^2$ was supplied to the light-emitting devices. As shown in FIG. 16, the emission spectrum of Device 1 has a maximum peak at around 459 nm, which is derived from 3,10PCA2Nbf(IV)-02 contained in the light-emitting layer 813. Similarly, the emission spectra of Comparative Device 2, Comparative Device 3, and Comparative Device 4 have maximum peaks at around 458 nm, 457 nm, and 459 nm, respectively.

Figure 17A:
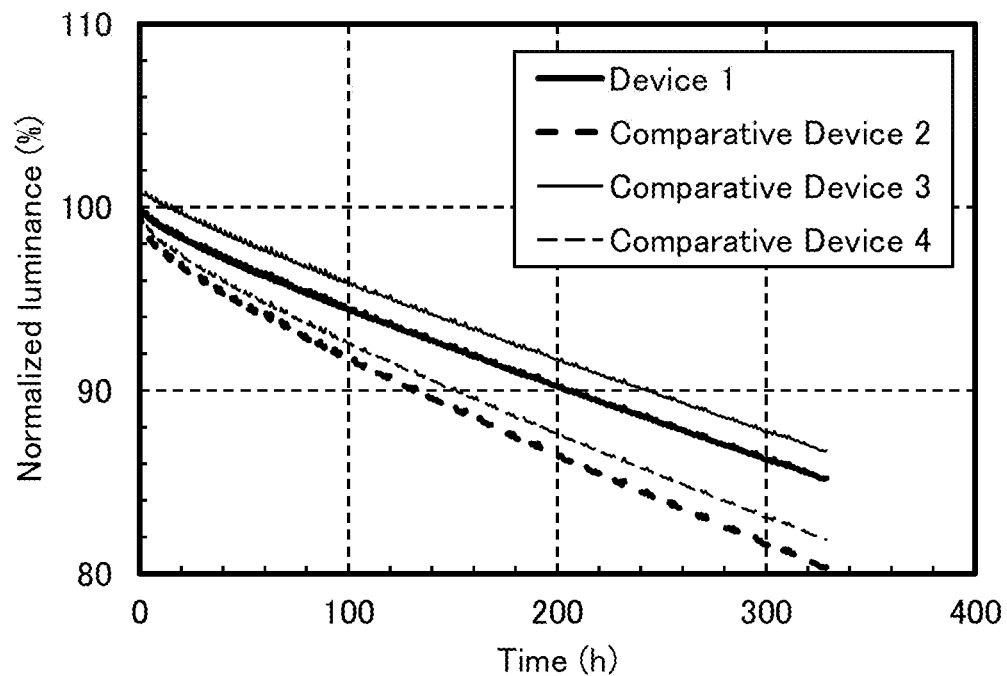
FIGS. 17A and 17B show reliability test results of light-emitting devices in Example 2.
Figure 17B:
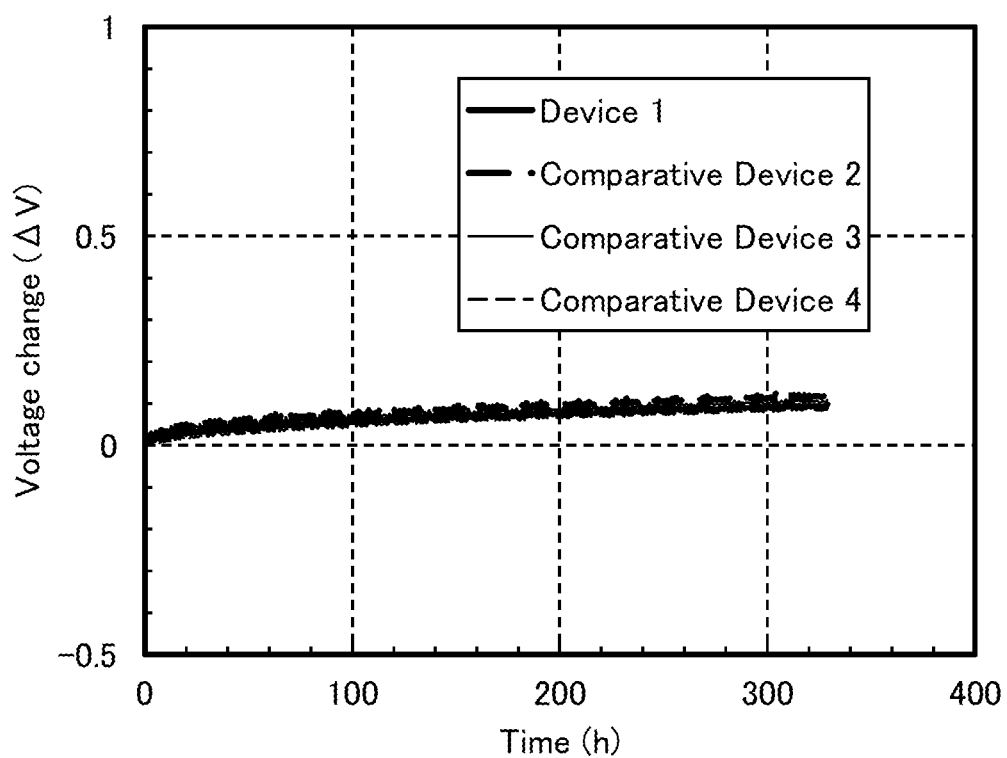

Next, reliability tests were performed on the light-emitting devices. FIGS. 17A and 17B show results of the reliability tests. In FIG. 17A, the vertical axis represents normalized luminance (%) on the assumption that the initial luminance is 100%, and the horizontal axis represents driving time (h). In FIG. 17B, the vertical axis represents the voltage change (ΔV) from the initial voltage (when the driving time is 0), and the horizontal axis represents driving the reliability of the light-emitting device can be increased with the use of the organic compound which is a tertiary amine. In the tertiary amine, the ortho position of a biphenyl skeleton, a fluorene skeleton, and a terphenylene skeleton are bonded to nitrogen of the amine; and a carbazole skeleton is bonded to a phenylene group of the terphenylene skeleton which is the farthest from nitrogen of amine.

Example 3

In this example, light-emitting devices of one embodiment of the present invention are fabricated and evaluated, and the evaluation results will be described.

In this example, Device 5 and Device 6 which use oYGTBiF(2) (Structural Formula (100)) described in Example 1 were fabricated as light-emitting devices and evaluated. The results will be described.

Table 3 shows specific structures of the two light-emitting devices used in this example. Note that Device 5 has a structure similar to that of Device 1 (FIG. 11) except for the light-emitting material of the light-emitting layer 813, and Device 6 has a structure similar to that of Device 5 except for that the thickness of the hole-transport layer 812 in Device 6 is larger than that in Device 5. Accordingly, Example 2 can be referred to for methods of fabricating components of Device 5 and Device 6 which are the same as the components of Device 1. The chemical formula of a material used in this example is shown below.

As shown in FIGS. 18 to 21 and Table 4, Device 5 and Device 6 have high emission efficiency. In spite of the fact that the thickness of the hole-transport layer 812 in Device 6 is larger than that in Device 5 by 100 nm, the driving voltage at 1000 cd/m² is increased by only 0.6 V. This means that the hole-transport property of oYGTBiF(2) is excellent.

TABLE 3

| | First electrode 801 | Hole-injection layer 811 | Hole-transport layer 812 | Light-emitting layer 813 | Electron-transport layer 814 | Electron-injection layer 815 | Second electrode 803 |
|---|---|---|---|---|---|---|---|
| Device 5 | ITSO (70 nm) | oYGTBiF(2):ALD-MP001Q (1:0.1, 10 nm) | oYGTBiF(2) (20 nm) | DBfBB1TP (10 nm) | cgDBCzPA: 1,6BnfAPrn-03 (1:0.03, 25 nm) | cgDBCzPA (15 nm) | NBPhen (10 nm) | LiF (1 nm) | Al (200 nm) |
| Device 6 | | | oYGTBiF(2) (120 nm) | | | | | |

[Chemical Formula 41]

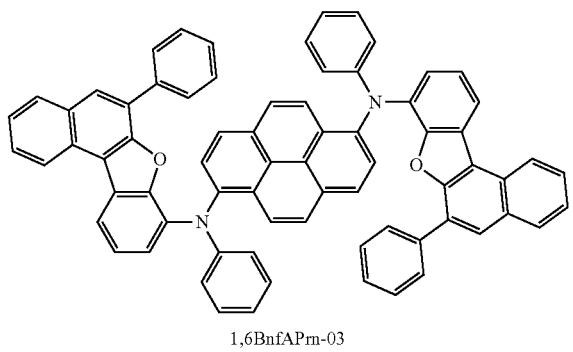

1,6BnfAPrn-03

As shown in Table 3, in the light-emitting layer 813 of the light-emitting devices in this example, cgDBCzPA was used as a host material, and N,N'-(pyrene-1,6-diyl)bis[(6,N-diphenylbenzo[b]naphtho[1,2-d]furan)-8-amine] (abbreviation: 1,6BnfAPrn-03) was used as a light-emitting material.

Furthermore, as shown in Table 3, the thicknesses of oYGTBiF(2) used for the hole-transport layer 812 are different between Device 5 and Device 6.

<<<Operation Characteristics of Light-Emitting Devices>>>

Operation characteristics of the light-emitting devices fabricated in this example were measured. Note that the measurement was performed at room temperature.

Figure 18:
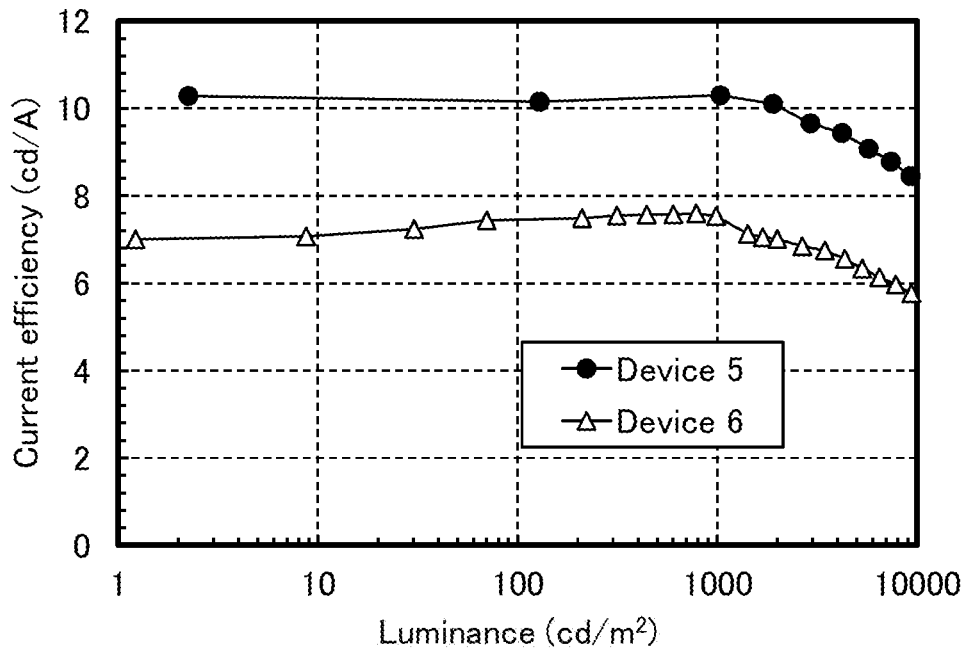
FIG. 18 shows luminance-current efficiency characteristics of light-emitting devices in Example 3.
Figure 19:
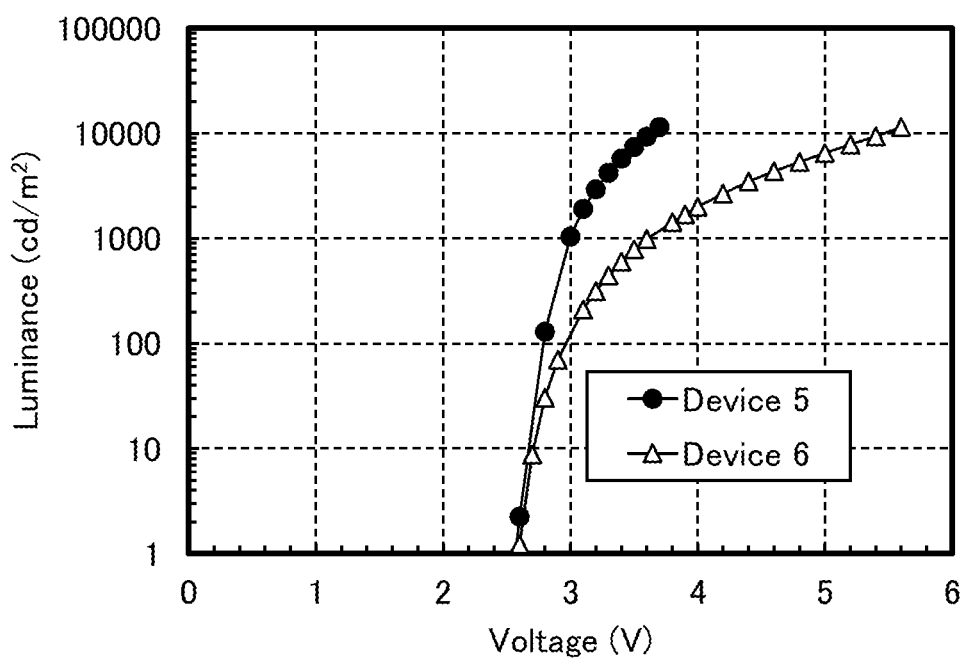
FIG. 19 shows voltage-luminance characteristics of light-emitting devices in Example 3.
Figure 20:
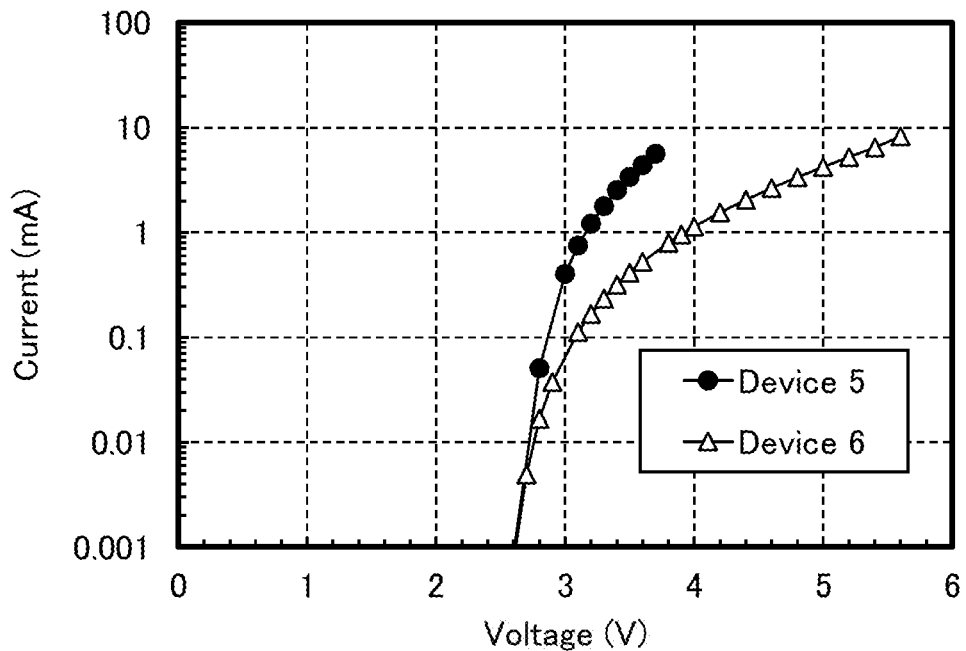
FIG. 20 shows voltage-current characteristics of light-emitting devices in Example 3.
Figure 21:
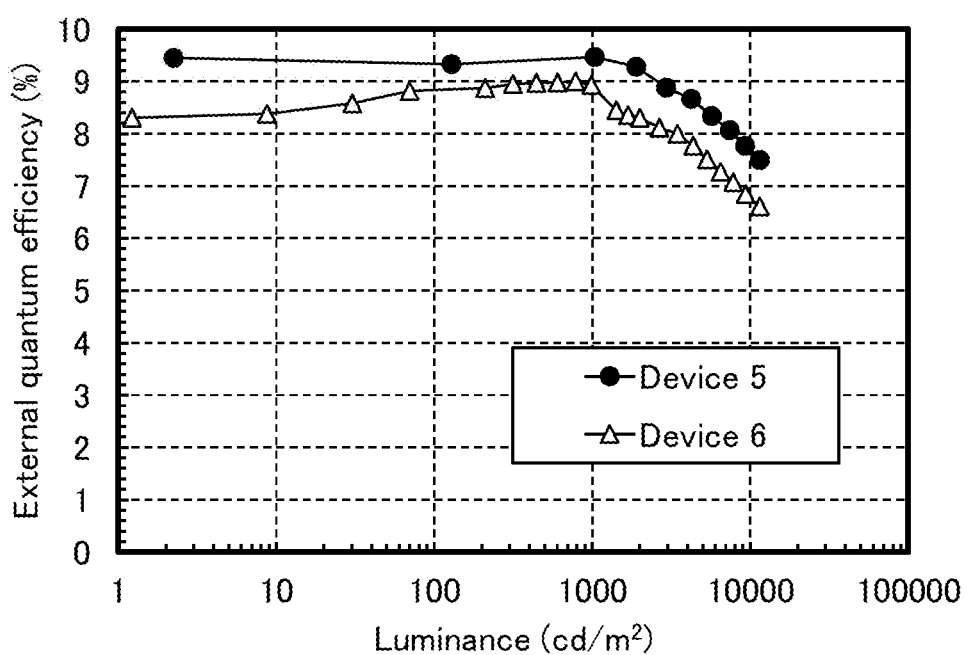
FIG. 21 shows luminance-external quantum efficiency characteristics of light-emitting devices in Example 3.

FIG. 18 shows luminance-current efficiency characteristics of the light-emitting devices. FIG. 19 shows the voltage-luminance characteristics of the light-emitting devices. FIG. 20 shows voltage-current characteristics of the light-emitting devices. FIG. 21 shows luminance-external quantum efficiency characteristics of the light-emitting devices.

Table 4 lists the initial values of main characteristics of the light-emitting devices at around 1000 cd/m².

Figure 22:
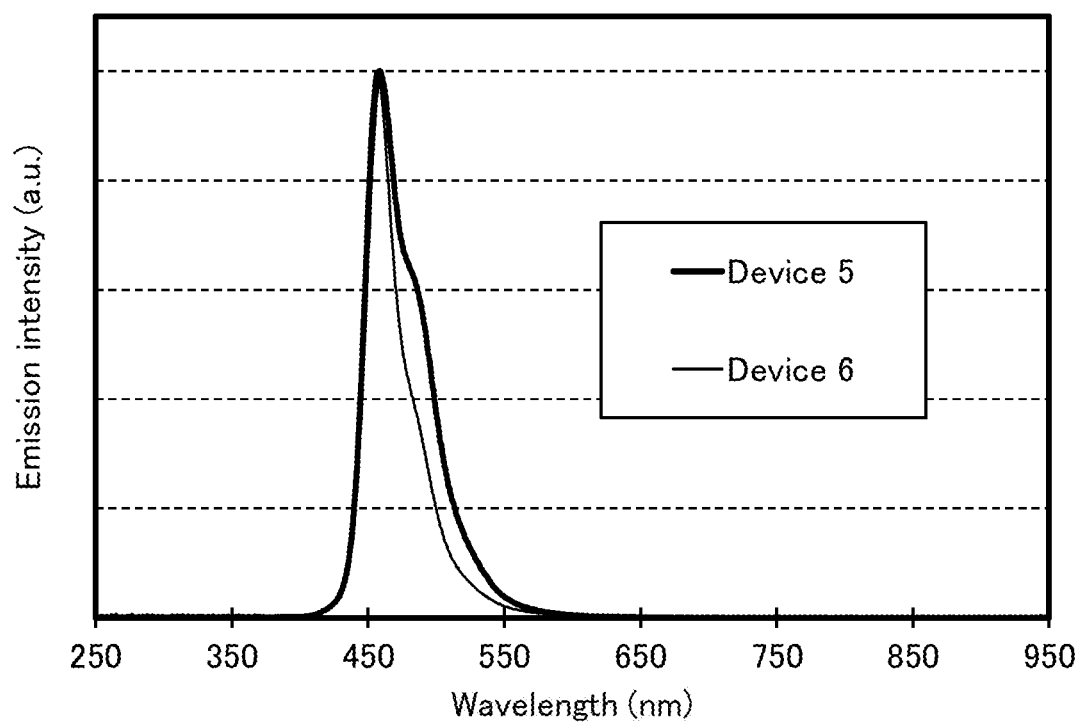
FIG. 22 shows emission spectra of light-emitting devices in Example 3.

FIG. 22 shows emission spectra when current at a current density of 12.5 mA/cm² was supplied to the light-emitting devices. As shown in FIG. 22, the emission spectrum of Device 5 has a maximum peak at around 458 nm, which is derived from 1,6BnfAPrn-03 contained in the light-emitting layer 813. Similarly, the emission spectrum of Device 6 has a maximum peak at around 456 nm. Note that the optical path length is slightly different and the emission chromaticity is also different between Device 5 and Device 6. This is because only the thickness of oYGTBiF(2) was changed and the transport properties of this material were evaluated.

Figure 23A:
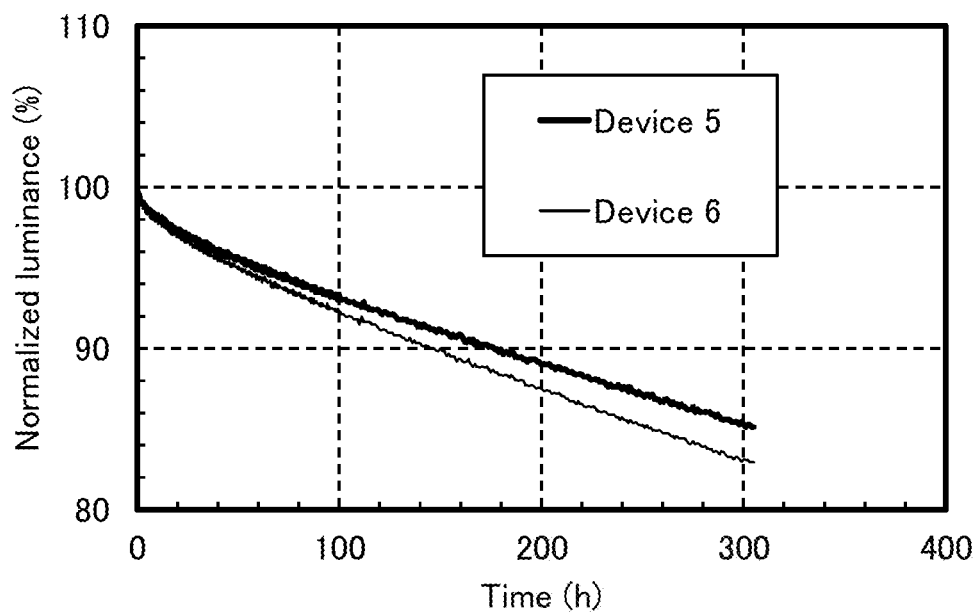
FIGS. 23A and 23B show reliability test results of light-emitting devices in Example 3.
Figure 23B:
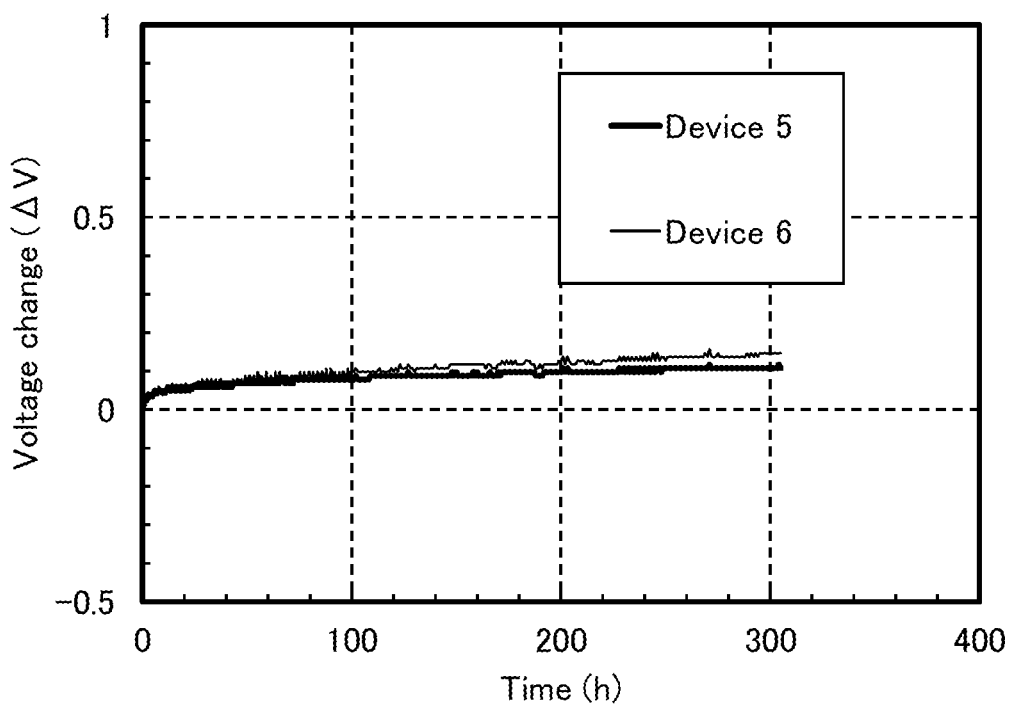

Next, reliability tests were performed on the light-emitting devices. FIGS. 23A and 23B show results of the reliability tests. In FIG. 23A, the vertical axis represents normalized luminance (%) on the assumption that the initial luminance is 100%, and the horizontal axis represents driving time (h). In FIG. 23B, the vertical axis represents the voltage change (ΔV) from the initial voltage (when the driving time is 0), and the horizontal axis represents driving time (h). In the reliability tests, the light-emitting devices were driven at a current density of 50 mA/cm².

The reliability test results show that Device 5 and Device 6 both have high reliability.

In general, when the concentration of the electron-acceptor material in the hole-injection layer is high and a hole-transport material with a deep HOMO level is used, the driving voltage of a light-emitting device is increased by increasing the thickness of the hole-transport layer in some cases. As shown in FIG. 23B, in Device 5 and Device 6, a difference between the voltage after driving for 310 hours and the initial voltage is 0.15 V or less. Therefore, it was found that even when the thickness of the hole-transport layer including the organic compound of one embodiment of the present invention is increased, the driving voltage of the light-emitting device is less likely to be increased.

TABLE 4

| | Voltage (V) | Current (mA) | Current density (mA/cm²) | Chromaticity (x, y) | Luminance (cd/m²) | Current efficiency (cd/A) | Power efficiency (lm/W) | External quantum efficiency (%) | Energy efficiency (%) |
|---|---|---|---|---|---|---|---|---|---|
| Device 5 | 3.0 | 0.40 | 10.1 | (0.14, 0.14) | 1040 | 10.3 | 10.8 | 9.5 | 8.2 |
| Device 6 | 3.6 | 0.52 | 13.1 | (0.14, 0.09) | 990 | 7.5 | 6.6 | 8.9 | 6.5 |

Example 4

In this example, light-emitting devices of one embodiment of the present invention are fabricated and evaluated, and the evaluation results will be described.

In this example, Device 7 and Device 8 which use oYGTBiF(2) (Structural Formula (100)) described in Example 1 were fabricated as light-emitting devices and evaluated. The results will be described.

Table 5 shows specific structures of the two light-emitting devices used in this example. Note that Device 7 has a structure similar to that of Device 1 (FIG. 11) except for the materials of the light-emitting layer 813 and the electron-transport layer 814, and Device 8 has a structure similar to that of Device 7 except for that the thickness of the hole-transport layer 812 in Device 8 is larger than that in Device 7. Accordingly, Example 2 can be referred to for methods of fabricating components of Device 7 and Device 8 which are the same as the components of Device 1. Note that Device 7 and Device 8 each have a structure similar to that of Device 1 (FIG. 11), and thus Example 2 can be referred to for methods of fabricating Device 7 and Device 8. The chemical formula of a material used in this example is shown below.

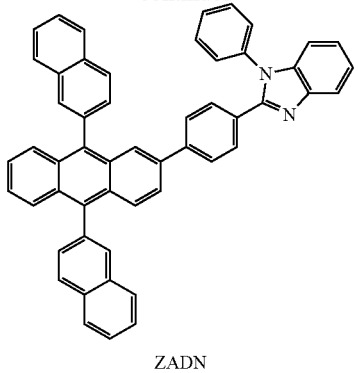

ZADN

As shown in Table 5, in the light-emitting layer 813 of each of the light-emitting devices in this example, 9-(1-naphthyl)-10-[4-(2-naphthyl)phenyl]anthracene (abbreviation: αN-βNPAnth) was used as a host material, and 1,6Bn-fAPrn-03 was used as a light-emitting material. For the electron-transport layer 814, 2-{4-[9,10-di(naphthalen-2-yl)-2-anthryl]phenyl}-1-phenyl-1H-benzimidazole (abbreviation: ZADN) and 8-hydroxyquinolinato-lithium (abbreviation: Liq) were co-evaporated to a thickness of 25 nm in a weight ratio of ZADN:Liq=1:1.

Furthermore, as shown in Table 5, the thicknesses of oYGTBiF(2) used for the hole-transport layer 812 are different between Device 7 and Device 8.

TABLE 5

| | First electrode 801 | Hole-injection layer 811 | Hole-transport layer 812 | | Light-emitting layer 813 | Electron-transport layer 814 | Electron-injection layer 815 | Second electrode 803 |
|---|---|---|---|---|---|---|---|---|
| Device 7 | ITSO (70 nm) | oYGTBiF(2):ALD-MP001Q (1:0.1, 10 nm) | oYGTBiF(2) (20 nm) | DBfBB1TP (10 nm) | αN-βNPAnth: 1,6BnfAPrn-03 (1:0.03, 25 nm) | ZADN:Liq (1:1, 25 nm) | Liq (1 nm) | Al (200 nm) |
| Device 8 | | | oYGTBiF(2) (120 nm) | | | | | |

[Chemical Formula 42]

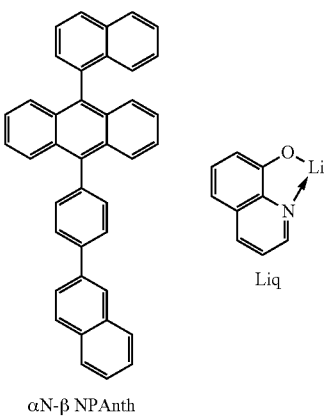

αN-β NPAnth

Liq

<<<Operation Characteristics of Light-Emitting Devices>>>

Operation characteristics of the light-emitting devices fabricated in this example were measured. Note that the measurement was performed at room temperature.

Figure 24:
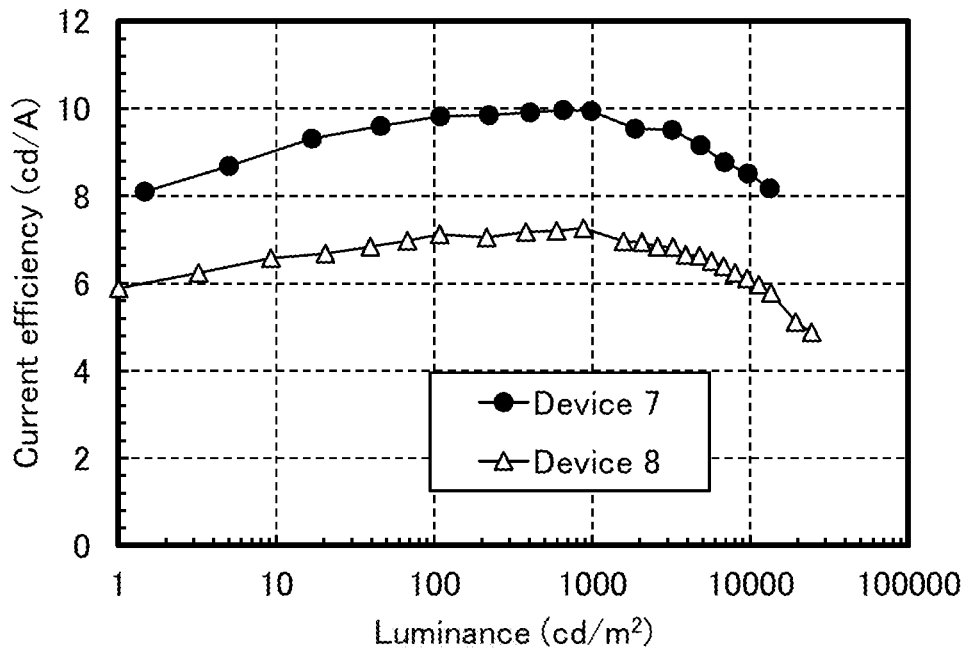
FIG. 24 shows luminance-current efficiency characteristics of light-emitting devices in Example 4.
Figure 25:
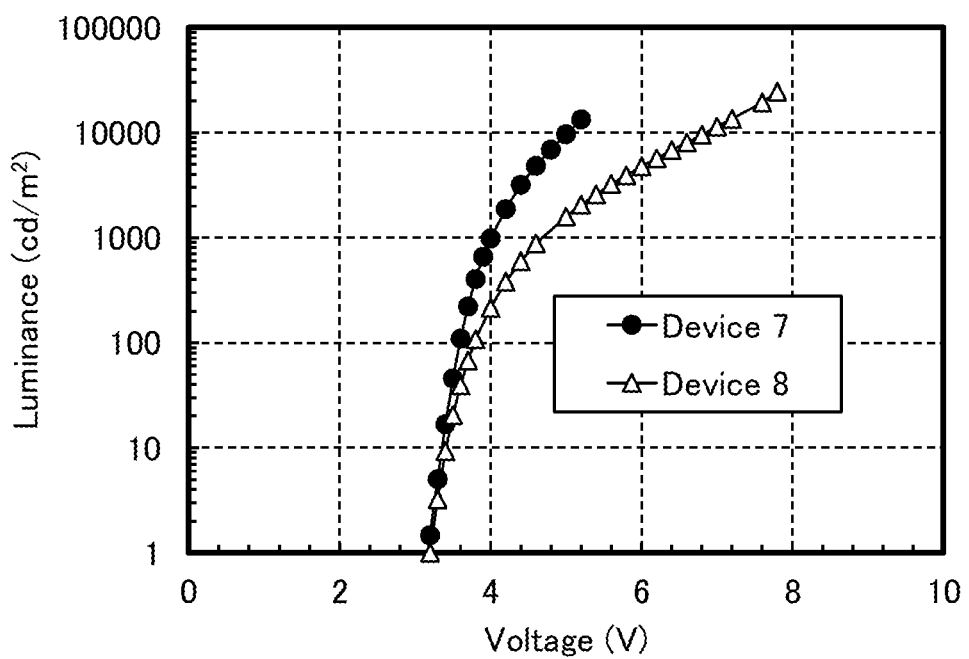
FIG. 25 shows voltage-luminance characteristics of light-emitting devices in Example 4.
Figure 26:
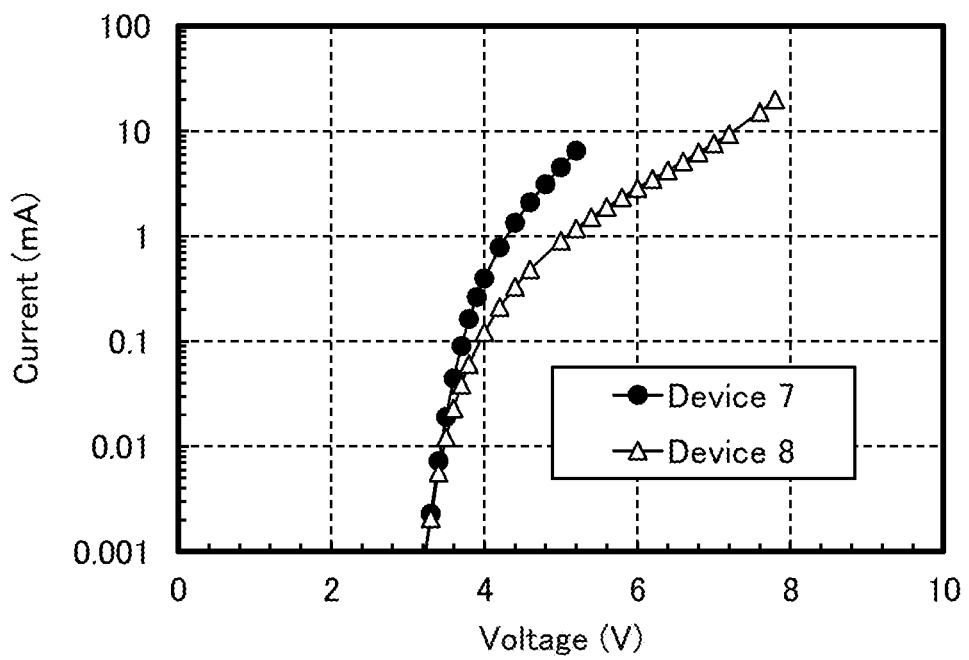
FIG. 26 shows voltage-current characteristics of light-emitting devices in Example 4.
Figure 27:
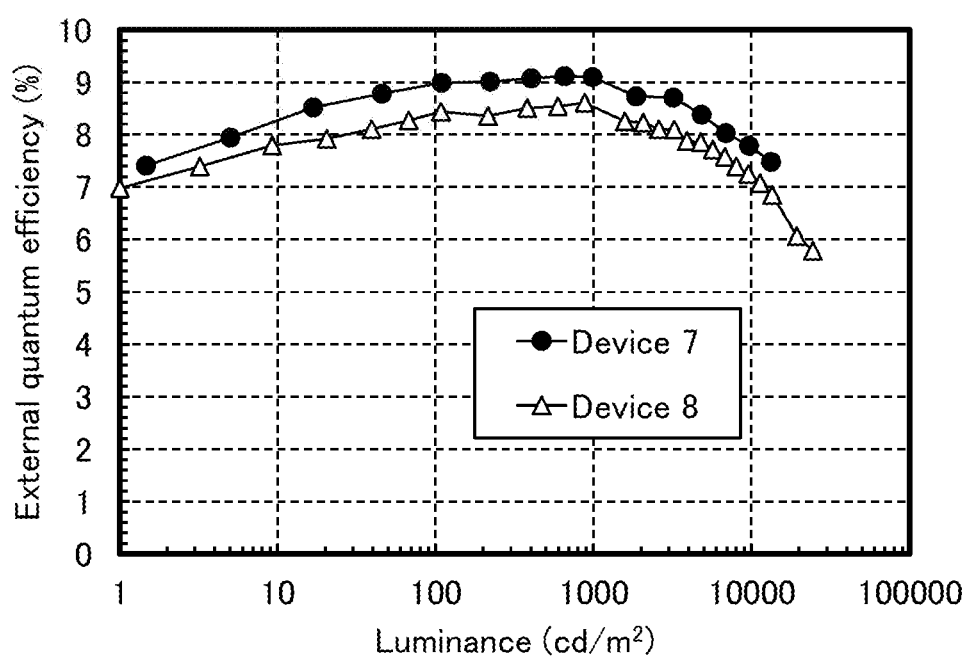
FIG. 27 shows luminance-external quantum efficiency characteristics of light-emitting devices in Example 4.

FIG. 24 shows luminance-current efficiency characteristics of the light-emitting devices. FIG. 25 shows the voltage-luminance characteristics of the light-emitting devices. FIG. 26 shows voltage-current characteristics of the light-emitting devices. FIG. 27 shows luminance-external quantum efficiency characteristics of the light-emitting devices.

Table 6 lists the initial values of main characteristics of the light-emitting devices at around 1000 cd/m$^2$.

TABLE 6

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) | Energy efficiency (%) |
|---|---|---|---|---|---|---|---|---|---|
| Device 7 | 4.0 | 0.40 | 9.9 | (0.14, 0.14) | 990 | 9.9 | 7.8 | 9.1 | 5.9 |
| Device 8 | 4.6 | 0.48 | 12.1 | (0.14, 0.09) | 880 | 7.3 | 5.0 | 8.6 | 4.9 |

As shown in FIGS. 24 to 27 and Table 6, Device 7 and Device 8 have high emission efficiency. In spite of the fact that the thickness of the hole-transport layer 812 in Device 8 is larger than that in Device 7 by 100 nm, the driving voltage at 1000 cd/m$^2$ is increased by only 0.6 V. This means that the hole-transport property of oYGTBiF(2) is excellent.

Figure 28:
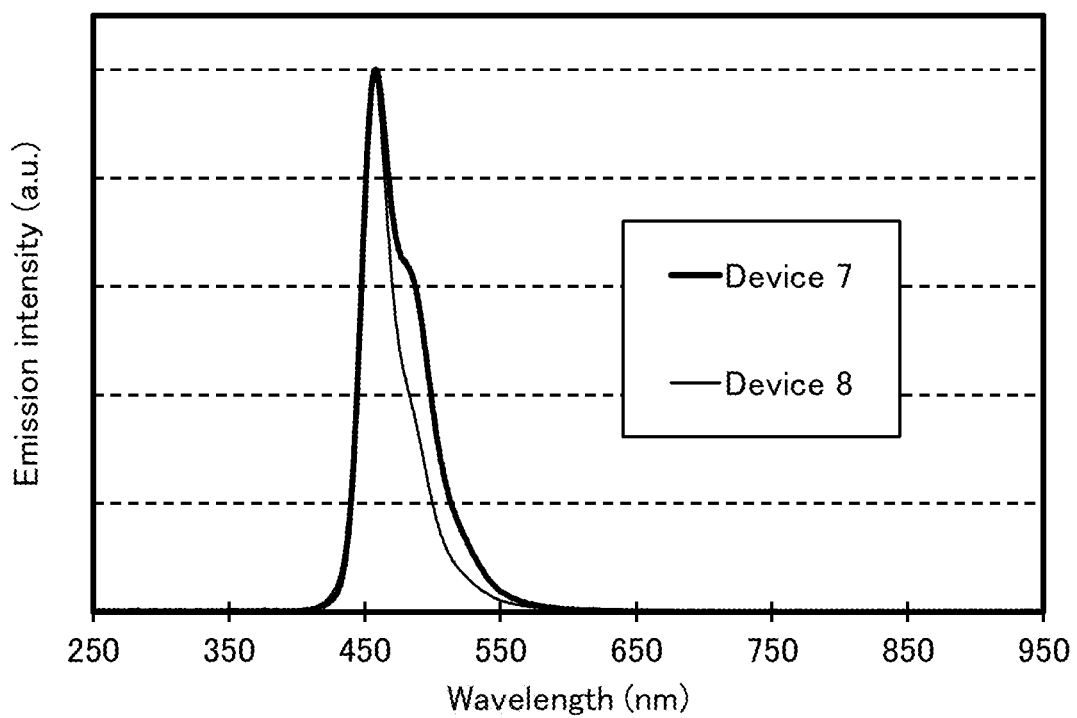
FIG. 28 shows emission spectra of light-emitting devices in Example 4.

FIG. 28 shows emission spectra when current at a current density of 12.5 mA/cm$^2$ was supplied to the light-emitting devices. As shown in FIG. 28, the emission spectrum of Device 7 has a maximum peak at around 458 nm, which is derived from 1,6BnfAPrn-03 contained in the light-emitting layer 813. Similarly, the emission spectrum of Device 8 has a maximum peak at around 456 nm. Note that the optical path length is slightly different and the emission chromaticity is also different between Device 7 and Device 8. This is because only the thickness of oYGTBiF(2) was changed and the transport properties of this material were evaluated.

Figure 29A:
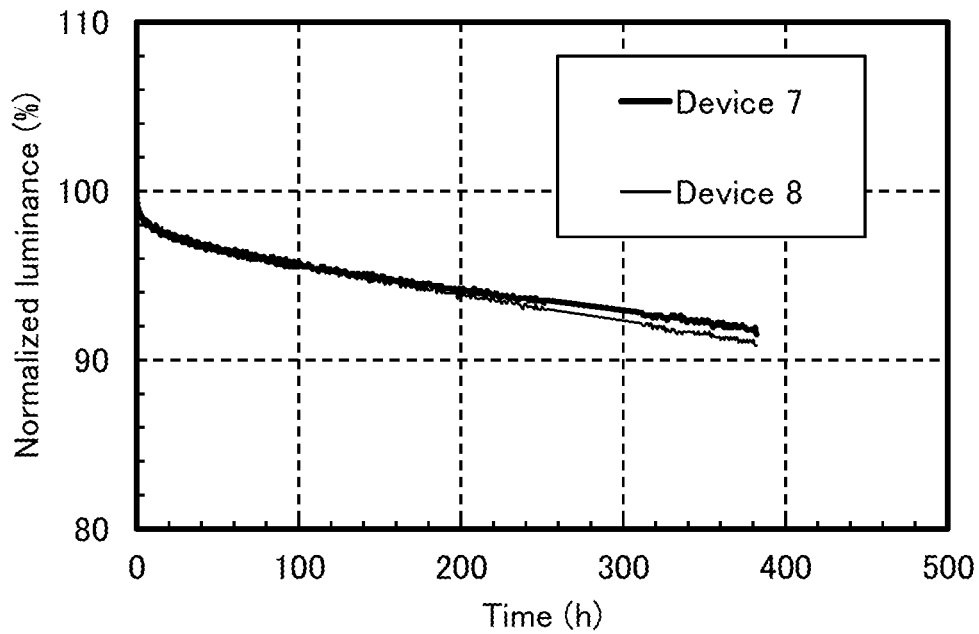
FIGS. 29A and 29B show reliability test results of light-emitting devices in Example 4.
Figure 29B:
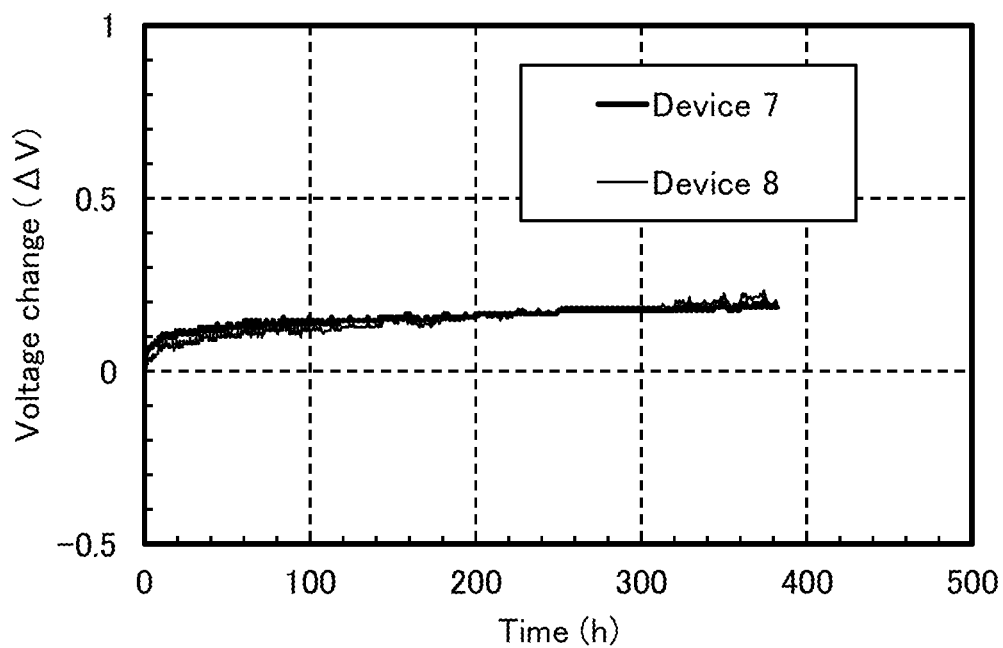

Next, reliability tests were performed on the light-emitting devices. FIGS. 29A and 29B show results of the reliability tests. In FIG. 29A, the vertical axis represents normalized luminance (%) on the assumption that the initial luminance is 100%, and the horizontal axis represents driving time (h). In FIG. 29B, the vertical axis represents the voltage change (ΔV) from the initial voltage (when the driving time is 0), and the horizontal axis represents driving time (h). In the reliability tests, the light-emitting devices were driven at a current density of 50 mA/cm$^2$.

The reliability test results show that Device 7 and Device 8 both have high reliability.

As shown in FIG. 29B, in Device 7 and Device 8, a difference between the voltage after driving for 380 hours and the initial voltage is 0.20 V or less. Therefore, it was found that even when the thickness of the hole-transport layer including the organic compound of one embodiment of the present invention is increased, the driving voltage of the light-emitting device is less likely to be increased.

The materials used for the light-emitting layers and the electron-transport layers of the light-emitting devices are different between Example 3 and Example 4. These examples show that the organic compound of one embodiment of the present invention enables a light-emitting device with high emission efficiency and high reliability by being combined with various materials.

Reference Example

Methods of synthesizing 2,4'-diphenyl-4''-[4'-(9H-carbazol-9-yl)-1,1'-biphenyl-4-yl]triphenylamine (abbreviation: oYGTBi1BP) and N-[4''-(9H-carbazol-9-yl)-1,1':4',1''-terphenyl-4-yl]-N-(1,1'-biphenyl-4-yl)-9,9-dimethyl-9H-fluoren-2-amine (abbreviation: YGTBiF(2)), which were used for the comparative devices in Example 2, will be described below.

[Chemical Formula 43]

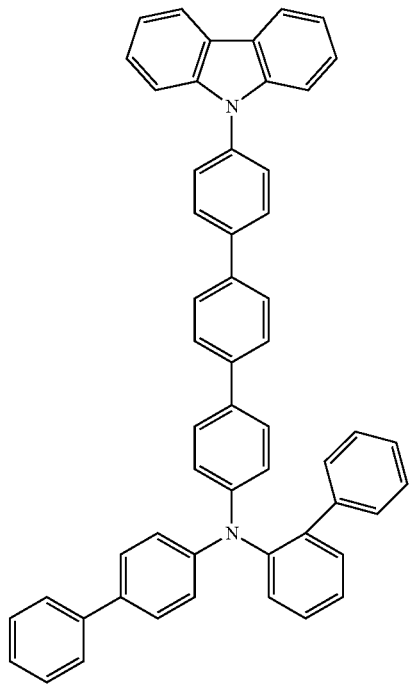

oYGTBi1BP

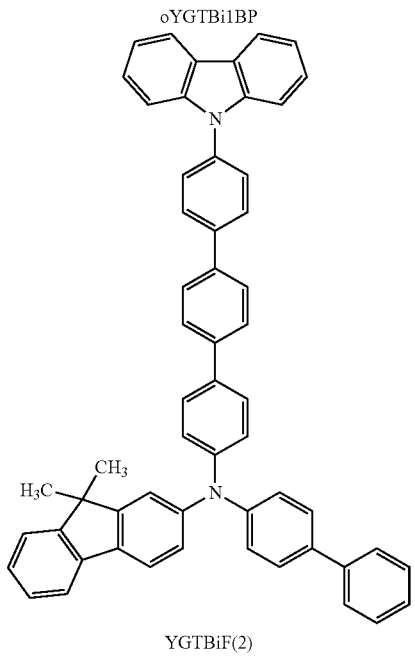

YGTBiF(2)

<Synthesis of oYGTBi1BP>

First, 1.4 g (4.2 mmol) of N-(4-biphenylyl)-2-biphenylamine, 1.8 g (4.2 mmol) of 9-(4''-chloro[1,1':4',1''-terphenyl]-4-yl)-9H-carbazole, and 30 mg (84 µmol) of di-tert-butyl(1-methyl-2,2-diphenylcyclopropyl)phosphine (registered trademark: cBRIDP) were put into a 200 mL three-neck flask equipped with a reflux pipe; then, the air in the system was replaced with nitrogen. To the system, 0.81 g (8.4 mmol) of sodium tert-butoxide and 100 mL of xylene were added. Then, degassing under reduced pressure and replacement of the air in the system with nitrogen were performed three times. To the system, 24 mg (42 µmol) of bis(dibenzylideneacetone)palladium(0) was added, and the mixture was stirred at 150° C. for 11 hours. After the stirring, an insoluble matter was removed from the mixture by suction filtration. Water was added to the obtained filtrate so that an aqueous layer was subjected to extraction with toluene. The obtained organic layer was washed twice with water and then washed with saturated saline. The organic layer was dried with magnesium sulfate. The obtained mixture was gravity-filtered to remove the magnesium sulfate. The obtained filtrate was purified by filtration of alumina and Celite (produced by Wako Pure Chemical Industries, Ltd., Catalog No. 531-16855), and the resulting filtrate was concentrated to give 2.3 g of a pale yellow solid. The obtained solid was purified by recrystallization (using a mixed solvent of toluene and hexane) to give 1.5 g of a target pale yellow solid in a yield of 50%.

By a train sublimation method, 1.5 g of the obtained solid was purified. In the sublimation purification, the solid was heated at 345° C. for 16 hours under a pressure of 3.8 Pa with an argon flow rate of 15 mL/min. After the sublimation purification, 1.0 g of a target pale yellow solid was obtained at a collection rate of 66%. Synthesis Scheme (X-1) is shown below.

[Chemical Formula 44]

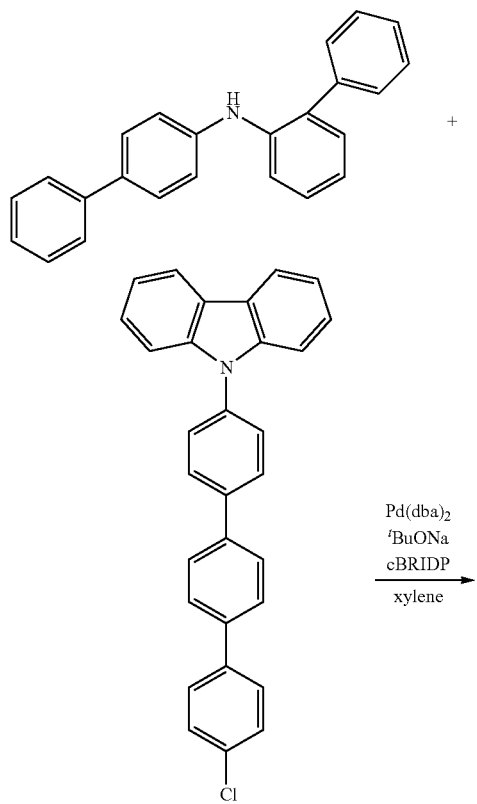

(X-1)

-continued

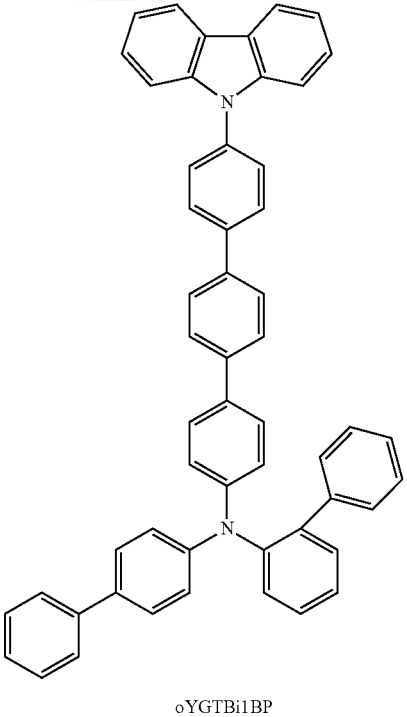

oYGTBi1BP

Analysis results by $^1$H NMR of the obtained pale yellow solid are shown below. The results show that oYGTBi1BP was obtained.

$^1$H NMR (dichloromethane-d$_2$, 300 MHz): δ=8.16 (d, J=8.1 Hz, 2H), 7.90 (dd, J1=4.5 Hz, J2=1.8 Hz, 2H), 7.77 (dd, J1=4.2 Hz, J2=2.1 Hz, 2H), 7.70-7.66 (m, 4H), 7.55-7.14 (m, 24H), 6.99 (d, J=5.7 Hz, 2H), 6.96 (d, J=5.7 Hz, 2H).

Next, absorption spectra and emission spectra of oYGTBi1BP in a toluene solution and a solid thin film of oYGTBi1BP were measured. Note that the measurement conditions are similar to those in Example 1 and thus description thereof is omitted.

An absorption peak of oYGTBi1BP in the toluene solution was observed at around 365 nm, and an emission peak thereof was observed at around 411 nm (excitation wavelength: 346 nm). Absorption peaks of oYGTBi1BP in a solid thin film were observed at around 296 nm, 347 nm, and 362 nm, and an emission peak thereof was observed at around 426 nm (excitation wavelength: 360 nm).

Next, the HOMO level and the LUMO level of oYGTBi1BP were calculated by CV measurement. The calculation method is similar to that of Example 1 and thus description thereof is omitted.

Furthermore, CV measurement was repeated 100 times, and the oxidation-reduction wave in the hundredth cycle was compared with the oxidation-reduction wave in the first cycle to examine the electrical stability of the compound.

As a result, in the measurement of an oxidation potential Ea [V] of oYGTBi1BP, the HOMO level was −5.50 eV In contrast, the LUMO level was −2.32 eV in the measurement of the reduction potential Ec[V]. When the oxidation-reduction wave was repeatedly measured, in the Ea measurement, the peak intensity of the oxidation-reduction wave after the hundredth cycle was maintained to be 85% of that of the oxidation-reduction wave in the first cycle, and in the Ec measurement, the peak intensity of the oxidation-reduction wave after the hundredth cycle was maintained to be 94% of that of the oxidation-reduction wave in the first cycle; thus, resistance to oxidation and reduction of oYGTBi1BP was found to be extremely high.

Differential scanning calorimetry (DSC measurement) was performed on oYGTBi1BP by Pyris1DSC produced by PerkinElmer, Inc. In the differential scanning calorimetry, after the temperature was raised from −10° C. to 380° C. at a temperature rising rate of 40° C./min, the temperature was held for a minute and then decreased to −10° C. at a temperature decreasing rate of 100° C./min. This operation was repeated twice successively. It was found from the DSC measurement result of the second cycle that the glass transition point of oYGTBi1BP is 122° C., that is, oYGTBi1BP is a substance with extremely high heat resistance.

The thermogravimetry-differential thermal analysis of oYGTBi1BP was performed. The measurement method is similar to that of Example 1 and thus description thereof is omitted. In the thermogravimetry-differential thermal analysis, the temperature (decomposition temperature) at which the weight obtained by thermogravimetry was reduced by 5% of the weight at the beginning of the measurement was found to be 486° C., which shows that oYGTBi1BP is a substance with high heat resistance.

<Synthesis of YGTBiF(2)>

Into a 200 mL three-neck flask equipped with a reflux pipe, 2.0 g (4.0 mmol) of 2-amino-N-[(1,1'-biphenyl)-4-yl]-N-(4-bromophenyl)-9,9-dimethylfluorene, 1.4 g (4.0 mmol) of [4'-(carbazol-9-yl)-4-biphenylyl]boronic acid, 24 mg (76 μmol) of tri(ortho-tolyl)phosphine, 5 mL of a 2M potassium carbonate solution, 30 mL of toluene, and 10 mL of ethanol were put, the mixture was degassed under reduced pressure, and the air in the system was replaced with nitrogen. This mixture was heated at 60° C., and 8.9 mg (40 μmol) of palladium(II) acetate was added thereto. This mixture was refluxed for 10 hours. The obtained mixture was suction-filtered. Water was added to the obtained filtrate, and an aqueous layer was subjected to extraction with toluene. The extracted solution was combined with an organic layer, and the resulting mixture was washed with water and saturated saline and dried with magnesium sulfate. This mixture was gravity-filtered, and the obtained filtrate was concentrated to give a pale brown solid. This solid was purified by high performance liquid chromatography (HPLC) (mobile phase: chloroform) to give 1.3 g of a target pale yellow solid in a yield of 43%.

By a train sublimation method, 1.3 g of the obtained solid was purified. In the sublimation purification, the solid was heated at 350° C. for 15 hours under a pressure of 3.1 Pa with an argon flow rate of 15 mL/min. After the sublimation purification, 1.1 g of a target pale yellow solid was obtained at a collection rate of 85%. Synthesis Scheme (Y-1) is shown below.

[Chemical Formula 45]

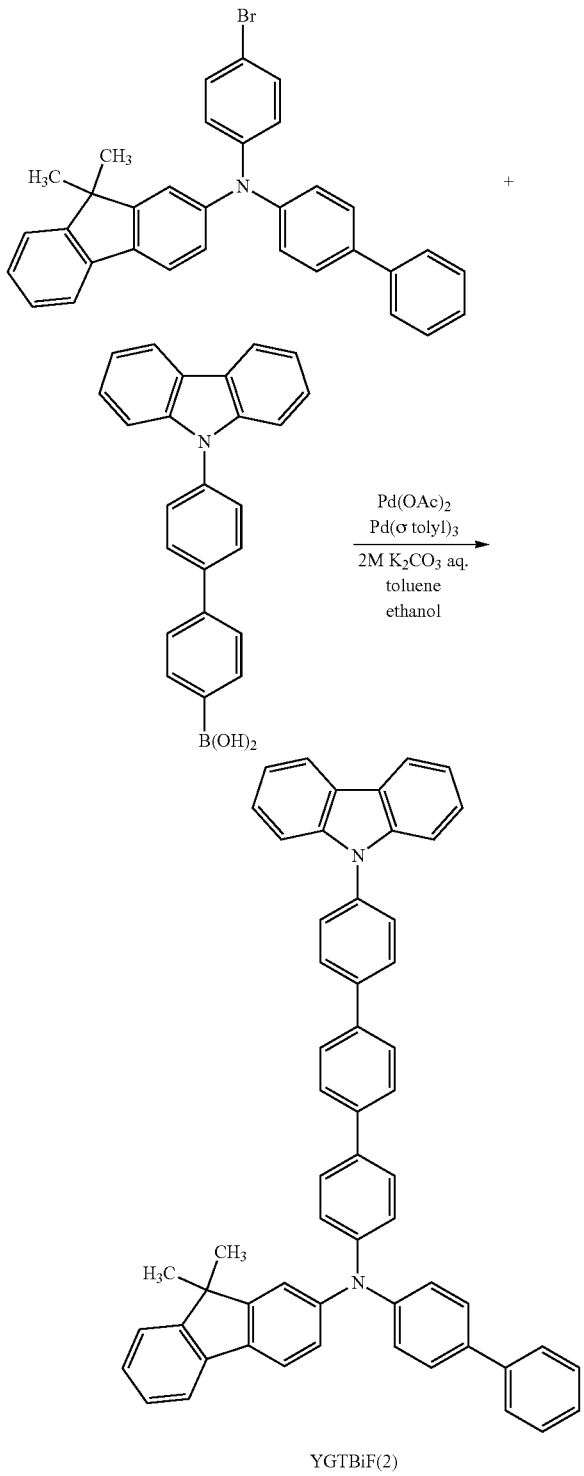

YGTBiF(2)

Analysis results by $^1$H NMR of the obtained pale yellow solid are shown below. The results show that YGTBiF(2) was obtained.

$^1$H NMR (dichloromethane-d$_2$, 300 MHz): δ=8.17 (d, J=7.8 Hz, 2H), 7.92 (d, J=8.7 Hz, 2H), 7.75 (dd, J1=27.6 Hz, J2=9.0 Hz, 4H), 7.70-7.61 (m, 8H), 7.56 (d, J=9.0 Hz, 2H), 7.52-7.42 (m, 7H), 7.36-7.24 (m, 10H), 7.14 (dd, J1=6.0 Hz, J2=2.1 Hz, 1H), 1.45 (s, 6H).

Next, absorption spectra and emission spectra of YGTBiF (2) in a toluene solution and a solid thin film of YGTBiF(2) were measured. Note that the measurement conditions are similar to those in Example 1 and thus description thereof is omitted.

An absorption peak of oYGTBiF(2) in the toluene solution was observed at around 363 nm, and an emission peak thereof was observed at around 425 nm (excitation wavelength: 363 nm). Absorption peaks of YGTBiF(2) in a solid thin film were observed at around 294 nm, 350 nm, and 365 nm, and an emission peak thereof was observed at around 442 nm (excitation wavelength: 380 nm).

Next, the HOMO level and the LUMO level of YGTBiF (2) were calculated by CV measurement. The calculation method is similar to that of Example 1 and thus description thereof is omitted.

Furthermore, CV measurement was repeated 100 times, and the oxidation-reduction wave in the hundredth cycle was compared with the oxidation-reduction wave in the first cycle to examine the electrical stability of the compound.

As a result, in the measurement of an oxidation potential Ea [V] of YGTBiF(2), the HOMO level was −5.41 eV In contrast, the LUMO level was −2.34 eV in the measurement of the reduction potential Ec [V]. When the oxidation-reduction wave was repeatedly measured, in the Ea measurement, the peak intensity of the oxidation-reduction wave after the hundredth cycle was maintained to be 90% of that of the oxidation-reduction wave in the first cycle, and in the Ec measurement, the peak intensity of the oxidation-reduction wave after the hundredth cycle was maintained to be 96% of that of the oxidation-reduction wave in the first cycle; thus, resistance to oxidation and reduction of YGTBiF (2) was found to be extremely high.

Differential scanning calorimetry (DSC measurement) was performed on YGTBiF(2) by Pyris1DSC produced by PerkinElmer, Inc. In the differential scanning calorimetry, after the temperature was raised from −10° C. to 330° C. at a temperature rising rate of 40° C./min, the temperature was held for a minute and then decreased to −10° C. at a temperature decreasing rate of 100° C./min. This operation was repeated twice successively. It was found from the DSC measurement result of the second cycle that the glass transition point of YGTBiF(2) is 145° C., that is, YGTBiF(2) is a substance with extremely high heat resistance.

The thermogravimetry-differential thermal analysis of YGTBiF(2) was performed. The measurement method is similar to that of Example 1 and thus description thereof is omitted. In the thermogravimetry-differential thermal analysis, the temperature (decomposition temperature) at which the weight obtained by thermogravimetry was reduced by 5% of the weight at the beginning of the measurement was found to be 499° C., which shows that YGTBiF(2) is a substance with high heat resistance.

This application is based on Japanese Patent Application Serial No. 2019-129980 filed with Japan Patent Office on Jul. 12, 2019, the entire contents of which are hereby incorporated by reference.

What is claimed is:

1. An organic compound represented by Formula (G0):

[Chemical Formula 1]

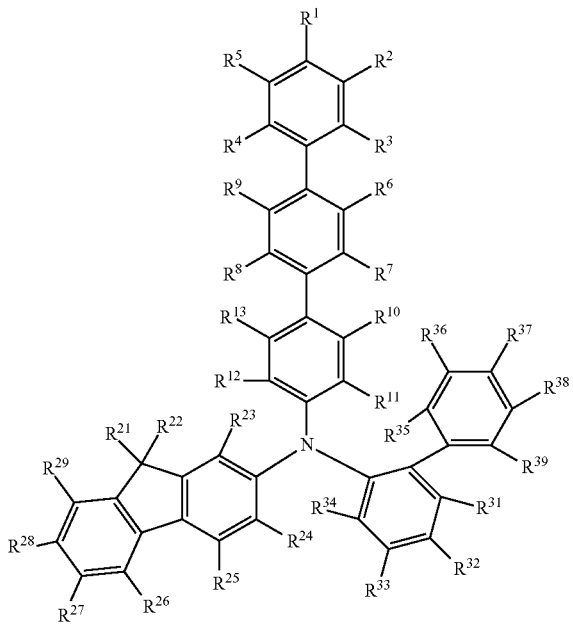

(G0)

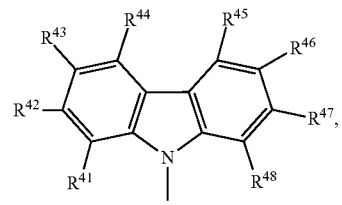

(A)

wherein any one of $R^1$ to $R^5$ represents Formula (A), wherein each of the others of $R^1$ to $R^5$ independently represents any one of hydrogen, an alkyl group having 1 to 6 carbon atoms, a cycloalkyl group having 3 to 6 carbon atoms, and a substituted or unsubstituted aryl group having 6 to 13 carbon atoms, wherein each of $R^6$ to $R^{13}$, $R^{23}$ to $R^{29}$, $R^{31}$ to $R^{39}$, and $R^{41}$ to $R^{48}$ independently represents any one of hydrogen, an alkyl group having 1 to 6 carbon atoms, a cycloalkyl group having 3 to 6 carbon atoms, and a substituted or unsubstituted aryl group having 6 to 13 carbon atoms, and wherein each of $R^{21}$ and $R^{22}$ represents a methyl group.

2. The organic compound according to claim 1, wherein the organic compound is represented by Formula (G1):

[Chemical Formula 2]

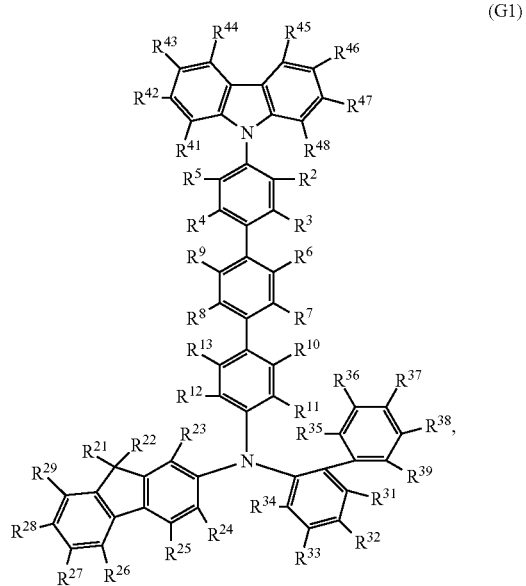

(G1)

wherein each of $R^2$ to $R^5$ independently represents any one of hydrogen, an alkyl group having 1 to 6 carbon atoms, a cycloalkyl group having 3 to 6 carbon atoms, and a substituted or unsubstituted aryl group having 6 to 13 carbon atoms.

3. The organic compound according to claim 1, wherein one of $R^{35}$ to $R^{39}$ represents any one of a substituted or unsubstituted phenyl group and a substituted or unsubstituted naphthyl group.

4. The organic compound according to claim 1, wherein each of $R^{41}$ to $R^{48}$ independently represents any one of hydrogen, a methyl group, a tert-butyl group and a substituted or unsubstituted phenyl group.

5. A light-emitting device comprising the organic compound according to claim 1.

6. A light-emitting device comprising:
a pair of electrodes; and
a layer between the pair of electrodes, the layer comprising the organic compound according to claim 1.

7. A light-emitting device comprising:
a first electrode;
a hole-transport layer over the first electrode;
a light-emitting layer over the hole-transport layer; and
a second electrode over the light-emitting layer,
wherein at least one of the light-emitting layer and the hole-transport layer comprises the organic compound according to claim 1.

8. A light-emitting apparatus comprising:
the light-emitting device according to claim 5; and
at least one of a transistor and a substrate.

9. A light-emitting module comprising:
the light-emitting apparatus according to claim 8; and
at least one of a connector and an integrated circuit.

10. An electronic device comprising:
the light-emitting apparatus according to claim 8; and
at least one of an antenna, a battery, a housing, a camera, a speaker, a microphone and an operation button.

11. A lighting device comprising:
the light-emitting device according to claim 5; and
at least one of a housing, a cover and a support base.

12. A light-receiving device comprising:
a pair of electrodes; and
a layer between the pair of electrodes, the layer comprising the organic compound according to claim 1.

* * * * *